United States Patent
Yokoyama et al.

(10) Patent No.: US 9,340,790 B2
(45) Date of Patent: May 17, 2016

(54) METHOD FOR CONSTRUCTING RECOMBINANT BACTERIUM FOR PRODUCING NON-NATIVE PROTEIN, AND UTILIZATION OF SAME

(75) Inventors: Shigeyuki Yokoyama, Yokohama (JP); Takahito Mukai, Yokohama (JP); Kensaku Sakamoto, Yokohama (JP); Akiko Matsumoto, Yokohama (JP)

(73) Assignee: RIKEN, Wako-shi, Saitama (JP)

( * ) Notice: Subject to any disclaimer, the term of this patent is extended or adjusted under 35 U.S.C. 154(b) by 728 days.

(21) Appl. No.: 13/704,391

(22) PCT Filed: Jun. 16, 2011

(86) PCT No.: PCT/JP2011/063778
§ 371 (c)(1),
(2), (4) Date: Dec. 14, 2012

(87) PCT Pub. No.: WO2011/158895
PCT Pub. Date: Dec. 22, 2011

(65) Prior Publication Data
US 2013/0095524 A1 Apr. 18, 2013

(30) Foreign Application Priority Data

Jun. 16, 2010 (JP) ................................. 2010-137635
Mar. 4, 2011 (JP) ................................. 2011-047663

(51) Int. Cl.
| | | |
|---|---|---|
| C12N 15/64 | (2006.01) | |
| C12N 15/70 | (2006.01) | |
| C12N 15/67 | (2006.01) | |
| C12P 21/02 | (2006.01) | |
| C07K 14/245 | (2006.01) | |
| C12N 9/00 | (2006.01) | |
| C12N 15/11 | (2006.01) | |

(52) U.S. Cl.
CPC .............. *C12N 15/70* (2013.01); *C07K 14/245* (2013.01); *C12N 9/93* (2013.01); *C12N 15/11* (2013.01); *C12N 15/67* (2013.01); *C12P 21/02* (2013.01); *Y02P 20/52* (2015.11)

(58) Field of Classification Search
None
See application file for complete search history.

(56) References Cited

U.S. PATENT DOCUMENTS

| | | |
|---|---|---|
| 2009/0087879 A1 | 4/2009 | Gerrits et al. |
| 2009/0317910 A1 | 12/2009 | Church |
| 2010/0105565 A1 | 4/2010 | Chin et al. |

FOREIGN PATENT DOCUMENTS

| | | |
|---|---|---|
| EP | 1456360 A2 | 9/2004 |
| EP | 1490483 A2 | 12/2004 |
| EP | 2128246 A1 | 12/2009 |
| EP | 2322631 A1 | 5/2011 |
| JP | 2005-502322 A | 1/2005 |
| JP | 2007-501007 A | 1/2007 |
| JP | 2007-082543 | 4/2007 |
| JP | 2010-510798 A | 4/2010 |
| WO | 02/085923 | 10/2002 |
| WO | 2008/065398 | 6/2008 |

OTHER PUBLICATIONS

Search Report of corresponding EP Patent Application No. 11795797.7 dated Oct. 7, 2013.
Taira, Hikaru, et al., "Comprehensive screening of amber suppressor tRNAs suitable for incorporation of non-natural amino acids in a cell-free translation system," Biochemical and Biophysical Research Communications, vol. 374, No. 2 ( Sep. 19, 2008), pp. 304-308.
Baba, T., et al., "Construction of *Escherichia coli* K-12 in-frame, single-gene knockout mutants: the Keio collection", Molecular Systems Biology, 2006, pp. 1-11.
Chin, J.W., "Addition of p-Azido-L-phenylalanine to the Genetic Code of *Escherichia coli*," J. Am. Chem. Soc. (2002), pp. 9026-9027.
Chin, J.W., et al., "Addition of a photocrosslinking amino acid to the genetic code of *Escherichia coli*," PNAS, Aug. 20, 2002, vol. 99, No. 17, pp. 11020-11024.
Forster, Anthony C., et al., "Synthetic Biology Projects in Vitro," Genome Research, vol. 17, No. 1 (2007), pp. 1-6.
Guo, J., et al., "Addition of an α-Hydroxy Acid to the Genetic Code of Bacteria," Angew. Chem. Int. Ed. vol. 47, 2008, pp. 722-725.
Guo, J., et al., "Evolution of Amber Suppressor tRNAs for Efficient Bacterial Production of Proteins Containing Nonnatural Amino Acids," Angew. Chem. Int. Ed., vol. 48, 2009, pp. 9148-9151.
Iraha, F., et al., "Functional replacement of the endogenous tyrosyl-tRNA synthetase-tRNA(Tyr) pair by the archaeal tyrosine pair in *Escherichia coli* for genetic code expansion," Nucleic Acids Research, 2010, vol. 38, No. 11, Feb. 16, 2010, pp. 3682-3691.
Jeong, H., et al., "Genome Sequences of *Escherichia coli* B strains REL606 and BL21(DE3)," J. Mol. Biol., vol. 394, 2009, pp. 644-652.
Kato, J., et al., "Construction of consecutive deletions of the *Escherichia coli* chromosome," Mol. Syst. Biol., vol. 3, No. 132, 2007, pp. 1-7.
Kato, J., et al., "Hda, a novel DnaA-related protein, regulates the replication cycle in *Escherichia coli*," The EMBO Journal, vol. 20, No. 15, 2001, pp. 4253-4262.

(Continued)

*Primary Examiner* — Jim Ketter
(74) *Attorney, Agent, or Firm* — Casimir Jones, SC

(57) ABSTRACT

The present invention provides a novel method of producing a recombinant bacterium for production of a non-natural protein, including: (1) expressing tRNA in a bacterium, which tRNA recognizes UAG codon; (2) expressing an aminoacyl-tRNA synthetase in the bacterium, which aminoacyl-tRNA synthetase acylates the tRNA with a non-natural amino acid or an α-hydroxy acid; (3) (i) introducing a DNA construct into the bacterium, which DNA construct is for expressing, in the absence of a release factor for terminating translation at UAG codon, a function of at least one gene selected from the group consisting of genes each of which loses its function when a gene that codes for the release factor is defective and/or introducing an alteration into said at least one gene in a chromosome of the bacterium, which alteration is for expressing the function of said at least one gene in the absence of the release factor; and (4) causing the gene that codes for the release factor in the bacterium to be defective.

33 Claims, 26 Drawing Sheets

(56) References Cited

OTHER PUBLICATIONS

Kigawa, T., et al., "Preparation of *Escherichia coli* cell extract for highly productive cell-free protein expression," J. Struct. Funct. Genomics, vol. 5, 2004, pp. 63-68.

Kleina, L.G., "Construction of *Escherichia coli* Amber Suppressor tRNA Genes," J. Mol. Biol. (1990) 213, pp. 705-717.

Mukai, T., "A study on the genetic code . . . ", Doctor Thesis Presentation, the University of Tokyo, Jan. 14, 2011.

Mukai, T., et al. "Genetic-code evolution for protein synthesis with non-natural amino acids," Biochemical and Biophysical Research Communications, vol. 411, 2011, pp. 757-761.

Sakamoto, K., et al. "Genetic Encoding of 3-Iodo-L-Tyrosine in *Escherichia coli* for Single-Wavelength Anomalous Dispersion Phasing in Protein Crystallography," Structure, vol. 17, Mar. 11, 2009, pp. 335-344.

Shimizu, Y., et al., "Cell-free translation reconstituted with purified components," Nat. Biotechnol., vol. 19, Aug. 2001, pp. 751-755.

Short, III, G.F., et al., "Effects of Release Factor 1 on in Vitro Protein Translation and the Elaboration of Proteins Containing Unnatural Amino Acids," Biochemistry (1999), 38, No. 27, pp. 8808-8819.

Wang, H.H., "Programming cells by multiplex genome engineering and accelerated evolution," Nature, vol. 460, Aug. 13, 2009, pp. 894-898.

Wang, L., et al., "A general approach for the generation of orthogonal tRNAs", Chemistry & Biology 8 (2001), pp. 883-890.

Wang, L., et al., "Addition of the keto functional group to the genetic code of *Escherichia coli*," PNAS, vol. 100, No. 1, Jan. 7, 2003, pp. 56-61.

Web page of "Synthetic Biology Projects . . . ", browsed Jan. 8, 2013, <http://arep.med.harvard.edu/SBP/>.

Yanagisawa, T., et al., "Multistep Engineering of Pyrrolysyl-tRNA Synthetase to Genetically Encode . . . ", Chemistry & Biology, vol. 15, Nov. 24, 2008, pp. 1187-1197.

Zubay, G., et al., "In Vitro Synthesis of Protein in Microbial Systems," 1973, pp. 267-287.

Kobayashi, K., et al., "Essential Bacillus subtilis genes," PNAS, Apr. 15, 2003, vol. 100, No. 8, pp. 4678-4683.

Liu, C.C., et al., "Adding New Chemistries to the Genetic Code," Annu. Rev. Biochem., vol. 79, 2010, pp. 413-444.

Liu, C.C., et al., "Recombinant expression of selectively sulfated proteins in *Escherichia coli*," Nature Biotechnology, vol. 24, No. 11, Nov. 2006, pp. 1436-1440.

Motohashi, T., et al., "Efficient large-scale protein production of larvae and pupae of silkworm by Bombyx mori nuclear polyhedrosis virus bacmid system," Biochemical and Biophysical Research Communications, 326 (2005) pp. 564-569.

Mukai, T., "A study on the genetic code . . .", Doctor Thesis Presentation, the University of Tokyo, Jan. 14, 2011.

Mukai, T., et al., "Condon reassignment in the *Escherichia coli* genetic code," Nucleic Acids Research, vol. 38, No. 22, 2010, pp. 8188-8195.

Mukai, T et al. "Genetic-code evolution for protein synthesis with non-natural amino acids," Biochemical and Biophysical Research Communications, vol. 411, 2011, pp. 757-761.

Neumann, H., et al., "A Method for Genetically Installing Site-Specific Acetylation in Recombinant Histones Defines the Effects of H3 K56 Acetylation," Mol. Cell. vol. 36, Oct. 9, 2009, pp. 153-163.

Ohtake, K, et al., "Efficient Decoding of the UAG Triplet as a Full-Fledged Sense Codon Enhances the Growth of a prfA-Deficient Strain of *Escherichia coli*," Journals of Bacteriology, vol. 194, No. 10, May 2012, pp. 2606-2613.

Pratt, J.M., et al., "Coupled Transcription-Translation in Prokaryotic Cell-Free Systems," pp. 179-209 (1984).

Ryden, S.M., et al., "A Temperature-Sensitive Mutant of *Escherichia coli* that Shows Enhanced Misreading of UAG/A and Increased Efficiency for Some tRNA Nonsense Suppressors," Mol. Gen. Genet (1984) 193, No. 1, pp. 38-45.

MEKKITGYTXVDISQWHRKEHFEAFQSVAQCTYNXTVXLDITAFLKTVKKNKH
KFYPAFIHILARLMNAHPEFRMAMKDGELVIWDSVHPCYTVFHEQTETFSSLW
SEYHDDFRQFLHIYSQDVACYGENLAYFPKGFIENMFFVSANPWVSFTSFDLN
VANMDNFFAPVFTMGKYYTQGDKVLMPLAIQVHHAVCDGFHVGRMLNELQQYC
DEWQGGA (b)

MEKKITGYTTVDISXWHRKEHFEAFXSVAXCTYNXTVXLDITAFLKTVKKNKH
KFYPAFIHILARLMNAHPEFRMAMKDGELVIWDSVHPCYTVFHEXTETFSSLW
SEYHDDFRXFLHIYSXDVACYGENLAYFPKGFIENMFFVSANPWVSFTSFDLN
VANMDNFFAPVFTMGKYYTXGDKVLMPLAIXVHHAVCDGFHVGRMLNELQQYC
DEWQGGA (c)

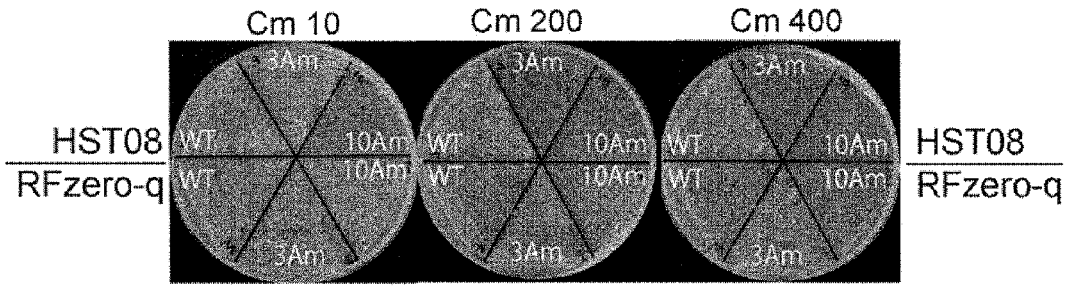

FIG. 16
(a)
(b)
+ iodoTyrRS-*mj* (D286R)
+ Nap3

FIG. 25

METHOD FOR CONSTRUCTING RECOMBINANT BACTERIUM FOR PRODUCING NON-NATIVE PROTEIN, AND UTILIZATION OF SAME

CROSS REFERENCE TO RELATED APPLICATIONS

The present application is a Section 371 U.S. national stage entry of pending International Patent Application No. PCT/JP2011/063778, International Filing Date Jun. 16, 2011, which published on Dec. 22, 2011 as Publication No. WO 2011/158895A1, which claims the benefit of Japanese Patent Application No. 2010-137635, filed Jun. 16, 2010, and which claims the benefit of Japanese Patent Application No. 2011-047663, filed Mar. 4, 2011, the contents of which are incorporated by reference in their entireties.

TECHNICAL FIELD

The present invention relates to (i) a method for producing a recombinant bacterium for production of a non-natural protein, (ii) a DNA construct for producing a recombinant bacterium for production of a non-natural protein, (iii) a recombinant bacterium for production of a non-natural protein, (iv) a method for producing a non-natural protein by using a recombinant bacterium and (v) an extract of a recombinant bacterium for production of a non-natural protein. In particular, the present invention relates to (i) a method for producing a recombinant bacterium in which a gene coding for a release factor which terminates translation at a UAG codon is defective, (ii) a DNA construct for causing the gene to be defective, (iii) a recombinant bacterium in which the gene is defective, (iv) a method for producing a non-natural protein using a recombinant bacterium in which the gene is defective and (v) an extract of a recombinant bacterium in which the gene is defective.

BACKGROUND ART

There has been a protein in which an amino acid residue at a desired position is substituted with a non-natural amino acid and/or an α-hydroxy acid, and such protein is called a non-natural protein (or super protein). The non-natural protein has a new biological activity, catalytic activity, structure and function, which are not found in natural proteins. Because of these features, non-natural protein synthesis is an indispensable basic technology for overcoming limitations of conventional protein engineering.

In recent years, it has become possible to synthesize a non-natural protein by using *Escherichia coli*, yeast, insect cells, and mammalian cells. Usually, a non-natural amino acid is introduced at an amber codon (UAG codon) (which is one of stop codons), because it is not desirable that a non-natural amino acid be introduced at a non-specific position in such a synthesizing system.

It is known that the introduction of a non-natural amino acid at an amber codon competes with release factor, which terminates translation at a UAG codon. Non-Patent Literatures 1 and 2 disclose that weakening RF-1 activity (which is a release factor for *Escherichia coli*) improves introduction efficiency for a non-natural amino acid. Furthermore, Non-Patent Literature 3 discloses that decreasing the amount of RF-1 in cell-free protein synthesis system enables efficient introduction of a non-natural amino acid at an amber codon.

Furthermore, it is considered that introduction efficiency can be further improved by causing a prfA gene coding for RF-1 to be defective. As one method for causing the prfA gene to be defective, Non-Patent Literature 4 discloses a method including replacing amber codons of all genes on a genome with ocher codons or opal codons. Non-Patent Literatures 5 and 6 report *Escherichia coli* in which a prfA gene is caused to be defective by replacing all amber codons with ocher codons.

CITATION LIST

Patent Literature

Patent Literature 1

Specification of the United States Patent Application No. 2009/0317910

Non-Patent Literatures

Non-Patent Literature 1

Ryden, S. M., and Isaksson, L. A., Molecular and General Genetics, 193, 38-45 (1984)

Non-Patent Literature 2

Kleina, L. G., et al., Journal of Molecular Biology, 213, 705-717 (1990)

Non-Patent Literature 3

Short III, G. F., et al., Biochemistry, 38, 8808-8819 (1999)

Non-Patent Literature 4

Forster, A. C. et al., Genome Research, 17, 1-6 (2007)

Non-Patent Literature 5

Wang, H. H., et al., Nature, 460, 894-898 (2009)

Non-Patent Literature 6

"Synthetic Biology Projects", [online], [browsing date: Apr. 30, 2009], Internet <URL:http://arep.med.harvard.edu/SBP/>

SUMMARY OF INVENTION

Technical Problem

There are needs for mutants of various bacteria, in which mutants genes coding for release factors of various bacteria are defective, however the conventional technologies have a problem in that it takes time and effort to produce such mutants with the conventional technologies. For example, the *Escherichia coli* disclosed in Patent Literatures 5 or 6 has a low versatility as *Escherichia coli* for use for a non-natural amino acid-introduced protein. Therefore, prfA-defective mutants having higher versatility than the *Escherichia coli* have greater demands. However, in a case where such mutants are produced by using the technology disclosed in Non-Patent Literature 4, it is necessary to replace all amber codons (314 amber codons) of genes on a genome. Thus, this technology is not preferable as a non-natural protein synthesizing system because this technology is time-consuming and troublesome.

In view of the above problems, a main object of the present invention is to provide a novel method for producing a recombinant bacterium for production of a non-natural protein, which recombinant bacterium is suitably applicable when a non-natural protein is produced by causing a gene coding for a release factor of the bacterium to be defective.

Solution to Problem

The present invention includes the following preferable aspects.

(Aspect 1)

According to the first aspect, the present invention is a method of producing a recombinant bacterium for production of a non-natural protein, including the steps of:

(1) expressing tRNA in a bacterium, which tRNA recognizes UAG codon;

(2) expressing an aminoacyl-tRNA synthetase in a bacterium, which aminoacyl-tRNA synthetase acylates the tRNA with a non-natural amino acid or an α-hydroxy acid;

(3) subjecting a bacterium to a process for expressing, in the absence of a release factor for terminating translation at UAG codon, a function of at least one gene selected from the group consisting of genes each of which loses its function when a gene that codes for the release factor is defective; and (4) causing the gene that codes for the release factor in a bacterium to be defective, the bacteria in the steps (1) through (4) being identical, and the process being (i) a process of introducing, into the bacterium, a DNA construct for expressing the function of said at least one gene in the absence of the release factor and/or (ii) a process of introducing, into said at least one gene in a chromosome of the bacterium, an alteration for expressing the function of said at least one gene in the absence of the release factor.

(Aspect 2)

As another method according to the first aspect, the present invention is a method of producing a recombinant bacterium for production of a non-natural protein, including the steps of:

(5) expressing, in a bacterium which expresses tRNA that recognizes UAG codon, an aminoacyl-tRNA synthetase that acylates the tRNA with a non-natural amino acid or an α-hydroxy acid;

(6) subjecting the bacterium to the bacterium, a process for expressing, in the absence of a release factor for terminating translation at UAG codon, a function of at least one gene selected from the group consisting of genes each of which loses its function when a gene that codes for the release factor is defective; and (7) causing the gene that codes for the release factor in the bacterium to be defective, the process being (i) a process of introducing, into the bacterium, a DNA construct for expressing the function of said at least one gene in the absence of the release factor and/or (ii) a process of introducing, into said at least one gene in a chromosome of the bacterium, an alteration for expressing the function of said at least one gene in the absence of the release factor.

(Aspect 15)

According to the second aspect, the present invention includes a DNA construct for producing a recombinant bacterium for production of a non-natural protein, which DNA construct expresses, in the presence of (i) tRNA that recognizes UAG codon and (ii) an aminoacyl-tRNA synthetase which acylates the tRNA with a non-natural amino acid or an α-hydroxy acid but in the absence of a release factor for terminating translation at UAG codon, a function of at least one gene selected from all genes each of which loses its function when a gene that codes for the release factor is defective.

(Aspect 16)

According to the third aspect, the present invention is a recombinant bacterium for production of a non-natural protein, which recombinant bacterium expresses tRNA that recognizes UAG codon; which recombinant bacterium expresses an aminoacyl-tRNA synthetase which acylates the tRNA with a non-natural amino acid or an α-hydroxy acid; (i) into which recombinant bacterium a DNA construct has been introduced, which DNA construct is for expressing, in the absence of a release factor for terminating translation at UAG codon, a function of at least one gene selected from the group consisting of genes each of which loses its function when a gene that codes for the release factor is defective and/or (ii) in which recombinant bacterium, an alteration has been introduced into said at least one gene in a chromosome of the recombinant bacterium, which alteration is for expressing the function of said at least one gene in the absence of the release factor; and in which recombinant bacterium the gene that codes for the release factor is defective.

(Aspect 18)

According to the fourth aspect, the present invention is a method of producing a non-natural protein with use of a recombinant bacterium, including expressing, in a recombinant bacterium set forth in claim 16 or in an extract of the recombinant bacterium, (a) an aminoacyl-tRNA synthetase capable of activating a non-natural amino acid or an α-hydroxy acid, (b) tRNA which recognizes UAG codon and is capable of being attached to the non-natural amino acid or the α-hydroxy acid in the presence of the aminoacyl-tRNA synthetase, and (c) a gene that codes for a desired protein, which gene has at least one nonsense mutation occurred randomly or in a desired position.

(Aspect 20)

According to the fifth aspect, the present invention is an extract of a recombinant bacterium for use in production of a non-natural protein, which recombinant bacterium expresses tRNA that recognizes UAG codon; which recombinant bacterium expresses an aminoacyl-tRNA synthetase which acylates the tRNA with a non-natural amino acid or an α-hydroxy acid; (i) into which recombinant bacterium a DNA construct has been introduced, which DNA construct is for expressing, in the absence of a release factor for terminating translation at UAG codon, a function of at least one gene selected from the group consisting of genes each of which loses its function when a gene that codes for the release factor is defective and/or (ii) in which recombinant bacterium, an alteration has been introduced into said at least one gene in a chromosome of the recombinant bacterium, which alteration is for expressing the function of said at least one gene in the absence of the release factor; and in which recombinant bacterium the gene that codes for the release factor is defective.

Advantageous Effects of Invention

According to the present invention, it is possible to easily produce a recombinant bacterium for production of a non-natural protein, even in a case where a gene that codes for a release factor of a bacterium is caused to be defective. This makes it possible to easily improve efficiency of non-natural protein production using a desired bacterium or *Escherichia coli*.

BRIEF DESCRIPTION OF DRAWINGS

FIG. 1 is a view illustrating amber codon translation carried out in a prfA-defective strain.

FIG. 2 is a view illustrating growth ability of a prfA-defective strain in which BAC7 was introduced.

FIG. 3 is a view illustrating a gene locus of BAC7.

FIG. 4 is a view illustrating defect of prfA gene.

FIG. 5

FIG. 5 (SEQ ID NOS:17 and 18) is a view illustrating introduction of glutamic acid at amber codons.

FIG. 6 is a view illustrating growth rates of *Escherichia coli* for production of a non-natural protein.

FIG. 7 (SEQ ID NOS:19-23) is a view illustrating introduction of a non-natural amino acid at amber codons.

FIG. 8 (SED ID NOS:24-27) is a view illustrating a result of mass spectrometric analyses of proteins in which glutamic acid or tyrosine was introduced.

FIG. 9 is a view illustrating introduction of azidophenylalanine at an amber codon.

FIG. 10 is a view illustrating defect of prfA gene in *Escherichia coli* in which BAC6 was introduced.

FIG. 11 is a view illustrating defect of prfA gene in *Escherichia coli* in which BAC3 was introduced.

FIG. 12 is a view illustrating defect of prfA gene in HMS174(DE3).

FIG. 13 is a view illustrating a gene locus of BAC8.

FIG. 14 is a view illustrating defect of prfA gene.

FIG. 15 is a view illustrating growth of *Escherichia coli* for production of a non-natural protein whose UAG triplet was reassigned to 4-azidophenylalanine or O-sulfotyrosine.

FIG. 16

FIG. 16 is a view illustrating growth of *Escherichia coli* for production of a non-natural protein in which a Nap3 expression system was introduced.

FIG. 17 is a view illustrating growth rates of *E. coli* lines with sucB gene overexpression system and with iodoTyrRS-mj(D286R)/Nap 3 overexpression system, in a RFzero-iy strain derived from HST08.

FIG. 18 is a view illustrating growth rates of *Escherichia coli* lines with sucB gene overexpression system and with iodoTyrRS-mj(D286R)/Nap 3 overexpression system, in a RFzero-iy strain derived from BW25113.

FIG. 19 is a view illustrating introduction of 3-iodo-L-tyrosine at an amber codon in a RFzero-iy strain derived from BW25113.

FIG. 20 is a view illustrating introduction of 3-iodo-L-tyrosine at an amber codon in a RFzero-iy strain derived from a BW25113.

FIG. 21 is a view illustrating an alteration of a supE tRNA molecule. (a) of FIG. 21 shows a 2-dimensional structure of the supE tRNA molecule before the alteration. Nucleotides enclosed by squares are nucleotides that were to be randomized. (b) of FIG. 21 is a schematic view illustrating how three oligomers producing an altered supE tRNA molecule are annealed. (c) of FIG. 21 is a view illustrating frequency of nucleotides appeared at the randomized moieties.

FIG. 22 is a view illustrating introduction of glutamine at an amber codon in *E. coli* in which the mutant supE tRNA molecule was introduced.

FIG. 23 is a view illustrating growth of *E. coli* in which the mutant supE tRNA molecule was introduced, wherein (a) to (c) of FIG. 23 each illustrate growth under different conditions.

FIG. 24 is a view illustrating growth rates of RFzero-iy strains derived from BW25113, HMS174(DE3) and BL21 (DE3).

FIG. 25

FIG. 25 is a view illustrating growth rates of RFzero-iy strains with or without corresponding non-natural amino acids, the RFzero-iy strains being derived from BW25113, HMS174(DE3) and BL21(DE3).

FIG. 26 shows structures of various non-natural amino acids.

FIG. 27 is a view illustrating growth rates of a BW25113RFzero-iy strain whose UAG codon was reassigned to a non-natural amino acid other than 3-iodo-L-tyrosine.

FIG. 28 is a view illustrating growth rates of BW25113RFzero-iy strains in which UAG codon thereof was reassigned to a non-natural amino acid other than 3-iodo-L-tyrosine, in the presence or absence of their corresponding non-natural amino acids.

FIG. 29 shows introduction of 3-iodo-L-tyrosine or another non-natural amino acid at an amber codon in (i) a BW25113RFzero-iy strain, and (ii) strains whose UAG codons were reassigned to non-natural amino acids other than 3-iodo-L-tyrosine.

FIG. 30 is a view illustrating a result of a mass spectrometric analysis confirming introduction of 3-iodo-L-tyrosine.

FIG. 31 is a view illustrating introduction efficiency of a non-natural amino acid at an amber codon in a prfA+ strain.

FIG. 32 shows a result of a mass spectrometric analysis confirming introduction of acetyllysine into H4 histone.

DESCRIPTION OF EMBODIMENTS

Figure 1:
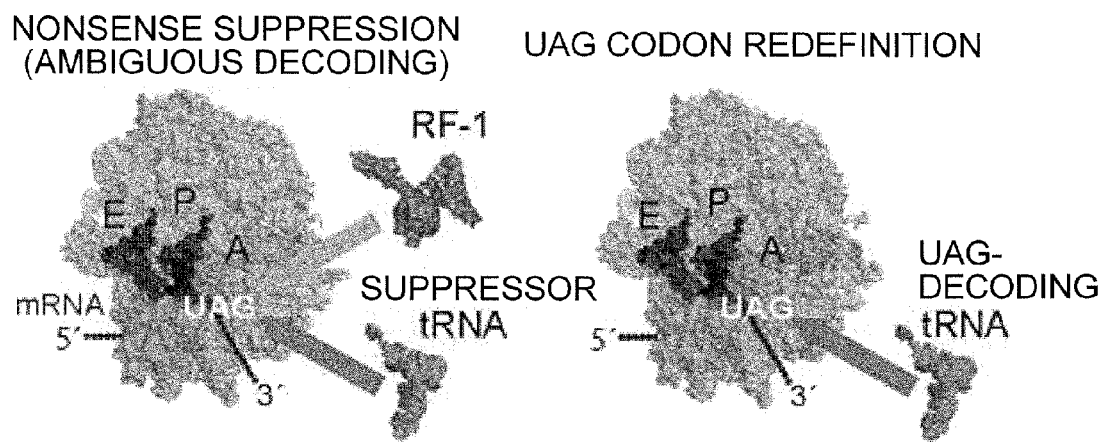
FIG. 1

[Production of Recombinant Bacterium for Production of Non-natural Protein]

A method of producing a recombinant bacterium in accordance with the present invention can be arranged to be (A) a method of producing a recombinant bacterium for production of a non-natural protein, including the steps of:

(1) expressing tRNA in a bacterium, which tRNA recognizes UAG codon;

(2) expressing an aminoacyl-tRNA synthetase in a bacterium, which aminoacyl-tRNA synthetase acylates the tRNA with a non-natural amino acid or an α-hydroxy acid;

(3) subjecting a bacterium to a process for expressing, in the absence of a release factor for terminating translation at UAG codon, a function of at least one gene selected from the group consisting of genes each of which loses its function when a gene that codes for the release factor is defective; and (4) causing the gene that codes for the release factor in a bacterium to be defective, the bacteria in the steps (1) through (4) being identical, and the process being (i) a process of introducing, into the bacterium, a DNA construct for expressing the function of said at least one gene in the absence of the release factor and/or (ii) a process of introducing, into said at least one gene in a chromosome of the bacterium, an alteration for expressing the function of said at least one gene in the absence of the release factor, or (B) a method of producing a recombinant bacterium for production of a non-natural protein, including the steps of:

(5) expressing, in a bacterium which expresses tRNA that recognizes UAG codon, an aminoacyl-tRNA synthetase that acylates the tRNA with a non-natural amino acid or an α-hydroxy acid;

(6) subjecting the bacterium to a process for expressing, in the absence of a release factor for terminating translation at UAG codon, a function of at least one gene selected from the group consisting of genes each of which loses its function when a gene that codes for the release factor is defective; and (7) causing the gene that codes for the release factor in the bacterium to be defective, the process being (i) a process of introducing, into the bacterium, a DNA construct for expressing the function of said at least one gene in the absence of the release factor and/or (ii) a process of introducing, into said at least one gene in a chromosome of the bacterium, an alteration for expressing the function of said at least one gene in the absence of the release factor.

Each of the steps (3) and (6) may further include a process for expressing, in the absence of the release factor for terminating translation at a UAG codon, a function of a gene that is known to (i) lose its function when a gene that codes for the release factor is defective and (ii) thereby reduce the growth rate of the bacterium.

In a case where the method of producing a recombinant bacterium for production of a non-natural protein in accordance with the present invention includes (1) the step of expressing tRNA in a bacterium, which tRNA recognizes UAG and (2) the step of expressing an aminoacyl-tRNA synthetase in the bacterium, which aminoacyl-tRNA synthetase acylates the tRNA with a non-natural amino acid or an α-hydroxy acid, the bacterium can be a bacterium in which another tRNA that recognizes UAG has already been expressed. For example, the method can be arranged to express, in *Escherichia coli* in which tRNA derived from *Escherichia coli* and recognizes UAG is expressed, (i) archaeal tRNA that recognizes UAG and (ii) an aminoacyl-tRNA synthetase which acylates the archaeal tRNA with a non-natural amino acid (described later in detail).

In a case where the bacterium which is subjected to the processes of the steps (1) to (4) or of the steps (5) to (7) is a bacterium in which UAG codon-recognizing tRNA which is not acylated by the aminoacyl-tRNA synthetase introduced in the step (2) or the step (5) is expressed, it is preferable that a gene that codes for the tRNA is defective. For example, in a case where (i) archaeal tRNA is expressed in *Escherichia coli* in which endogenous amber suppressor tRNA is expressed and (ii) an archaeal aminoacyl-tRNA synthetase (which cannot acylate tRNA of *Escherichia coli*) which acylates the archaeal tRNA is introduced into the *Escherichia coli*, it is preferable that a gene that codes for the endogenous amber suppressor tRNA of *Escherichia coli* is defective (described later in detail). By causing this gene to be defective, it is possible to avoid competition for the UAG codon with tRNA acylated with a desired non-amino acid etc., and thus possible to efficiently introduce the non-amino acid etc. into a protein. The step of causing this gene to be defective can be carried out in any stage independently or concurrently with any of the steps (1) to (4) or the steps (5) to (7).

In a case where (i) an aminoacyl-tRNA synthetase which acylates, with a non-natural amino acid etc., endogenous tRNA which recognizes UAG is introduced into a bacterium in which the tRNA is expressed and (ii) the bacterium is a bacterium in which an endogenous aminoacyl-tRNA synthetase which acylates the tRNA with a natural amino acid is expressed, it is preferable that a gene that codes for the aminoacyl-tRNA synthetase for attaching the natural amino acid is defective. By causing this gene to be defective, it is possible to avoid competition for the UAG codon with tRNA acylated with a desired non-natural amino acid etc., and thus possible to efficiently introduce the non-natural amino acid etc. into a protein.

The order in which the steps (1) to (4) are carried out is not particularly limited, and for example the step (1) and the step (2) can be carried out concurrently. Note however that, in view of the efficiency of causing the gene that codes for the release factor to be defective, it is preferable to carry out the step (1) and the step (2) before the step (4). It is particularly preferable to carry out the step (3) and the step (4) in this order after carrying out the step (1) and the step (2).

Similarly, the order in which the steps (5) to (7) are carried out is not particularly limited. Note however that, in view of the efficiency of causing the gene which codes for the release factor to be defective, it is preferable to carry out the step (5) before the step (7). It is particularly preferable to carry out the step (5), the step (6) and the step (7) in this order In this Description, a tRNA recognizing an UAG codon is also referred to as an "amber suppressor tRNA". This tRNA can be acylated with a non-natural amino acid or an α-hydroxy acid.

In this Description, the term "non-natural protein" means a protein other than proteins produced from natural amino acids alone. As non-natural proteins, for example, non-natural proteins including a non-natural amino acid or an α-hydroxy acid can be exemplified.

Furthermore, the term "non-natural amino acid" means an amino acid other than 20 standard amino acids utilized universally by living things. For example, non-natural amino acids encompass, but not limited to, lysine and tyrosine derivatives. In this Description, the non-natural amino acids also encompass modified standard amino acids modified, for example, by phosphorylation.

Herein, the lysine derivatives are preferably lysine derivatives in which a hydrogen atom bonded to a nitrogen atom at position ε is substituted with another atom or an atomic group. Such lysine derivatives include, for example, pyrrolidine, Nε-t-butoxycarbonyllysine (Boc-Lys), Nε-acetyllysine, Nε-t-benzyloxycarbonyllysine (Z-Lys) and Nε-(o-azidobenzyloxycarbonyl) lysine (azidoZ-Lys). In addition to amino acids, lysine derivatives including an α-hydroxy acid, i.e., a BocLysOH whose amino group of a Boc-Lysine main chain is substituted with a hydroxy group are encompassed in the lysine derivatives.

The tyrosine derivatives include position 3-substituted tyrosine and position 4-substituted tyrosine each of which has a substituent at position 3 or position 4 of a phenyl group thereof, and O-modified tyrosine in which an oxygen atom of tyrosine is substituted. The position 3-substituted tyrosine includes 3-iodo-L-tyrosine, 3-bromo-L-tyrosine, 3-chloro-L-tyrosine, 3-azido-L-tyrosine and 3-hydroxy-L-tyrosine. The position 4-substituted tyrosine include 4-acetyl-L-phenylalanine, 4-benzoyl-L-phenylalanine and 4-azido-L-phenylalanine. The O-modified tyrosine includes O-sulfotyrosine. Hereinafter, 3-iodo-L-tyrosine, 3-bromo-L-tyrosine and 3-chloro-L-tyrosine are referred to as simply 3-iodotyrosine, 3-bromotyrosine and 3-chlorotyrosine respectively.

A release factor is also referred to as a termination factor or a polypeptide chain termination factor. The release factor recognizes a stop codon on mRNA and causes release of a polypeptide chain from a ribosome. A release factor for terminating translation at a UAG codon (hereinafter, also simply referred to as a "release factor recognizing UAG) is RF-1 in bacteria such as *Escherichia coli*, hay *bacillus* (*Bacillus subtilis*) and the like. Genes coding for the release factor recognizing UAG (Hereinafter, also simply referred to as "UAG-recognizing release factor genes" include a prfA gene and the like in *Escherichia coli*, which prfA gene is consisting of the nucleic acid sequence shown in SEQ ID NO: 1.

In this Description, "defect of a gene coding for a release factor for terminating translation at a UAG codon" is intended to include cases where the gene does not exist in a cell, most part of ORF of the gene is lacking, an essential part of the gene is lacking, the gene is not expressed, and the gene includes a mutation and therefore inhibits the function of the release factor (e.g., the release factor cannot recognize UAG codon).

The defect of the UAG-recognizing release factor gene can be caused by using a known method for a gene disruption such as a method utilizing a genetic homologous recombination. In particular, Red/ET Recombination SystemQuick and Easy BAC MODIFICATION Kit (Gene Bridges GmbH, Germany) are preferable to use. Here, it is preferable, in view of efficiency of causing the UAG-recognizing release factor gene to be defective, to cause the UAG-recognizing release factor gene to be defective after bacterium transformation to express an amber suppressor tRNA.

In this Description, the wording "cause loss of a function when a gene that codes for a release factor for terminating translation at UAG codon is defective" is intended, regarding the function of the certain gene, to include cases where the function is completely lost by defect of the UAG-recognizing release factor genes, a part of the function is lost, the function is inhibited, and the function is deteriorated. One possible example of mechanisms via which a gene loses its function because of defect of the UAG-recognizing release factor gene, is one in which a protein function is inhibited because a UAG codon fails to terminate translation, so that an additional peptide(s) is added to a C terminal. Another possible example of the mechanisms is one in which translation for a gene downstream of the gene on a chromosome is not carried out appropriately because a UAG codon fails to terminate translation, so that the protein function of the downstream gene is inhibited. It should be noted that the mechanisms of defect of the function are not limited to the above examples.

In this Description, the wording "a gene which loses its function when a gene that codes for a release factor for terminating translation at UAG codon is defective" is intended to mean a gene whose stop codon is a UAG codon and which loses a function because of defect of the definition of the UAG-recognizing release factor gene, and also intended to be a gene which (i) is located, in a chromosome, downstream of another gene whose stop codon is a UAG codon and (ii) is not properly translated when translation of the another gene whose stop codon is the UAG codon is not terminated properly.

In this Description, the wording "expressing a function of a gene" is intended to mean to cause the gene to be translated to a protein which functions normally. Therefore, "expressing a function of a gene in the absence of a release factor for terminating translation by a UAG codon, the gene losing the function when a gene coding for the release factor is defective" means expressing a normal protein of a gene in the absence of a release factor recognizing UAG, the gene losing the function when the release factor gene is defective.

Any bacteria are usable for the present invention as long as an exogenous gene can be introduced into the bacteria or the bacteria can be genetically altered. Note that the present invention is achieved based on the finding made by the inventors of the present invention that *Escherichia coli* in which prfA gene is defective becomes able to grow when a gene, defect of which alone is lethal, is expressed among all genes whose translation is terminated at a UAG codon. It is considered that, this is not applicable only to *Escherichia coli*, but to other cases, so that, even in a case where a gene coding for the release factor for terminating translation at a UAG codon is defective, others can become able to grow when a gene defect of which alone is lethal is expressed among all genes whose translation is terminated at a UAG codon. Therefore, the bacteria to which the present invention is applicable are not limited to *Escherichia coli*, but also include other bacteria such as hay *bacillus* (*Bacillus subtilis*) and the like.

In this Description, the wording "DNA construct" is intended to mean a DNA construct having a form capable of being introduced into bacteria, and being self-replicable intracellularly, or capable of being integrated into a cellular chromosome. The DNA construct can be in the forms of a bacterial artificial chromosome (BAC), a plasmid and a straight chain DNA.

In a case where an HST08 strain of *Escherichia coli* is used as a bacterium to transform and BAC is used as a DNA construct, it is preferable to use BAC having miniF replicon as the BAC. On the other hand, in a case where *Escherichia coli* having an F plasmid is selected as a bacterium to transform, it is preferable to prepare the BAC by introducing a gene into a plasmid having another origin, such as, a ColibP9 origin.

The DNA construct is intended to be recruited (introduced) in trans and/or in cis into a bacterial chromosome. In this Description, the wording "be recruited (introduced) in trans into a bacterial chromosome" means the DNA construct is introduced into a bacterial cell but not integrated into the bacterial chromosome. On the other hand, in this Description, "be recruited (introduced) in cis into a bacterial chromosome" means the DNA construct is introduced into the bacterial cell and also integrated into the bacterial chromosome.

What is meant in more specific sense by "a DNA construct for expressing, in the absence of a release factor for terminating translation at a UAG codon, a function of a gene which loses its function when a gene that codes for the release factor is defective" is a DNA construct including an altered gene whose stop codon of a gene which loses the function when a UAG-recognizing release factor gene is defective is changed to ocher codons (UAA) or opal codons (UGA) from amber codons (UAG). By having a codon other than the amber codon as the stop codon, it is possible to terminate the translation at an intended position, even in the absence of the release factor recognizing UAG, so that it becomes possible to produce proteins which are coded for by these genes and function normally. The introduction of the DNA construct into a cell makes it possible to express, even in the absence of the release factor recognizing UAG, the function of the gene which loses the function when the UAG-recognizing release factor genes are defective.

For example, at first, by utilizing a known genetic recombination technology, a subject gene or an operon including the gene is cloned from a bacterium. Then, the gene is mutated to change a stop codon of the gene to UAA or UGA from UAG by using PCR or the like. Then, by introducing the mutated genes or operons into a BAC or a plasmid, it is possible to produce a desired DNA construct. Alternatively, it is also possible to produce a straight-chain DNA by connecting these genes and operons.

In addition, it is also possible to produce a fragment by ligating a plurality of operons by using an overlap PCR method using PrimeStar GXL (TaKaRa) or the like, and then introduce the fragment into a BAC plasmid. In order to produce a fragment of less than 20 kbp, it is preferable to use an HST08 strain (TaKaRa). On the other hand, in order to produce a fragment of 20 kbp or more, Res/ET Recombination SystemQuick and Easy BAC MODIFICATION Kit (Gene Bridges GmbH, Germany) are preferable to use.

In a case where the DNA construct is introduced into a bacterial chromosome, it can be introduced in trans into the bacterial chromosome or it also can be introduced in cis into the bacterial chromosome. In other words, it is possible to configure such that a gene is expressed from the DNA construct in which the gene is integrated, or that the gene is expressed from an *E. coli* chromosome with the gene knocked therein. The knocking in the gene in the *Escherichia coli* chromosome may be carried out by a known method.

What is meant in more specific sense by "introduction of an alteration for expressing, in the absence of a release factor for terminating translation at a UAG codon, a function of a gene which loses its function when a gene that codes for the release factor is defective" is introduction of such alteration that a stop codon of the gene which loses the function when the UAG-recognizing release factor gene is defective is changed to ocher codon (UAA) or opal codon (UGA) from amber codon (UAG). By causing all stop codons on bacterial chromosome to be the codons other than amber codon, it is possible to terminate translation at an intended position even in the absence of the release factor recognizing UAG, so that it becomes possible to produce proteins which are coded for by these genes and function normally. Therefore, by introducing such alteration into a bacterial chromosome, it is possible to express, even in the absence of the release factor recognizing UAG, the function of the gene which loses the function when the UAG-recognizing release factor gene is defective.

The introduction of the alteration at the stop codon of a gene on a chromosome may be carried out by a known method. For example, methods using a genetic homologous recombination or selecting a corresponding mutation from mutations occurring at random on bacterial chromosome can be used.

It is also possible to employ in combination the methods of (i) introducing a gene in trans and expressing the gene, (ii) introducing a gene in cis and expressing the gene, and (iii) altering an amber codon of a gene in a chromosome and expressing the gene. For example, in a case where functions of seven genes are to be expressed, it can be possible to express the functions of seven genes by introducing six of the seven genes into a bacterial cell by using the DNA construct and, for the remaining one of the seven genes, by altering an amber codon of the gene on the chromosome.

Some of the genes which lose the functions when UAG-recognizing release factor genes are defective would be such genes defect of any one of which alone is lethal. Accordingly, a bacterium would unlikely grow when such a genetic function is lost due to the absence of the UAG-recognizing release factor gene. Therefore, it is preferable that a gene defect of which alone is lethal is included in the genes which express the functions even in the absence of the UAG-recognizing release factor gene, i.e., in one or more genes selected from the group consisting of all genes which cause loss of functions when the gene coding for the release factor for terminating translation at a UAG codon is defective.

Examples of such genes, whose translation is terminated at a UAG codon and defect of any one of which alone is lethal, encompass coaD, murF, hda, mreC, lpxK, hemA and lolA of *Escherichia coli*. Nucleic acid sequences of coaD, murF, hda, mreC, lpxK, hemA and lolA genes are shown in SEQ ID NOs: 2, 3, 4, 5, 6, 7 and 8, respectively. The nucleic acid sequences of these genes shown in the sequence numbers are derived from an *Escherichia coli* K-12 strain. Therefore, for other bacterial strains, their nucleic acid sequences may have nucleotide substitution. Such genes are also included the examples.

As for hay *bacillus*, examples of genes, whose translation is terminated at a UAG codon and defect of any one of which alone is lethal, encompass accD, acpS, cspR, dapB, divIC, dnaA, fmt, folD, ftsA, map, mrpD, murE, murG, plsX, ppnK, racE, resB, resC, rnpA, rplX, rpmGB, rpmH, rpsG, secA, secY, topA, trmD, yacM, ydiC, yloQ, ypuH and ysxC genes.

It is considered that, among the genes which would lose the functions when the gene coding for the release factor for terminating translation at a UAG codon is defective, the translation of mreD and hemK genes whose stop codons are not UAG codons and are downstream of UAG codons on the chromosome could be influenced unless the translation of the genes (mre C, hemA) being upstream of mreD and hemK have been appropriately terminated. Both mreD and hemK genes are essential genes. Therefore it is also preferable that these genes are included in one or more gene selected from the group consisting of all genes which lose functions when the genes coding for release factor for terminating translation at a UAG codon are defective.

In *Escherichia coli*, the gene(s) which express(es) its function even in the absence of UAG-recognizing release factor genes are preferably one or more genes selected from the group consisting of coaD, murF, hda, mreC, hemA, lpxK and lolA, more preferable to be any 6 genes of these genes, further preferable to be all these genes.

Genes, defect of whose functions is not lethal to a bacterium but cause a decrease of growth rate of the bacterium, are also included in the genes which lose functions when the UAG-recognizing release factor genes are defective. It is expected that a decrease in the growth rate of the bacterium lowers a yield of protein. Therefore, it is preferable that genes which are known for decreasing the growth rate of the bacterium when the genes lose their functions are included in one or more gene selected from all genes losing functions when the genes coding for release factor for terminating translation at a UAG codon are defective.

As for *Escherichia coli*, preferable as the genes which are known for losing functions, and consequently decreasing the growth rates of the bacteria, when a gene coding for a release factor for terminating translation at a UAG codon is defective, and which express the functions even in the absence of the UAG-recognizing release factor gene, are fliN, fliP, fliQ, sucB, ubiF, ulaF, atpE and fabH, which are described in Example 3. Among them, sucB gene is more preferable.

[Method for Producing Non-natural Protein]

A known method may be applied for the non-natural protein production. For example, it is possible to employ a method of producing a non-natural protein by expressing, in a desired bacterium or in cellular extract solution (extract) of the desired bacterium, (a) an aminoacyl-tRNA synthetase which can activate a non-natural amino acid or an α-hydroxy acid, (b) amber suppressor tRNA capable of combining with the non-natural amino acid or α-hydroxy acid in the presence of the aminoacyl-tRNA synthetase and (c) a gene coding for a desired protein having a nonsense mutation at a random or desired position. In this method, it is possible to introduce the non-natural amino acid or α-hydroxy acid into the protein by adding the non-natural amino acid or α-hydroxy acid in a medium where the bacterium is cultivated, or in the cellular extract solution. Herein, the non-natural amino acid or α-hydroxy acid to be added to the medium or the cellular extract solution is to correspond to the aminoacyl-tRNA synthetase in (a), i.e., is one that can be activated by the aminoacyl-tRNA synthetase.

Specifically, it is possible to introduce pyrrolidine into a protein by introducing pyrrolidyl-tRNA synthetase (PylRS or pylRS gene) of *Methanosarcina-mazei* or *Methanosarcina-barkeri* and tRNA$^{Pyl}$ (pylT gene) into *Escherichia coli*. It is also possible to introduce Boc-lysine and BocLysOH by introducing a H61K and Y384F mutant (BocLysRS1) for *Methanosarcina-mazei* PylRS and a K61R, E131G and Y384F mutant (BocLysRS2) for *Methanosarcina-mazei* PylRS. In a case where a Y384F and Y306A mutant (ZLysRS) for *Methanosarcina-mazei* PylRS is to be introduced, it is possible to introduce Z-lysine, 2-chloro-Z-lysine, 2-nitro-Z-lysine and 2-azido-Z-lysine. In a case where a H63Y, S193R, N203T, M300F, A302G and Y384W mutant for *Methanosarcina-mazei* PylRS is introduced, it is possible to introduce BocLysOH because the mutant recognizes specifically the BocLysOH. In a case where a N203T, L301I, L305I, Y306F, L309A and C348F mutant (AcLysRS2, not released) for *Methanosarcina-mazei* PylRS is to be introduced, it is possible to introduce acetyllysine. Furthermore, in a case where a A302F, Y306A, N346S, C348I and Y384F mutant for *Methanosarcina-mazei* PylRS is to be introduced, it is possible to introduce a 3-substituted lactic acid such as 3-(3-iodophenyl) lactic acid, 3-(3-bromophenyl) lactic acid, 3-(4-acetylphenyl) lactic acid, 3-(4-benzoylphenyl) lactic acid, 3-(4-azidophenyl) lactic acid and 3-(3-methyl-4-hydroxyphenyl) lactic acid.

Note that, it is also possible to introduce acetyllysine by introducing a PylRS mutant for *Methanosarcina-barkeri* (AcKRS-3, Neumann H et al. A method for genetically installing site-specific acetylation in recombinant histones defines the effects of H3 K56 acetylation. Chin et al., Mol. Cell. 2009 Oct. 9; 36(1):153-63). In addition, it is also possible to introduce N$_\epsilon$-allyloxycarbonyl-L-lysine (AlocLys) and N$_\epsilon$-(o-azidobenzyloxycarbonyl)-L-lysine (AzZlys) by using a PylRS mutant for *Methanosarcina-mazei* reported by Yanagisawa et al, (Yanagisawa T. et al, Chem. Biol., 15, 1187-1197 (2008)).

Furthermore, it is possible to produce a non-natural protein by introducing an aminoacyl-tRNA synthetase mutant (described below) into *Escherichia coli* and adding a corresponding non-natural amino acid to a medium.

The non-natural amino acid is 3-iodotyrosine and azidotyrosine: the aminoacyl-tRNA synthetase mutant is a H70A, D158T, I159S and D286Y mutant for iodoTyrRS-mj. (Sakamoto K, Murayama K, Oki K, Iraha F, Kato-Murayama M, Takahashi M, Ohtake K, Kobayashi T, Kuramitsu S, Shirouzu M, Yokoyama S. Genetic encoding of 3-iodo-L-tyrosine in *Escherichia coli* for single-wavelength anomalous dispersion phasing in protein crystallography. Structure. 2009 Mar. 11; 17(3): 335-44.).

The non-natural amino acid is hydroxytyrosine: The aminoacyl-tRNA synthetase mutant is a Y32L, A67S, H70N and A167Q mutant for mutDHPRS (Guo J, Wang J, Anderson J C, Schultz P G. Addition of an alpha-hydroxy acid to the genetic code of bacteria. Angew Chem Int Ed Engl. 2008; 47(4):722-5.).

The non-natural amino acid is acetylphenylalanine: the aminoacyl-tRNA synthetase mutant is a Y32L, D158G, I159C and L162R mutant for LW1 (Wang L, Zhang Z, Brock A, Schultz P G. Addition of the keto functional group to the genetic code of *Escherichia coli*. Proc Natl Acad Sci USA. 2003 Jan. 7; 100(1):56-61. Epub 2002 Dec. 23.).

The non-natural amino acid is benzylphenylalanine: the aminoacyl-tRNA synthetase mutant is a Y32G, E107S, D158T and I159S mutant for MjBpaRS-1 (Chin J W, Martin A B, King D S, Wang L, Schultz P G. Addition of a photocrosslinking amino acid to the genetic code of *Escherichia coli*. Proc Natl Acad Sci USA. 2002 Aug. 20; 99(17):11020-4. Epub 2002 August 1.)

The non-natural amino acid is azidophenylalanine: the aminoacyl-tRNA synthetase mutant is a Y32T, E107N, D158P, I159L and L162Q mutant for AzPheRS-1 (Chin J W, Santoro S W, Martin A B, King D S, Wang L, Schultz P G. Addition of p-azido-L-phenylalanine to the genetic code of *Escherichia coli*. J Am Chem. Soc. 2002 Aug. 7; 124(31):9026-7.).

[Extract of Recombinant Bacterium for Production of Non-natural Protein and Production of Non-natural Protein Using the Extract]

As a method for producing a non-natural protein, non-cell protein synthesis system can be applied as described above. For example, it is possible to produce a non-natural protein in an extract of a recombined bacterial strain, which extract was prepared according to the method disclosed in Zubay at al. (Zubay et al., Ann. Rev. Genet. Vol. 7, pp. 267-287 (1973)) Pratt at al. (Pratt, J. M. et al., Transcription and Translation—A practical approach, (1984), pp. 179-209, Henes, B. D. et al. eds., IRL Press, Oxford) or Kigawa at al. (Kigawa, T. et al, J. Struct. Funct. Genomics, Vol. 5, pp 63-68 (2004)).

Therefore, the present invention includes an extract of a recombinant bacterium for production of a non-natural protein, wherein (i) the recombinant bacterium expresses tRNA recognizing a UAG codon, (ii) the recombinant bacterium expresses an aminoacyl-tRNA synthetase for acylating the tRNA with a non-natural amino acid or α-hydroxy acid, (iii) a DNA construct for expressing, in the absence of the release factor for terminating a translation at a UAG codon, functions of one or more genes selected from group of genes which lose their functions when a gene coding for the release factor is defective is introduced and/or (iv) an alteration is introduced into the one or more gene on a bacterial chromosome, which alteration is for expressing the functions of the gene(s) in the absence of the release factor and (v) the gene coding for the release factor is defective.

The extract of the recombinant bacterium for producing a non-natural protein may be prepared by using the following preparation method. At first, a recombinant bacterium capable of generating an aminoacyl-tRNA synthetase specific to a non-natural amino acid is cultivated and the recombinant bacterium is collected by centrifugation. The collected bacterium is washed and suspended in a buffer solution and crushed by using frenchpress, glass beads or a Waring blender. Then, an insoluble fraction of the recombinant bacterium is removed by centrifugation, and a fraction other than the insoluble fraction was then incubated. This incubation enables decomposition of an endogenous nucleic acid (DNA and RNA). The endogenous nucleic acid can be further decomposed by adding calcium salt or by adding nuclease of a micrococcus. After the incubation, endogenous amino acid, nucleic acid a nucleoside and the like are removed by dialysis, thereby an extract is prepared.

Production of a non-natural protein using the extract of the recombinant bacterium may be carried out by the following method. An amber suppressor tRNA prepared in vitro, a commercially available tRNA fraction and a template DNA/RNA are added to the extract of the recombinant bacterium. Herein, a non-natural amino acid or an α-hydroxy acid suitable for the protein and the type of the preparing system is added to the extract, furthermore, energy, an ion, buffer solution, ATP regenerating system, a nucleolytic enzyme inhibitor, a reducer, polyethyleneglycol, cAMP, a folic acid, an antibacterial agent, or the like can also be added to the extract. Alternatively, in a case where a template DNA is used, it is preferable that a RNA synthesis system (a substrate, a polymerase and the like) is added to the extract.

As has been described, the present invention can also be arranged as below.

(Aspect 3)
The method of Aspect 1 or 2 can also be arranged such that, in the bacterium, another tRNA which recognizes UAG codon but is not acylated by the aminoacyl-tRNA synthetase is expressed, and said method further includes the step of causing a gene that codes for said another tRNA to be defective.

(Aspect 4)
The method of Aspect 1 or 2 is preferably arranged such that the non-natural protein is a non-natural protein that includes the non-natural amino acid or the α-hydroxy acid.

(Aspect 5)
Further, it is preferable that the bacterium is *Escherichia coli*.

(Aspect 6)
Further, it is preferable that said at least one gene is at least one, defect of which alone causes lethality in the bacterium, among all genes whose translation is terminated at UAG codon.

(Aspect 7)
Further, it is preferable that the bacterium is *Escherichia coli*, and said at least one gene is at least one gene selected from the group consisting of coaD, murF, hda, mreC, hemA, lpxK and lolA.

(Aspect 8)
Further, it is preferable that said at least one gene is any six genes selected from the group consisting of coaD, murF, hda, mreC, hemA, lpxK and lolA of *Escherichia coli*.

(Aspect 9)
Further, it is preferable that said at least one gene is coaD, hda, mreC and hemA genes of *Escherichia coli*.

(Aspect 10)
Further, it is preferable that said at least one gene further includes another gene, defect of which causes a reduction in growth rate of the bacterium.

(Aspect 11)
Further, it is preferable that said another gene defect of which causes a reduction in growth rate of the bacterium is a sucB gene of *Escherichia coli*.

(Aspect 12)
Further, it is preferable that the bacterium is *Escherichia coli* and the DNA construct is a DNA construct which expresses a function of at least one gene selected from the group consisting of coaD, murF, hda, mreC, hemA, lpxK and lolA.

(Aspect 13)
It is preferable that the DNA construct further expresses a function of a sucB gene of *Escherichia coli*.

(Aspect 14)
It is preferable that the DNA construct is selected from a bacterial artificial chromosome, a plasmid, and linear DNA, each of which is recruited in trans and/or in cis to the chromosome of the bacterium.

(Aspect 17)
It is preferable that the recombinant bacterium of Aspect 16 is derived from *Escherichia coli*.

(Aspect 19)
It is preferable that, in the method of Aspect 18, the recombinant bacterium is derived from *Escherichia coli*.

(Aspect 21)
It is preferable that, in the extract of Aspect 20, the recombinant bacterium is derived from *Escherichia coli*.

The following description discusses Examples, based on which embodiments of the present invention are described in more detail. It is needless to say that the present invention is not limited to the following Examples, and that the details can be variously arranged. Further, the present invention is not limited to the descriptions of the respective embodiments, but may be altered within the scope of the claims. An embodiment derived from a proper combination of technical means disclosed in different embodiments is encompassed in the technical scope of the invention. Furthermore, all the citations stated in the description are incorporated herein by reference.

EXAMPLES

Example 1

[Production of Conditional prfA Mutant]
In order to identify a gene(s) that is/are necessary for growth of prfA-defective *Escherichia coli*, the inventors of the subject application produced a conditional prfA mutant (refer to FIG. 1). By causing a prfA gene to be defective as shown in FIG. 1, it is possible to prevent competition with suppressor tRNA at a position of a stop codon. Note here that the conditional prfA mutant means a mutant in which expression of the prfA gene is (i) induced in the presence of L-arabinose but (ii) suppressed in the presence of D-glucose.

Figure 2:
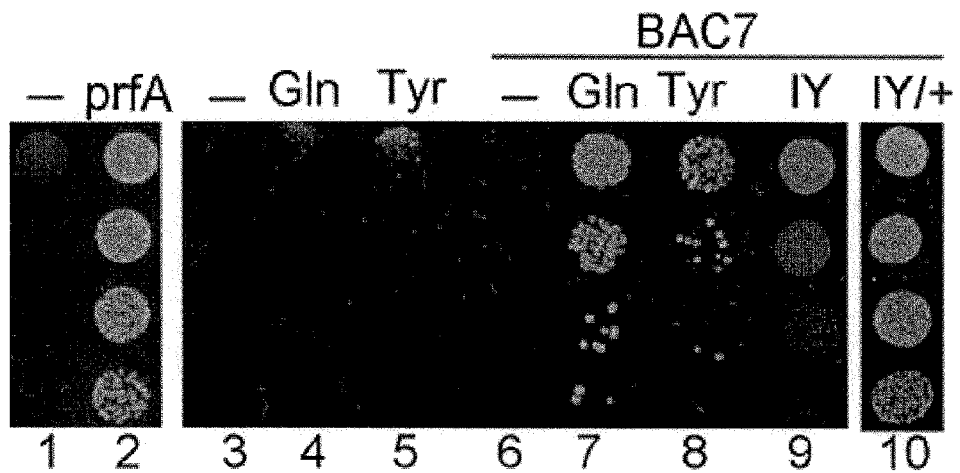
FIG. 2

How the conditional prfA mutant grows in the presence of glucose is shown in Lanes 1 and 2 of FIG. 2. As shown in Lanes 1 and 2 of FIG. 2, the conditional prfA mutant did not grow in the presence of glucose (Lane 1); however, a conditional prfA mutant into which a plasmid had been introduced, which plasmid constitutively expressed a prfA gene, grew in the presence of glucose (Lane 2).

Next, an amber suppressor tRNA$^{Gln}$ gene or an amber suppressor tRNA$^{Tyr}$ gene of *Escherichia coli* was introduced into a conditional prfA mutant so that an amber codon would be translated. However, as shown in Lane 4 (amber suppressor tRNA$^{Gln}$ was introduced) and Lane 5 (amber suppressor tRNA$^{Tyr}$ was introduced) of FIG. 2, neither of these tRNA genes supported the growth of the conditional prfA mutant in the presence of glucose. Generally, a protein with an extra C-terminal peptide(s) does not show toxicity; however, the addition of the extra peptide(s) may impair a function of the protein sometimes. For this reason, it was considered that the growth of the conditional prfA mutant into which the amber suppressor tRNA$^{Gln}$ or the amber suppressor tRNA$^{Tyr}$ had been introduced was inhibited because an extra peptide was added to the protein due to failure to terminate the translation at the amber codon.

On the basis of the above finding, the inventors of the present invention came to the following idea. That is, by replacing amber codons of seven genes (i.e., coaD, murF, hda, mreC, hemA, lpxK and lolA) of *Escherichia coli* with other stop codons, it is possible to overcome lethality in *Escherichia coli* caused by the addition of an extra peptide. The seven genes are part of all genes whose translation is terminated at a UAG codon, and defect of any one of the seven genes alone is lethal. On the basis of this idea, the inventors of the present invention produced BAC7, which is a BAC plasmid which expresses the seven genes whose amber codons have been replaced with ochre codons and/or opal codons. The following description discusses how to produce the BAC7.

[Production of BAC7 and Introduction of BAC7]

Figure 3:
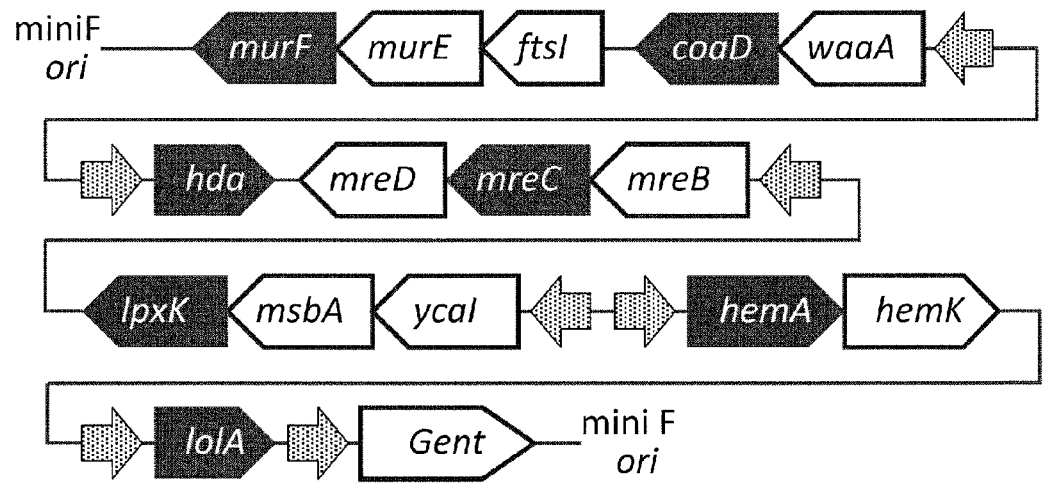
FIG. 3

First, BAC0, which is a BAC plasmid that contains a miniF replicon and a Zeocin-resistant gene, was prepared in accordance with the method disclosed in Motohashi et al. (Motohashi, T., et al., Biochem Biophys Res Commun, Vol. 326, pp. 564-569 (2005)). Then, a ftsI gene, a murE gene, a murF gene, a waaA-coaD operon, a mreB-mreC-mreD operon, a ycaI-msbA-lpxK operon, a hda gene, a hemA gene, a hemK gene, and a lolA gene were cloned from BL21 (DE3). Mutations were introduced by PCR to replace, with ochre codons (TAA), amber codons (TAG) of cloned coaD, murF, hda, mreC, lpxK, lolA and hemA genes. The operons into which the mutations had been introduced (or mutated genes) were introduced into BAC0 to obtain BAC7. FIG. 3 schematically shows positions and directions in which the operons and the genes have been introduced. The "gent" shown in FIG. 3 means a gentamicin-resistant gene. Each arrow enclosing the name of a gene indicates a direction of that gene (i.e., a direction from 5' to 3'). Each arrow enclosing no gene name indicates a transcription promoter, and indicates a direction in which transcription proceeds.

Note that the BAC7 is not limited provided that it expresses coaD, murF, hda, mreC, hemA, lpxK and lolA genes and mreD and hemK genes, and the BAC7 can be produced by any method. For example, a hemA-prfA-hemK operon can be cloned and prfA can be removed from this operon. An operon or a gene is preferably cloned from a promoter region.

Alternatively, (i) a plasmid that expresses coaD, murF, hda, mreC, lpxK and lolA genes and a hemK gene in each of which an amber codon has been replaced with an ochre codon or with an opal codon can be introduced into *Escherichia coli* and (ii) an amber codon of a hemA gene in a genome can be replaced with an ochre codon or with an opal codon when a prfA gene is caused to be defective.

Produced BAC7 was introduced in trans into a conditional prfA mutant by an electroporation method.

How the conditional prfA mutant into which the BAC7 has been introduced grows in the presence of glucose is shown in Lanes 6 to 10 in FIG. 2. As shown in Lanes 6 to 8 of FIG. 2, although the conditional prfA mutant did not grow in a case where only the BAC7 was introduced (Lane 6), the conditional prfA mutant grew in a case where an amber suppressor tRNA$^{Gln}$ gene (Lane 7) or an amber suppressor tRNA$^{Tyr}$ gene (Lane 8) was introduced together with the BAC7. Furthermore, as shown in Lanes 9 and 10 of FIG. 2, the conditional prfA mutant grew even in a case where a pair of archaeal genes for introducing 3-iodotyrosine into a protein was introduced instead of an amber suppressor tRNA gene of *Escherichia coli* (Lane 9), and the growth capacity of the conditional prfA mutant was improved by addition of 3-iodotyrosine to a culture medium (Lane 10). Note here that the "a pair of archaeal genes" is a pair of (i) an amber suppressor tRNA gene derived from *Methanocardococcus jannaschii* and (ii) a IYRS gene derived from *Methanocardococcus jannaschii*, which IYRS gene codes for an engineered tyrosyl-tRNA synthetase (TyrRS) (Sakamoto, K., et al., Structure, Vol. 17, pp. 335-344 (2009)).

The results shown in FIG. 2 suggest that, by (i) altering amber codons of 2% of 314 genes that have amber codons and (ii) expressing endogenous or orthogonal amber suppressor tRNA, it is possible to overcome lethality in *Escherichia coli* caused by defect of a prfA gene.

[Production of Strain in which prfA Gene is Disrupted]

Next, a prfA gene was caused to be defective by (i) transducing BAC7 into a *Escherichia coli* HST08 strain and (ii) replacing a major part (51 nt to 858 nt) of the prfA gene with a Zeocin-resistant gene. Note here that HST08 is *Escherichia coli* containing a supE44 gene which codes for amber suppressor tRNA$^{Gln}$.

The prfA gene was caused to be defective by the following gene disruption method. A recombination fragment was produced by ligating, to the 5' and 3' ends of a Zeocin-resistant gene (Invitrogen), a 50-base pair DNA sequence that corresponds to the N terminal of RF-1 and a 225-base pair DNA sequence that corresponds to the C terminal of RF-1, respectively. Each of the DNA sequences was ligated to the 5' end or the 3' end in a sense direction. The recombination fragment thus obtained was inserted into a chromosome of *Escherichia coli* HST08. In the *Escherichia coli* HST08 into which the BAC7 is introduced, homologous recombination was carried out to replace the prfA gene with the recombination fragment including the Zeocin-resistant gene. In this way, the prfA gene was caused to be defective. Such a strain in which the prfA gene is disrupted is hereinafter referred to as RFzero-q. Note that a method of disrupting the prfA gene is not limited to the above disruption method, and therefore can be a well-known gene disruption method.

Figure 4:
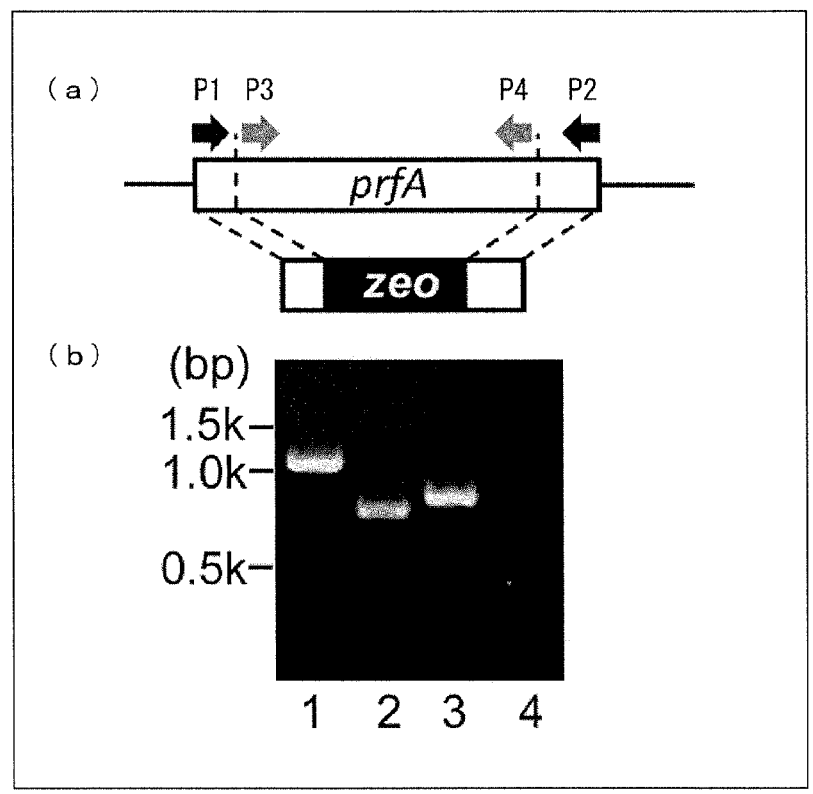
FIG. 4

Defect of the prfA gene was checked by PCR. The result is shown in FIG. 4. (a) of FIG. 4 is a view schematically showing replacement of genes and positions of primers for use in PCR for confirmation. (b) of FIG. 4 is a view showing the result of gel electrophoresis of a PCR product. Lane 1 in (b) of FIG. 4 shows the band of full-length prfA in HST08. Lane 2 in (b) of FIG. 4 shows the band corresponding to the full-length prfA in RFzero-q (amplified using a primer set indicated by arrows P1 and P2 shown in (a) of FIG. 4). Lane 3 in (b) of FIG. 4 shows a band that was detected in a case where a middle region of prfA was amplified using genome DNA of HST08. Lane 4 in (b) of FIG. 4 shows a result of detection in a case where a middle region of prfA was amplified using genome DNA of RFzero-q (amplified using a primer set indicated by arrows P3 and P4 shown in (a) of FIG. 4). It was confirmed from the results shown in FIG. 4 that a prfA gene was caused to be defective. Furthermore, the growth rate of each strain was measured by measuring optical density at 600 nm. As a result, the growth rate of the *Escherichia coli* HST08 strain into which the BAC7 was introduced was 1.3 h$^{-1}$, whereas the growth rate of a RFzero-q strain was 0.9 h$^{-1}$.

In order to confirm that the RFzero-q strain allows insertion of a glutamic acid at an amber codon, the RFzero-q strain was transformed with a mutated gene which codes for chloramphenicol acetyltransferase (cat), in which mutated gene there are three amber codons in ORF (such a mutated gene is referred to as cat(3Am)). (a) of FIG. 5 shows the amino acid sequence of the cat(3Am). The "X"s in the amino acid sequence shown in (a) of FIG. 5 indicate the positions of amber codons of the cat(3Am), and are glutamic acids in the case of the RFzero-q strain (SEQ ID NO: 17). (c) of FIG. 5 shows the result obtained by examining the chloramphenicol (Cm) resistance of a cat(3Am) transformant. As shown in (c) of FIG. 5, a RFzero-q strain which had been transformed with wild-type cat and the RFzero-q strain which had been transformed with the cat(3Am) showed chloramphenicol (Cm)

resistance until the chloramphenicol concentration in a culture medium reached 400 µg/mL.

Furthermore, a RFzero-q strain was transformed with a mutated gene which codes for cat, and in which mutated gene there are ten amber codons in ORF (such a mutated gene is referred to as cat(10Am)). (b) of FIG. 5 shows the amino acid sequence of the cat(10Am). The "X"s in the amino acid sequence shown in (b) of FIG. 5 indicate positions of amber codons of the cat(10Am), and are glutamic acids in the case of the RFzero-q strain (SEQ ID NO: 18). As shown in (c) of FIG. 5, the RFzero-q strain which had been transformed with the cat(10Am) showed Cm resistance until the chloramphenicol concentration in a culture medium reached 200 µg/mL. It is deduced that the reason why the RFzero-q strain into which the cat(10Am) was introduced showed less Cm resistance is because glutamic acid codons were translated with greater efficiency than glutamic acid insertion at amber codons. On the other hand, as shown in (b) of FIG. 5, HST08 into which the cat(10Am) had been introduced did not grow even at a Cm concentration of 10 µg/mL in the culture medium.

The results shown in FIG. 5 suggest that glutamic acids were incorporated at a plurality of amber codons. The results further demonstrate that, by introducing BAC7 into HST08 and causing a prfA gene to be defective, the efficiency of glutamic acid insertion at amber codons is dramatically improved.

[Production of Recombinant *Escherichia coli* for Production of Non-natural Protein]

A RFzero-y strain was produced by replacing a supE44 gene of the RFzero-q strain with an amber suppressor tRNA$^{Tyr}$ gene of *Escherichia coli*. Furthermore, a RFzero-iy strain was produced by replacing, in the presence of 3-iodotyrosine, the supE44 gene of the RFzero-q strain with the foregoing pair of archaeal genes. Specifically, *Escherichia coli* was transformed into recombinant *Escherichia coli* (RFzero-iy) for production of a non-natural protein, by the following transformation method. A kanamycin-resistant derivative (piodoTyrRS-MJR1-kan) (Sakamoto, K., et al., Structure, Vol. 17, pp. 335-344 (2009)) of a plasmid (piodoTyrRS-MJR1), which expresses a combination of amber suppressor tRNA (MJR1 mutant) derived from *Methanocardococcus jannaschii* and an aminoacyl-tRNA synthetase that adds 3-iodotyrosine to this orthogonal amber suppressor tRNA, was introduced into RFzero-q.

Note that the tRNA$^{Tyr}$ derived from *Methanocardococcus jannaschii* is not limited to the MJR1 mutant as above, and can therefore be for example a J17 mutant (Wang L, Schultz PG. A general approach for the generation of orthogonal tRNAs. Chem. Biol. 2001 September; 8(9): 883-90).

Figure 6:
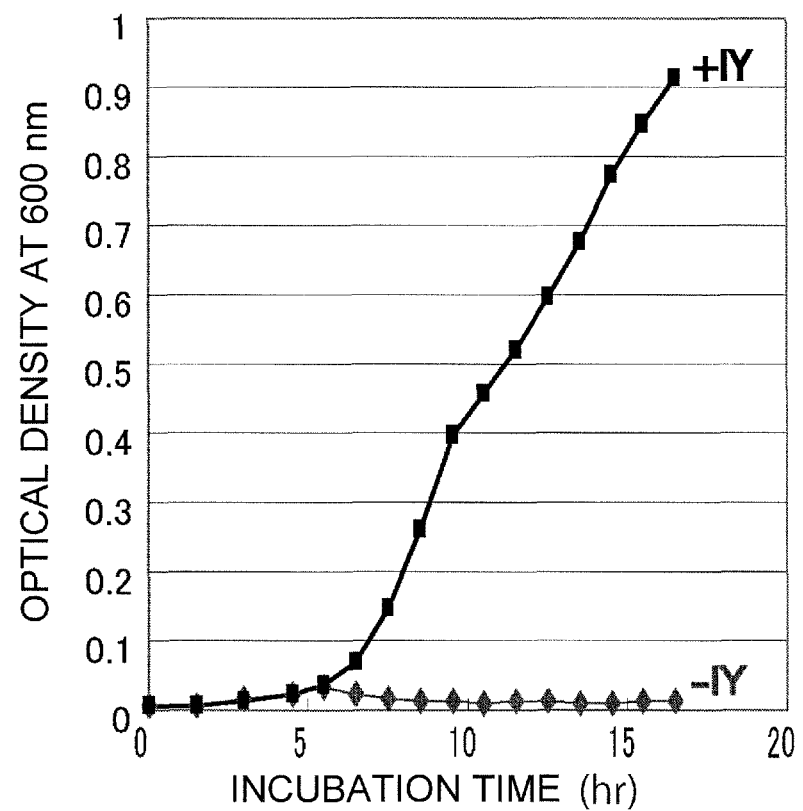
FIG. 6

FIG. 6 shows a result obtained by measuring the growth rate of the RFzero-iy strain. In FIG. 6, the "+IY" indicates the growth in the presence of 3-iodotyrosine, whereas the "-IY" indicates the growth in the absence of 3-iodotyrosine. As shown in FIG. 6, the growth rate of the RFzero-iy strain depended on the presence of 3-iodotyrosine. The result shown in FIG. 6 is consistent with the result shown in FIG. 2.

[Method of Producing Non-natural Protein]

Figure 7:
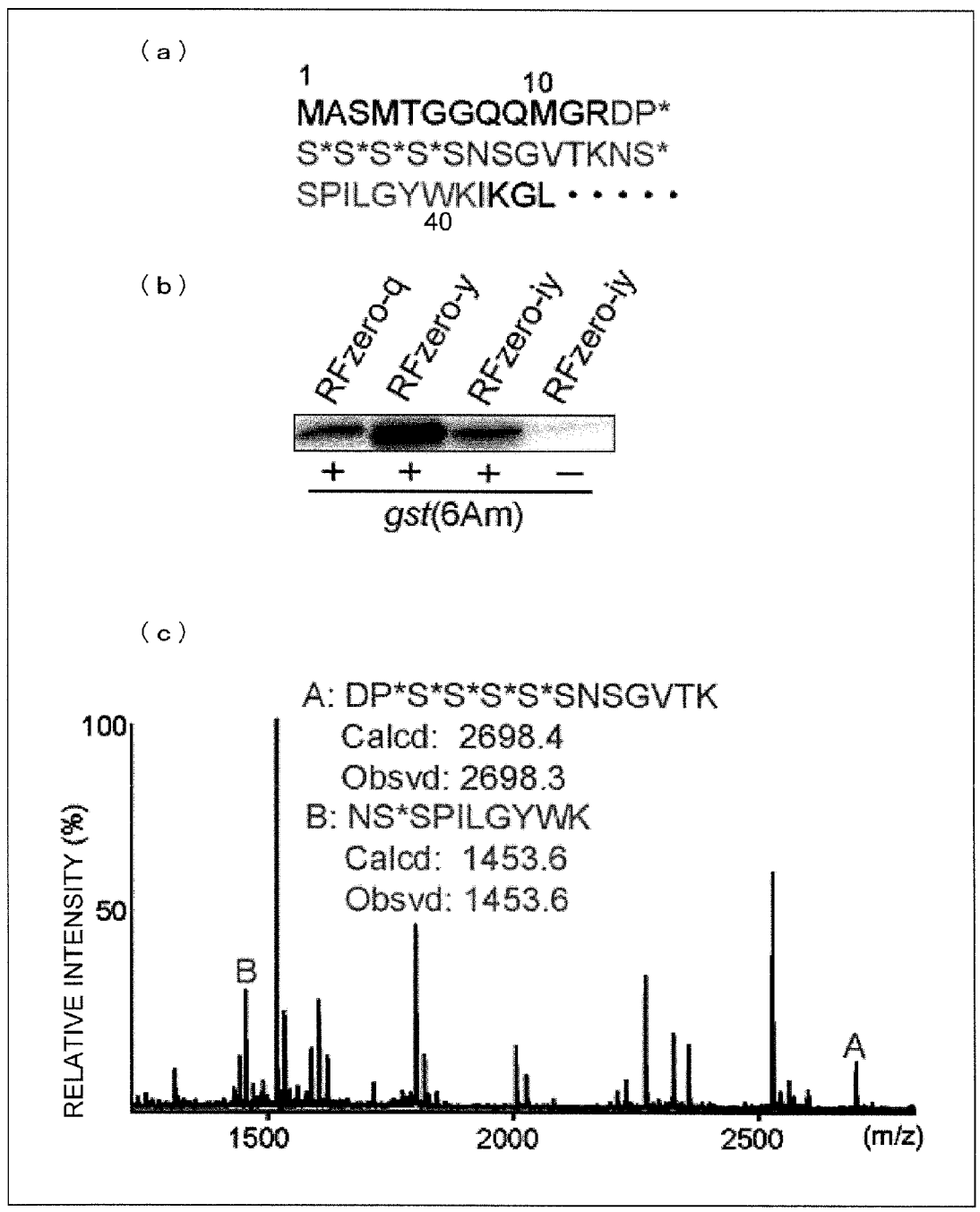
FIG. 7

Next, a mutated GST expression system was produced and was introduced into a RFzero-q strain, a RFzero-y strain and a RFzero-iy strain. The mutated GST expression system expresses, under the control of tac promoter, a glutathione-S-transferase (GST) gene into which six amber codons have been introduced near the N terminal (such a glutathione-S-transferase gene is referred to as gst(6Am)). (a) of FIG. 7 shows the sequence of 45 amino acid residues at N-terminal of the gst(6Am). The asterisks in the sequence shown in (a) of FIG. 7 indicate positions of amber codons in the gst(6Am).

SEQ ID NOs: 19 to 21 show the amino acid sequences of gst(6Am) genes in which a glutamic acid, tyrosine and 3-iodotyrosine, respectively, have been introduced at each of the positions of the amber codons.

gst(6Am) proteins were obtained from the foregoing strains (culture of 30 µL) into each of which the mutated GST expression system had been introduced, and were subjected to SDS-PAGE. Then, the gst(6Am) proteins were subjected to western blotting using anti-GST antibodies (refer to (b) of FIG. 7).

Figure 8:
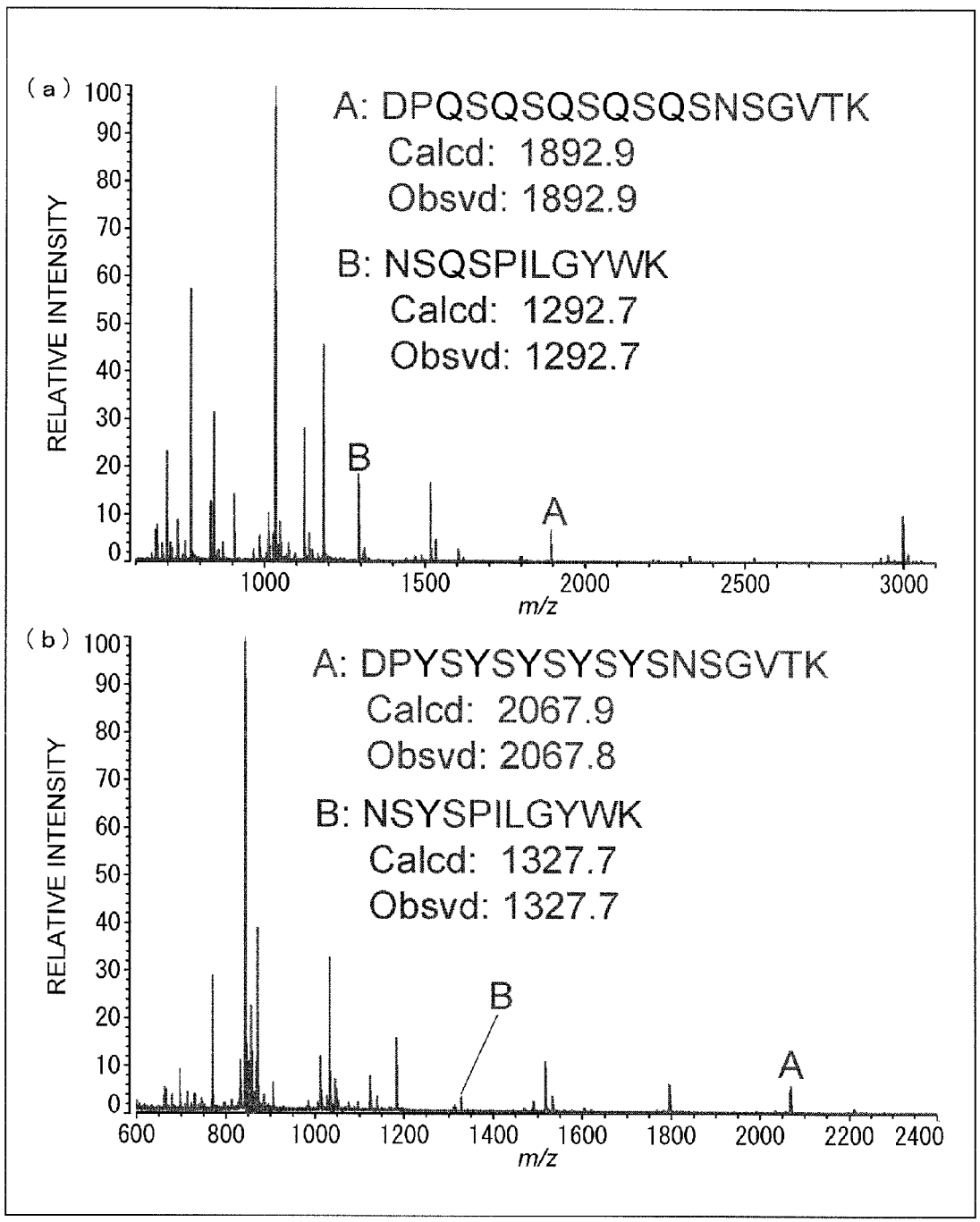
FIG. 8

The gst(6Am) proteins thus obtained were trypsinized, and the gst(6Am) proteins thus trypsinized were analyzed by mass spectrometry. (c) of FIG. 7 shows the result obtained by analyzing a gst(6Am) protein obtained from the RFzero-iy strain. (a) and (b) of FIG. 8 show the results obtained by analyzing gst(6m) proteins obtained from the RFzero-q strain and the RFzero-y strain, respectively. As is clear from (c) of FIG. 7, the result of the mass spectrometry analysis shows that the RFzero-iy strain produced a peptide A containing five 3-iodotyrosines: DP*S*S*S*S*SNSGVTK (SEQ ID NO: 22) and a peptide B containing one 3-iodotyrosine: NP*SSPILGYWK (SEQ ID NO: 23). Note here that the "*" indicates the position of an amber codon in each of the gst (6Am) proteins, at which position 3-iodotyrosine was introduced. Furthermore, the results in FIG. 8 show that the RFzero-q strain and the RFzero-y strain produced peptides in which glutamic acid and tyrosine, respectively, was introduced at each of the positions of the six amber codons. The amino acid sequences obtained by analyzing the protein obtained from the RFzero-q strain are shown in SEQ ID NOs: 24 and 25, and the amino acid sequences obtained by analyzing the protein obtained from the RFzero-y strain are shown in SEQ ID NOs: 26 and 27.

As has been described, it has been found that it is possible to produce *Escherichia coli* for production of a non-natural protein, by (i) expressing, in *Escherichia coli*, tRNA which recognizes UAG codon, (ii) expressing an aminoacyl-tRNA synthetase which acylates the tRNA with 3-iodotyrosine which is a non-natural amino acid, (iv) introducing, into *Escherichia coli*, a DNA construct (e.g., BAC7) for expressing a function of at least one gene selected from the group consisting of genes each of which loses its function when a prfA gene is defective and (v) causing the prfA gene of *Escherichia coli* to be defective.

As described above, by using a method of producing *Escherichia coli* for production of a non-natural protein in accordance with the present invention, it is possible to easily cause a prfA gene of *Escherichia coli* to be defective. This makes it possible to easily improve efficiency of non-natural protein production using desired *Escherichia coli*. Furthermore, *Escherichia coli* of the present invention makes it possible to efficiently introduce a non-natural amino acid into a protein. Moreover, by a method of producing a non-natural protein in accordance with the present invention, it is possible to efficiently produce a non-natural protein.

According to the present invention, it is possible to easily cause a prfA gene of *Escherichia coli* to be defective. Therefore, it is possible to produce various prfA-defective strains with use of a library of *Escherichia coli* strains. This makes it possible, when producing a non-natural protein, to select a suitable prfA-defective strain depending on a desired protein. As such, according to the present invention, it is expected that a non-natural protein will be produced efficiently as compared to a case where *Escherichia coli* with low versatility is used.

Example 2

In Example 1, a method of producing *Escherichia coli* for production of a non-natural protein into which 3-iodotyrosine has been introduced, and the like, were described. Note, however, that the present invention can employ not only 3-iodotyrosine but also any non-natural amino acid. In the present example, (i) recombinant *Escherichia coli* for production of a non-natural protein into which 4-azidophenylalanine (non-natural amino acid) was introduced was produced and (ii) a non-natural protein was produced by using the recombinant *Escherichia coli*.

In the present example, a RFzero-azf strain was produced by introducing, instead of a IYRS gene, a AzFRS gene (Chin J W, Santoro S W, Martin A B, King D S, Wang L, Schultz P G. Addition of p-azido-L-phenylalanine to the genetic code of *Escherichia coli*. J Am Chem. Soc. 2002 Aug. 7; 124(31): 9026-7.) derived from *Methanococcus jannaschii*. *Methanococcus jannaschii* is an aminoacyl-tRNA synthetase which adds 4-azidophenylalanine to amber suppressor tRNA. The same operations as in Example 1 were carried out except that the AzFRS gene was introduced instead of the IYRS gene.

gst(6Am) proteins were obtained from strains (culture of 30 μL) into each of which the mutated GST expression system was introduced, and were subjected to SDS-PAGE. Then, the gst(6Am) proteins were subjected to western blotting using anti-GST antibodies. The results are shown in FIG. 9.

Figure 9:
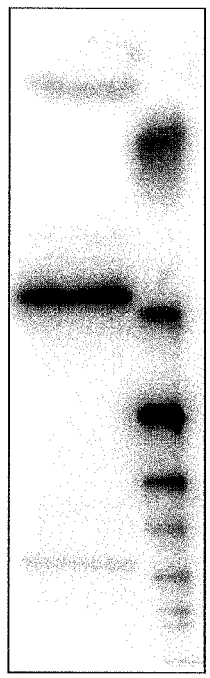
FIG. 9

As shown in FIG. 9, full-length gst was expressed in the RFzero-azf strain. This shows that the RFzero-azf strain, into which the AzFRS gene was introduced instead of the IYRS gene, was successfully mutated by introducing 4-azidophenylalanine at an amber codon. That is, any non-natural amino acid can be used in the present invention.

Example 3

The foregoing examples were such that, among all genes whose translation is terminated at a UAG codon, all seven genes of *Escherichia coli* defect of any one of which seven genes alone is lethal were caused to perform their functions.

In the present example, a recombinant bacterium was produced by introducing a smaller number of genes into BAC. Specifically, (i) a BAC plasmid that does not contain any of six genes (other than hda) of the seven genes (coaD, murF, hda, mreC, hemA, lpxK and lolA) of *Escherichia coli*, defect of any one of which seven genes alone is lethal, was prepared, (ii) the BAC plasmid was introduced into *Escherichia coli*, and (iii) a prfA gene of this *Escherichia coli* was caused to be defective. *Escherichia coli* used here was a HST08 strain. The result is shown in FIG. 10.

Figure 10:
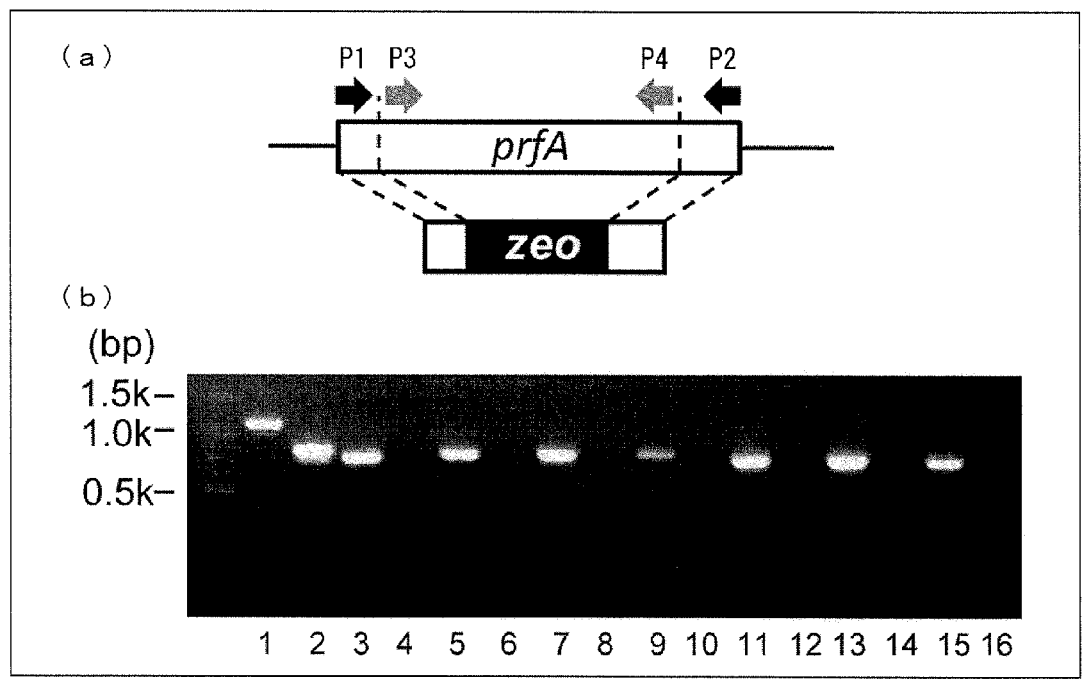
FIG. 10

(a) of FIG. 10 is a view schematically showing replacement of genes and positions of primers for PCR for confirmation. (b) of FIG. 10 is a view showing the result of gel electrophoresis of a PCR product. (b) of FIG. 10 shows (i) fragments of the following strains each of which fragments was amplified with a primer set of P7 and P8 shown in (a) of FIG. 10 or with a primer set of P9 and P10 shown in (a) of FIG. 10 or (ii) defect of a prfA gene. Lanes 1 and 2: HST08+BAC7, Lanes 3 and 4: RFzero-q only, Lanes 5 and 6: RFzero-q+ΔmurF (This means BAC into which six genes other than murF was introduced. The same applies to the following strains.), Lanes 7 and 8: RFzero-q+ΔcoaD, Lanes 9 and 10: RFzero-q+ΔmreBCD, Lanes 11 and 12: RFzero-q+ΔlpxK, Lanes 13 and 14: RFzero-q+ΔhemAK, and Lanes 15 and 16: RFzero-q+ΔlolA. Those shown in odd-numbered lanes were amplified with use of a primer set indicated by arrows P5 and P6 in (a) of FIG. 10, and those shown in even-numbered lanes were amplified with use of a primer set indicated by arrows P7 and P8 shown in (a) of FIG. 10.

The results shown in FIG. 10 show that it is possible to produce a growable prfA-defective strain even in a case where the number of genes which are introduced into BAC is reduced (which genes to be omitted should be other than hda).

Figure 11:
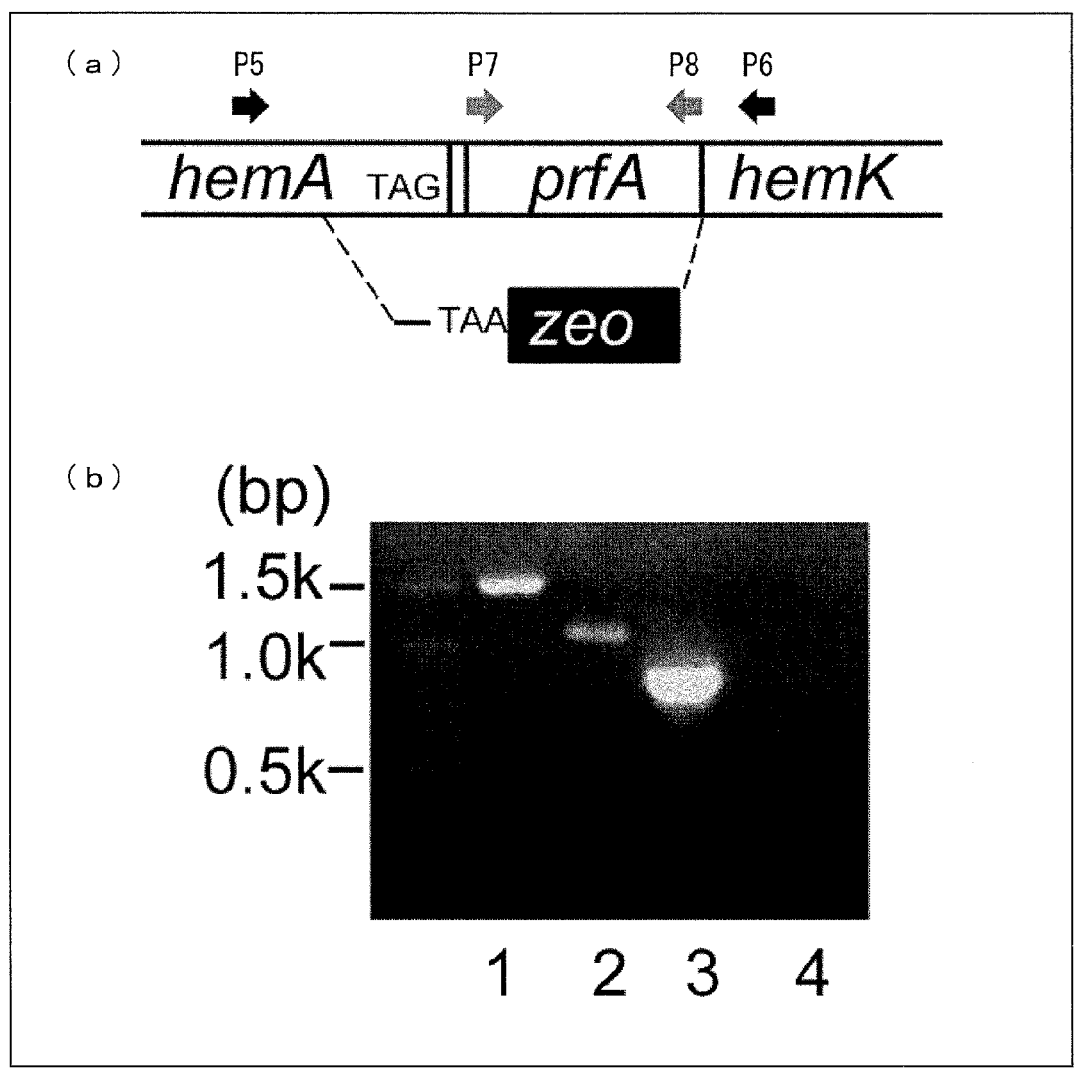
FIG. 11

Furthermore, BAC3 containing only a waaA-coaD operon, a hda gene, or a mreB-mreC-mreD operon (or mutated gene) was produced, and introduced into HST08 (refer to FIG. 11). Next, a prfA gene was replaced with a Zeocin-resistant gene so that the entire prfA was removed, thereby the prfA gene was caused to be defective. Note that, since a hemA gene is adjacent to the prfA gene in a genome, a TAG codon (stop codon) of the hemA gene in the genome was replaced with TAA when recombination was carried out to cause the prfA gene to be defective. That is, this process is a combination of (i) a method of introducing a gene in trans, defect of which gene alone is lethal and (ii) a method of altering an amber codon of a gene in a chromosome, defect of which gene alone is lethal.

(a) of FIG. 11 is a view schematically showing replacement of genes and positions of primers for PCR for confirmation. (b) of FIG. 11 is a view showing the result of gel electrophoresis of a PCR product. (b) of FIG. 11 shows (i) fragments of the following strains into each of which BAC3 was introduced, each of which fragments was amplified with a primer set indicated by arrows P5 and P6 shown in (a) of FIG. 11 or with a primer set indicated by arrows P7 and P8 shown in (a) of FIG. 11 or (ii) defect of prfA gene. Lane 1: HST08, Lane 2: HST08, Lane 3: HST08+BAC3+prfA defect, and Lane 4: HST08+BAC3+prfA defect. Those shown in odd-numbered lanes were amplified with use of a primer set indicated by arrows P5 and P6 in (a) of FIG. 11, and those shown in even-numbered lanes were amplified with use of a primer set indicated by arrows P7 and P8 shown in (a) of FIG. 11.

The results shown in FIG. 11 show that it is possible to produce a growable prfA-defective strain even in a case where the number of genes which are introduced into BAC is reduced (which genes to be omitted should be other than hda).

Furthermore, it is possible to add any gene to at least one gene selected from the group consisting of genes each of which loses its function when a gene that codes for a release factor for terminating translation at a UAG codon is defective. Specifically, some of the strains, which were obtained by introducing a smaller number of genes into BAC, grew at a lower rate. It is easily to understand from this that, in a case where the number of genes is increased, the growth rate of *Escherichia coli* and/or productivity of a non-natural protein will be further improved. The present invention also encompasses embodiments in which the number of genes is increased. A gene to be added is desirably a gene that is known to dramatically reduce the growth rate of a bacterium if caused to be defective alone, among all the genes whose translation is terminated at a UAG codon. In the case of *Escherichia coli*, such genes are, but not limited to, fliN, fliP, fliQ, sucB, ubiF, ulaF, atpE, and fabH. The nucleotide sequences of the fliN, fliP, fliQ, sucB, ubiF, ulaF, atpE and fabH genes are shown in SEQ ID NOs: 9, 10, 11, 12, 13, 14, 15 and 16, respectively. Note that each of the nucleotide sequences of these genes shown in SEQ ID NOs: 9, 10, 11, 12, 13, 14, 15 and 16 is of a *Escherichia coli* K-12 strain. Therefore, in other strains, some nucleotides may be substituted. Genes of such other strains are also encompassed in the above genes. The number of genes to be added is preferably 1 to 30, more preferably 1 to 20, and most preferably 1 to 10.

Example 4

In the foregoing examples, an *Escherichia coli* HST08 strain was used as a host bacterium. Note, however, that other *Escherichia coli* can be used. In the present example, a recombinant bacterium (RFzero-iy) for production of a non-natural protein was produced by using HMS174 (DE3), which is a K-12 strain, instead of using the *Escherichia coli* HST08 strain. Further, a recombinant bacterium (RFzero-q), into which GlnRS and tRNA$^{Gln}_{CUA}$ were introduced instead of a pair including an amber suppressor tRNA gene derived from *Methanocardococcus jannaschii* and an IYRS gene derived from *Methanocardococcus jannaschii*, was produced.

First, BAC6-AhemAK was introduced in trans into HMS174 (DE3). Note here that the BAC6-AhemAK is a BAC plasmid obtained by removing a hemAK operon from a BAC7 plasmid by replacing the hemAK operon with CAT. Next, a plasmid that codes for a pair of amber suppressor tRNA and its corresponding aminoacyl-tRNA synthetase was introduced. Next, prfA was replaced with a Zeocin-resistant gene, thereby a prfA gene was caused to be defective. In the present example, the prfA was replaced with the Zeocin-resistant gene so that the entire prfA was removed (refer to (a) of FIG. 12). Note that, also in the present example, a TAG codon (stop codon) of a hemA gene in a genome was replaced with TAA when recombination was carried out to cause the prfA gene to be defective.

Note that, as shown in FIG. 2, *Escherichia coli*, which does not express (i) tRNA that recognizes UAG codon (in other words, amber suppressor tRNA) and (ii) an enzyme that aminoacylates the tRNA, does not grow merely by introduction of BAC7. Therefore, it is preferable to (i) transform *Escherichia coli* so that the *Escherichia coli* expresses tRNA that recognizes UAG codon and an enzyme that aminoacylates the tRNA and thereafter (ii) cause a prfA gene of the *Escherichia coli* to be defective.

Figure 12:
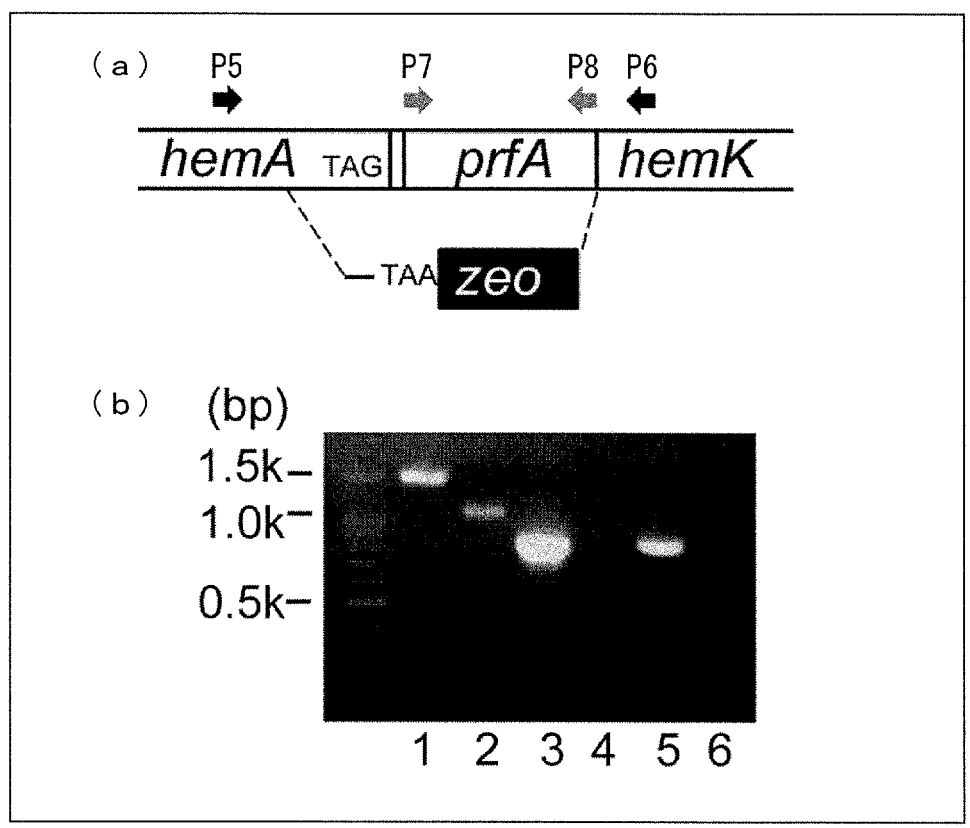
FIG. 12

(a) of FIG. 12 is a view schematically showing replacement of a prfA gene and positions of primers for PCR for confirmation of defect. (b) of FIG. 12 is a view showing the result of gel electrophoresis of a PCR product. The following are strains, in respective lanes, whose DNA was used as template DNA. Lane 1: HST08, Lane 2: HST08, Lane 3: RFzero-q derived from HMS174 (DE3), Lane 4: RFzero-q derived from HMS174 (DE3), Lane 5: RFzero-iy derived from HMS174 (DE3), and Lane 6: RFzero-iy derived from HMS174 (DE3). Those shown in odd-numbered lanes have been amplified with use of a primer set indicated by arrows P5 and P6 in (a) of FIG. 12, and those shown in even-numbered lanes were amplified with use of a primer set indicated by arrows P7 and P8 shown in (a) of FIG. 12. It was confirmed from the results shown in FIG. 12 that prfA gene was caused to be defective.

Example 5

In the present example, a gene that improves the growth rate of recombinant *Escherichia coli* for production of a non-natural protein was searched for among genes (i) whose translation is terminated at a UAG codon and (ii) each of which is known to dramatically reduce the growth rate of a bacterium if caused to be defective alone. Candidate genes were searched for by using a BW25113 strain. The BW25113 strain is a parent strain of a KEIO collection (Baba et al., Mol. Syst. Biol. 2, 2006. 0008 (2006)), and is substantially the same as a wild-type K-12 strain. To search for candidate strains, a ΔprfA strain was produced from the BW25113 strain. Specifically, (i) BAC6-AhemAK containing a cat gene was introduced, (ii) pGlnRS-supE-kan which expresses supE and glutaminyl-tRNA synthetase (GlnRS) was further introduced or piodoTyrRS-MJR1-kan was further introduced, and thereafter (iii) prfA was replaced with a Zeocin-resistant gene, thereby a prfA gene was caused to be defective. In the present example, the prfA was replaced with the Zeocin-resistant gene so that the entire prfA was removed. Note that, also in the present example, a TAG codon (stop codon) of a hemA gene in a genome was replaced with TAA when recombination was carried out to cause the prfA gene to be defective. Since BW25113 is similar to a wild-type strain, BW25113 is highly resistant to antibiotics. Therefore, selection of a recombinant colony was carried out at a Zeocin concentration of 75 μg/ml.

A stop codon of each of the candidate genes was replaced with TAA by PCR, and thereafter each of the candidate genes was cloned into a pAp102 vector. In this way, expression plasmids were produced. Next, a ΔprfA strain was transformed with each of the expression plasmids. As a result, a transformant, into which a system for expressing sucB (sucB is one of the candidate genes) had been introduced, grew well especially in a liquid culture medium at 30° C. Table 1 shows the result of analysis on growth, which result is obtained by (i) introducing the sucB expression plasmid or a control into BW25113 [BAC6-ΔhemAK piodoTyrRS-MJR1-kan prfA::zeo hemA (TAG→TAA)] which is the foregoing ΔprfA strain and (ii) culturing a single colony at 30° C. overnight with shaking. The sucB is a gene that codes for an E2 subunit of alpha-ketoglutarate dehydrogenase, which constitutes a citric acid cycle. It is deduced that, since two UAG codons of a wild-type sucB gene are adjacent to each other in a wild-type sucB gene, expression or activity of the wild-type sucB gene considerably decreases because 3-iodotyrosines were introduced therein adjacently to each other. Note that, since the colonies in the plate cultures were not much different in size, it is expected that the function of sucB contributes to especially the growth potential in a liquid culture medium.

TABLE 1

| Introduced Construct | OD600 |
|---|---|
| System for expressing sucB | 1.26 |
| pAp102 vector | 0.93 |

Example 6

In the present example, recombinant bacteria (BW25113RFzero-iy, HMS174RFzero-iy, and BL21RFzero-iy), each of which is for production of a non-natural protein, were produced with use of (i) BW25113, HMS174 (DE3) (K-12 strain), and BL21 (DE3) derived from a B strain, respectively, instead of *Escherichia coli* HST08 strains and (ii) a plasmid obtained by incorporating a sucB gene into a BAC7 plasmid.

Figure 13:
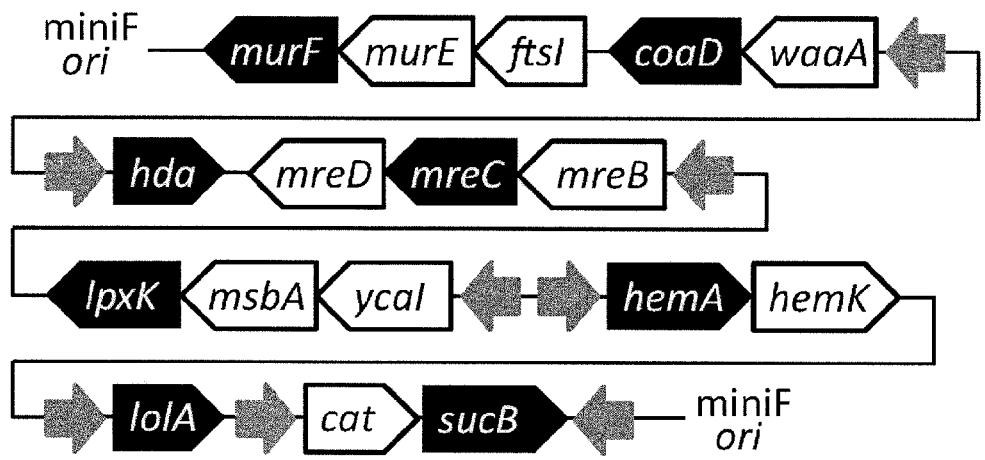
FIG. 13

First, sucB in which a stop codon had been replaced with TAA was cloned into a BAC7 plasmid. Further, a selection marker in the BAC7 plasmid was replaced with cat, thereby obtaining a plasmid, which is referred to as a BAC8 plasmid hereinafter. FIG. 13 schematically shows positions and directions in which operons and genes have been introduced into the BAC8 plasmid. As shown in FIG. 13, sucB was cloned immediately downstream of a stop codon of cat. Therefore, transcription of sucB is under the control of cat promoter.

Figure 14:
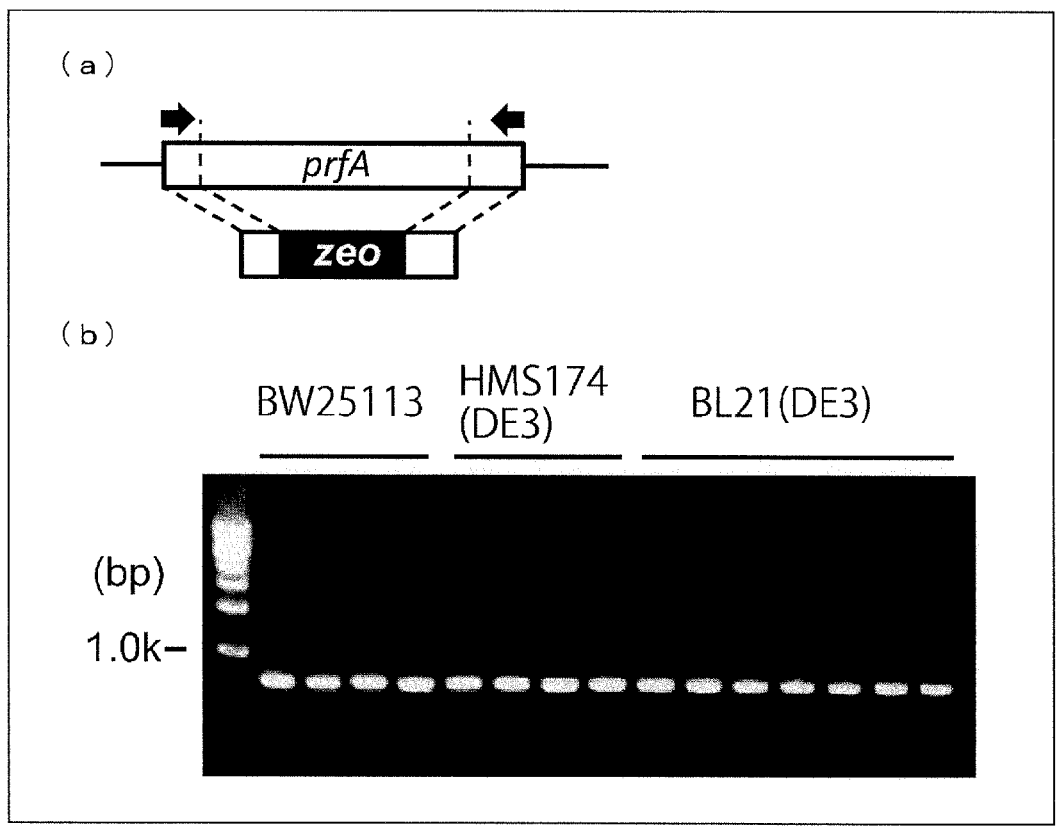
FIG. 14

Next, the BAC8 was introduced into BW25113, HMS174 (DE3), and BL21 (DE3). Further, piodoTyrRS-MJR1-gent was introduced into each strain into which the BAC8 was introduced. The piodoTyrRS-MJR1-gent is the same as piodoTyrRS-MJR1-kan except that a marker gene was changed from a kanamycin-resistant gene to a gentamicin-resistant gene. Next, in the same manner as in Example 5, a prfA gene was caused to be defective by replacing prfA with a Zeocin-resistant gene. PCR was carried out with respect to each RFzero-iy strain to confirm the defect of the prfA gene. The results are shown in FIG. 14. (a) of FIG. 14 is a view schematically showing replacement of genes and positions of primers for PCR for confirmation. (b) of FIG. 14 is a view showing the result of gel electrophoresis of a PCR product. As a result of PCR of colonies, the defect of the prfA gene was confirmed (refer to (b) of FIG. 14). These results have shown that it is possible to easily cause, with use of BAC8, a prfA gene to be defective in each of the *Escherichia coli* strains derived from a K-12 strain and a B strain.

Figure 24:
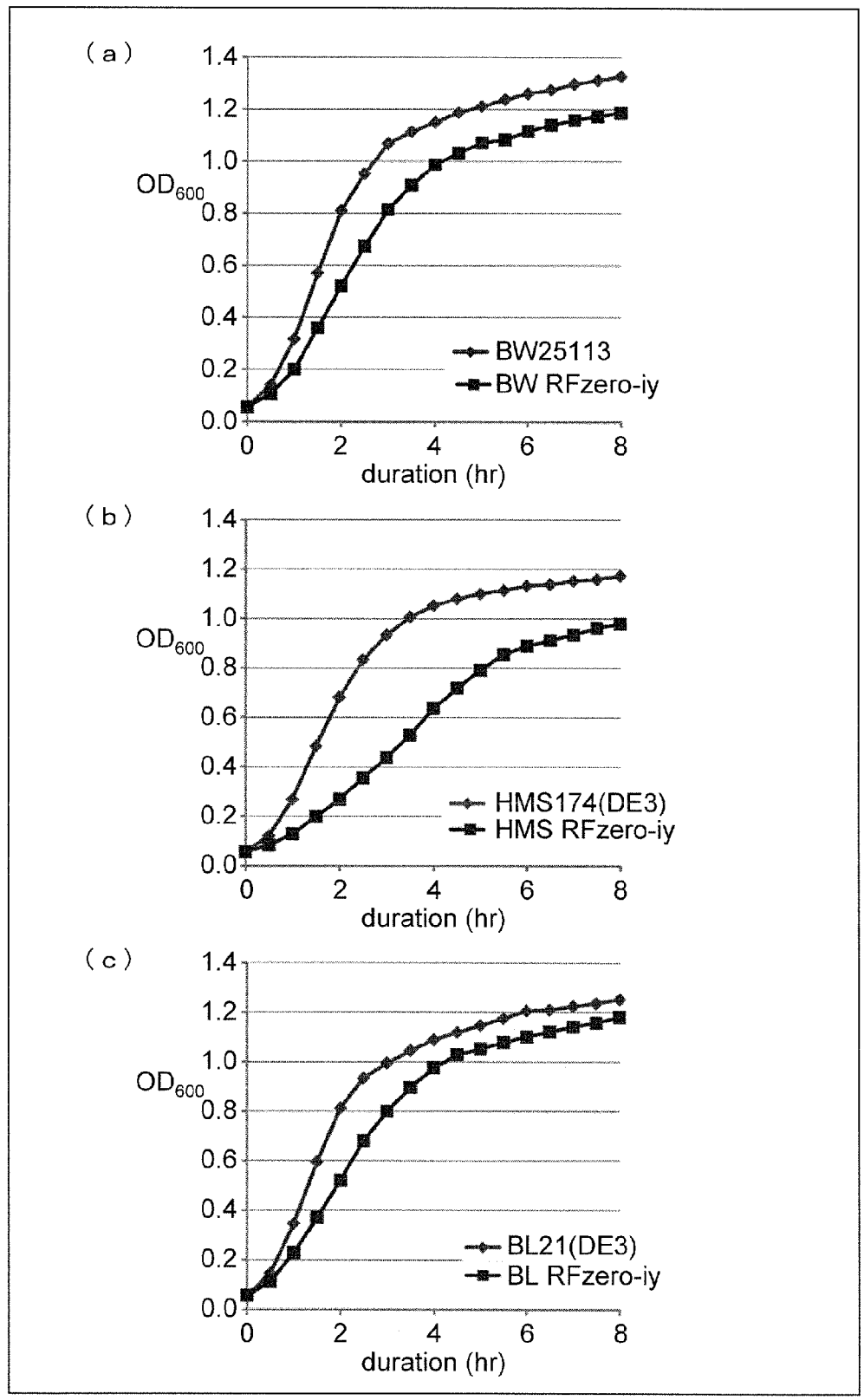
FIG. 24

The growth rates of obtained BW25113RFzero-iy, HMS174RFzero-iy, and BL21RFzero-iy in a culture medium containing 3-iodotyrosine were measured. The results are shown in FIG. 24. The results show that the BW25113RFzero-iy and the BL21RFzero-iy grew at substantially the same rate as their parent strain (prfA$^+$) ((a) and (c) of FIG. 24). On the other hand, the HMS174RFzero-iy grew at a lower rate than its parent strain (prfA$^+$) ((b) of FIG. 24).

Figure 25:
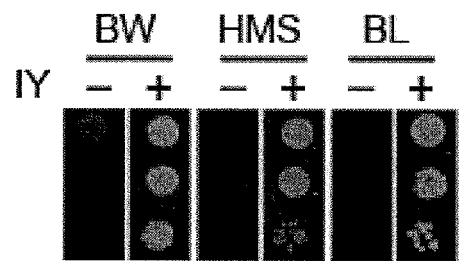

Furthermore, how much the growth of each of the RFzero-iy strains depends on non-natural amino acids was checked. A cell culture having been incubated overnight was diluted, the diluted culture was spotted on (i) a non-selective LB culture medium containing 3-iodotyrosine and (ii) a non-selective LB culture medium containing no 3-iodotyrosine. The media were further incubated. The results are shown in FIG. 25. As is clear from FIG. 25, the growth of all the RFzero-iy strains totally depended on the presence of 3-iodotyrosine. This is consistent with the fact that UAG translation activity is necessary in a cell to avoid lethality caused by prfA knockout.

Example 7

In the present example, the properties of the BW25113RFzero-iy strain produced in Example 6 were examined.

First, a minute amount of glycerol stock of a BW25113RFzero-iy strain was added to (i) an LB liquid culture medium and (ii) an LB liquid culture medium to which 3-iodotyrosine (IY), 3-bromotyrosine (BrY) or 3-chlorotyrosine (ClY) had been added, and incubated with shaking at 37° C. overnight. In this way, the growth of the BW25113RFzero-iy strain was examined. The result is shown in Table 2.

TABLE 2

| Non-natural Amino Acid | OD600 |
|---|---|
| — | 0.00 |
| IY | 1.36 |
| BrY | 1.39 |
| ClY | 1.41 |

As shown in Table 2, cell growth was not at all observed in the LB liquid culture medium containing no non-natural amino acids. On the other hand, in the case of the LB liquid culture media to which non-natural amino acids had been added, the turbidity OD600 of the cell culture was approximately 1.4 regardless of types of non-natural amino acid, i.e., cells grew sufficiently. That is, iodoTyrRS-mj recognized not only 3-iodotyrosine but also 3-bromotyrosine and 3-chlorotyrosine.

The foregoing analyses show that a UAG codon of a BW25113RFzero-iy strain can be assigned to any of 3-iodotyrosine, 3-bromotyrosine and 3-chlorotyrosine. The same should be true with HMS174(DE3)RFzero-iy and BL21 (DE3)RFzero-iy.

Example 8

In the foregoing Example 2, a recombinant bacterium (RFzero-azf) for production of a non-natural protein, into which a non-natural amino acid (4-azidophenylalanine) that is other than 3-iodotyrosine was introduced, was produced by using a HST08 strain as a host bacterium. In the present example, BL21 (DE3) was used as a host bacterium, and not only 4-azidophenylalanine but also o-sulfotyrosine was introduced as a non-natural amino acid that is other than 3-iodotyrosine.

In a case where 4-azidophenylalanine or o-sulfotyrosine is introduced, it is necessary that a AzFRS gene (AzFRS-mj) or a SfYRS gene (SfYRS-mj) (Liu, C. C. and Schultz, P. G., Nat. Biotechnol., 2006, 24, 1436-1440.) be expressed. The AzFRS gene is derived from *Methanococcus jannaschii* which is an aminoacyl-tRNA synthetase specific to 4-azidophenylalanine, and the SfYRS gene is derived from *Methanococcus jannaschii* which is an aminoacyl-tRNA synthetase specific to o-sulfotyrosine, be expressed.

First, pETGST(6Am)-AzFRS-mj or pETGST(6Am)-SfYRS-mj was produced by cloning, into a plasmid pETGST (6Am) obtained by cloning gst(6Am) into a pET21b vector, a system for expressing AzFRS-mj or a system for expressing SfYRS-mj. For improvement of the activity of the AzFRS-mj and the SfYRS-mj, a D286R mutation (Kobayashi, K. et al., Proc. Natl. Acad. Sci. USA, 2003, 100, 4678-4683.) was further introduced.

Next, BL21RFzero-iy produced in Example 6 was transformed with the pETGST(6Am)-AzFRS-mj or the pETGST (6Am)-SfYRS-mj, and the transformed strain was seeded in an LB plate containing 4-azidophenylalanine or an LB plate containing o-sulfotyrosine. Then, colony formation was checked. Note that a strain in which a UAG codon has been reassigned to 4-azidophenylalanine is referred to as BL21RFzero-azf, and a strain in which a UAG codon has been reassigned to o-sulfotyrosine is referred to as BL21RFzero-sfy. As a result, the growth rate of the BL21RFzero-azf on the AzF plate was lower than that of RFzero-iy on the IY plate, and the growth rate of the BL21RFzero-sfy on the SfY plate was equal to or higher than that of RFzero-iy on the IY plate. Note that the BL21RFzero-azf and the BL21RFzero-sfy show little growth on the LB plate containing 3-iodotyrosine, probably for the following reason. The AzFRS-mj and the SfYRS-mj are expressed from an intermediate-copy-number plasmid, and strongly recognize tRNA$^{Tyr}_{CUA}$ molecules derived from *M. jannaschii* due to a D286R mutation. Therefore, tRNA is taken away from weak iodoTyrRS-mj which is expressed from a low-copy-number plasmid.

Example 9

In Example 8, the growth rate of the BL21RFzero-sfy was greater than that of the BL21RFzero-azf. Since the activity of the AzFRS-mj is lower than those of other mutants, the efficiency of UAG translation and the growth rate of a RFzero strain are probably related to each other. In view of the circumstances, since it appears that the amount of *Methanococcus jannaschii* tRNA$^{Tyr}_{CUA}$ molecules is insufficient as compared to an excessive amount of *Methanococcus jannaschii* TyrRS mutants, a system for overexpressing *Methanococcus jannaschii* tRNA$^{Tyr}_{CUA}$ was further introduced. A pAzPhe1 mutant has been reported as substrate tRNA for the AzFRS-mj. The pAzPhe1 mutant is known to increase the efficiency of amber suppression 3.6 times (Guo et al., Angew. Chem. Int. Ed. Engl., 2009, 48, 9148-9151.). In view of this, pETGST (25Am)-AzFRS-mj-pAzPhe1 was produced by cloning, into pETGST(25Am), a system for expressing both AzFRS-mj and pAzPhe1. The pAzPhe1 was expressed under a 1 pp promoter. The 1 pp promoter is known as a strong promoter.

The BL21RFzero-iy strain produced in Example 6 was transformed with the pETGST(25Am)-AzFRS-mj-pAzPhe1, and the BL21RFzero-iy strain thus transformed was seeded in an LB plate containing 4-azidophenylalanine or 3-iodotyrosine. The result is shown in Table 3. On the plate containing 4-azidophenylalanine, the BL21RFzero-azf (AzFRS-mj-pAzPhe1) strain grew much better than the BL21RFzero-azf (AzFRS-mj) strain (refer to columns 1 and 3 in Table 3) and grew better than the RFzero-iy strain (refer to column 1 and 2 in Table 3). Further, the BL21RFzero-azf (AzFRS-mj-pAzPhe1) strain also grew on the LB plate containing 3-iodotyrosine (column 4 in Table 3). This indicates that it is possible to reassign the UAG codon to other non-natural amino acid by introducing, into a BL21(DE3)RFzero-iy strain, an intermediate-copy-number plasmid which carries a TyrRS mutant/tRNA$^{Tyr}_{cuA}$ pair derived from *Methanococcus jannaschii*.

TABLE 3

|  | 1 | 2 | 3 | 4 |
|---|---|---|---|---|
| Size of Colony | ++++ | +++ | ++ | + |
| AzFRS-mj (D286) | + | − | + | + |
| pAzPhe1 | + | − | − | + |
| Amino Acid | AzF | IY | AzF | IY |

Next, a supporting experiment was conducted with use of a BW25113RFzero-iy strain. pTacGST-iodoTyrRS-mj-Nap3, pTacGST-AzFRS-mj-pAzPhe1, and pTacGST-SfYRS-mj-Nap3 were produced, which are pTacGST plasmids (i) in each of which gst has been ligated downstream of a tac promoter and (ii) which carry an iodoTyrRS-mj-Nap3 expression system, an AzFRS-mj-pAzPhe1 expression system, and an SfYRS-mj-Nap3 expression system, respectively. Nap3 is a highly active mutant of tRNA$^{Tyr}_{CUA}$ (described later). Furthermore, each aaRS has a D286 mutation. The BW25113RFzero-iy strain was transformed with one of these three plasmids, a colony of the transformed strain was diluted in steps of 10 fold, and the diluted colony was spotted on (i) an LB plate containing a non-natural amino acid or (ii) an LB plate containing no non-natural amino acid. The result is shown in FIG. 15.

Figure 15:
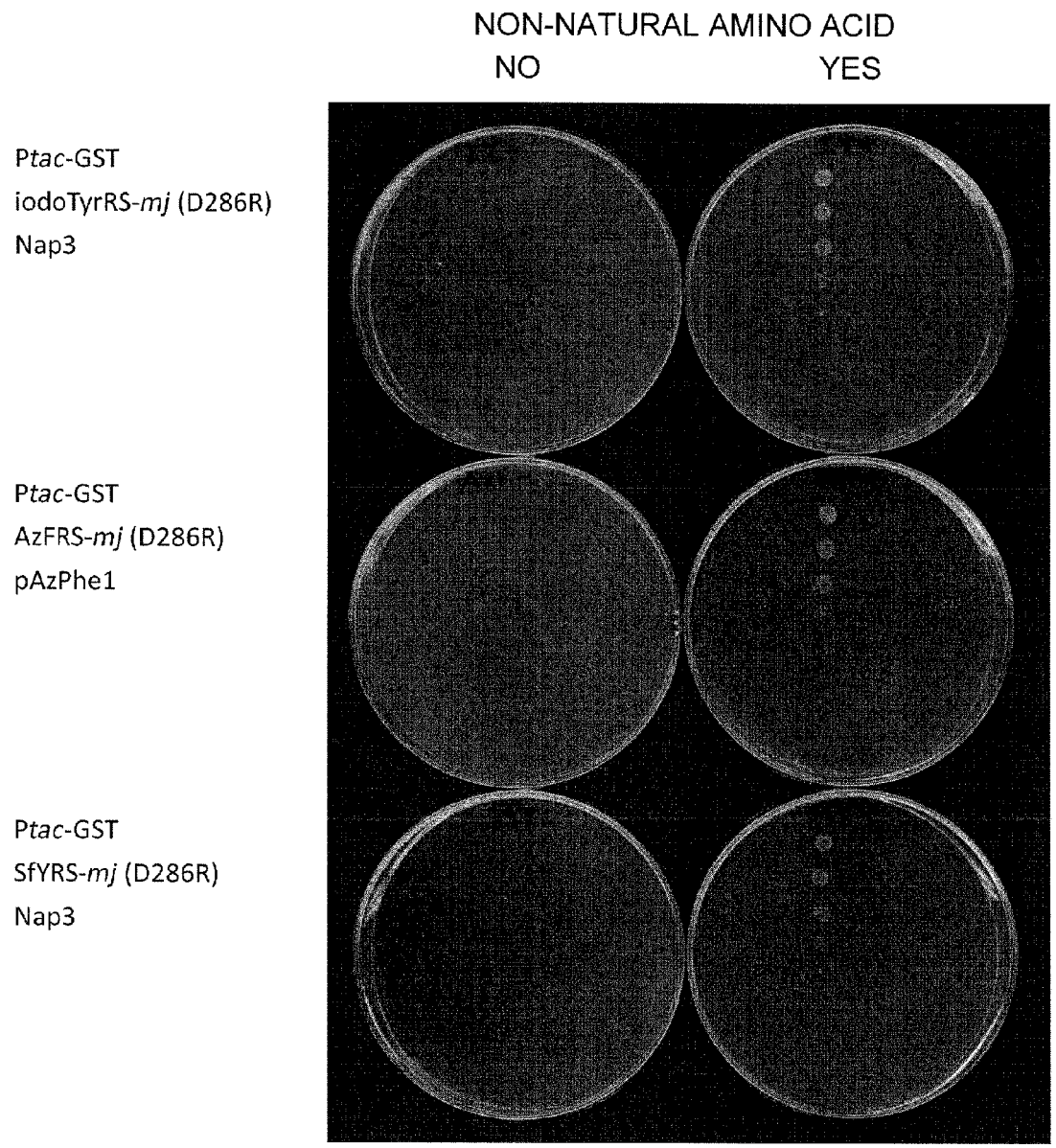
FIG. 15

As is clear from FIG. 15, each transformant grew only on the plate containing a non-natural amino acid, and did not at all grow on the plate containing no non-natural amino acid. This has demonstrated that, as is the case with the BL21(DE3)RFzero-iy strain, the UAG codon of the BW25113RFzero-iy strain can also be reassigned to other non-natural amino acid.

Example 10

The foregoing examples suggest that, in order to increase the growth rate of a RFzero-iy strain, it is only necessary to improve a iodoTyrRS-mj/tRNA$^{Tyr}_{CUA}$ pair. In view of this, the present example employs a Nap3 mutant which is expected to, like a pAzPhe1 mutant, be a highly-active substrate that can be well recognized by many *Methanococcus jannaschii* TyrRS mutants. Note that the pAzPhe1 is the same as the Nap3 except that C16 is defective (Guo et al., Angew. Chem. Int. Ed. Engl., 2009, 48, 9148-9151.).

First, pTacGST(73Am)-iodoTyrRS-mj-Nap3 was produced by incorporating, into a pTacGST(73Am) plasmid into which a gst(73Am) mutant had been cloned, a system for expressing iodoTyrRS-mj(D286R) and Nap3. Next, the pTacGST(73Am) or the pTacGST(73Am)-iodoTyrRS-mj-Nap3 was introduced into a BW25113RFzero-iy strain, and colony formation was checked on an LB plate containing 3-iodotyrosine. The result is shown in FIG. 16.

As is clear from FIG. 16, the RFzero-iy strain into which the pTacGST(73Am)-iodoTyrRS-mj-Nap3 was introduced ((b) of FIG. 16) had a much greater growth potential than the RFzero-iy strain into which the pTacGST(73Am) was introduced ((a) of FIG. 16). This has shown that, by increasing the efficiency of UAG translation, it is possible to improve the growth rate of a RFzero-iy strain.

Example 11

The foregoing examples have shown that, in order to increase the growth rate of a RFzero-iy strain, it is only necessary to express sucB properly and increase the efficiency of UAG translation. In view of this, in the present example, the effects of these factors on the growth rate were examined. Specifically, the effect of each factor on the growth rate was estimated from a growth curve.

First, the effect on a RFzero-iy strain derived from a HST08 strain was examined. A sucB gene whose stop codon had been replaced with UAA was ligated immediately downstream of an ampicillin-resistant gene, and the linked genes were cloned into pBR322 vector. Similarly, an iodoTyrRS-mj/Nap3 pair, alone or with a sucB expression system, was cloned into pBR322. Next, the RFzero-iy strain was transformed with pBR322 (vector), a sucB expression plasmid, and a sucB/iodoTyrRS-mj/Nap3 expression plasmid. The growth rates of the transformed strains were measured. For comparison, pBR322 or a aaRS/tRNA expression plasmid was introduced into a HST08 [BAC7gent supE44:: cat piodoTyrRS-MJR1-kan] strain, and the growth rate was measured in the same manner. The results are shown in FIG. 17.

Figure 17:
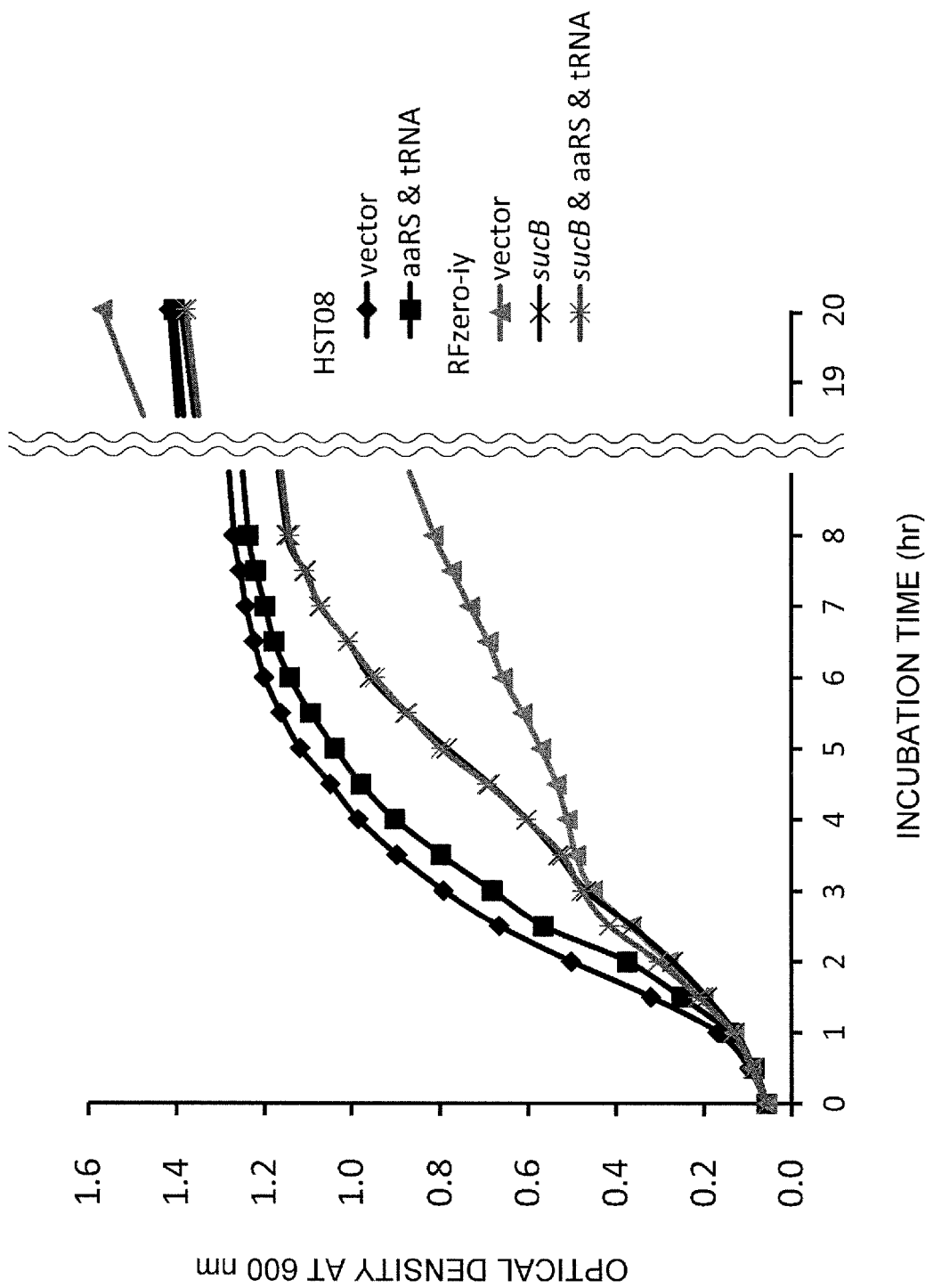
FIG. 17

As shown in FIG. 17, in the case where the pBR322 vector was introduced into the RFzero-iy strain, the same growth curve as shown in FIG. 6 was obtained. The growth rate decreased after the OD600 exceeded about 0.4, and thereafter kept growing at a constant rate. Note that, although the turbidity became greater than that of a wild type after 20 hours, there appeared to be many dead cells and it appeared that cell division did not stop properly. On the other hand, in the case where the sucB expression system was introduced into the RFzero-iy strain, the growth rate did not decrease even after the OD600 exceeded about 0.4, and finally the cells grew to the same extent as a wild-type HST08 strain. Note that, in the case where the iodoTyrRS-mj/Nap3 expression system was introduced in addition to the sucB expression system ("sucB & aaRS & tRNA" in FIG. 17), the growth rate did not increase any further, unlike BW25113 strains. In addition, no change was observed in the shape of a transformant colony. It is expected from this that, in the RFzero-iy strain derived from the HST08 strain, the efficiency of UAG translation is high enough.

Meanwhile, the following was confirmed. In a case where a iodoTyrRS-mj/Nap3 pair is overexpressed in a wild-type HST08 strain, cytotoxicity is not likely to appear although Nap3 mutants are overexpressed, as has been reported (Guo et al., Angew. Chem. Int. Ed. Engl., 2009, 48, 9148-9151.). Note, however, that the growth rate decreases a little.

Next, in the same manner as the RFzero-iy strain derived from the HST08 strain, the effect on a RFzero-iy strain derived from BW25113 was examined. Specifically, a BW25113 [BAC6-hemAK piodoTyrRS-MJR1-kan prfA:: zeo hemA(TAG→TAA)] strain was transformed with pBR322, with a sucB expression plasmid or with a sucB/ iodoTyrRS-mj/Nap3 expression plasmid, and the growth rate of each strain was measured. For comparison, pBR322 or an iodoTyrRS-mj/Nap3 expression plasmid was introduced into a BW25113 [BAC6-hemAK piodoTyrRS-MJR1-kan] strain, and the growth rate was measured in the same manner. The results are shown in FIG. 18.

Figure 18:
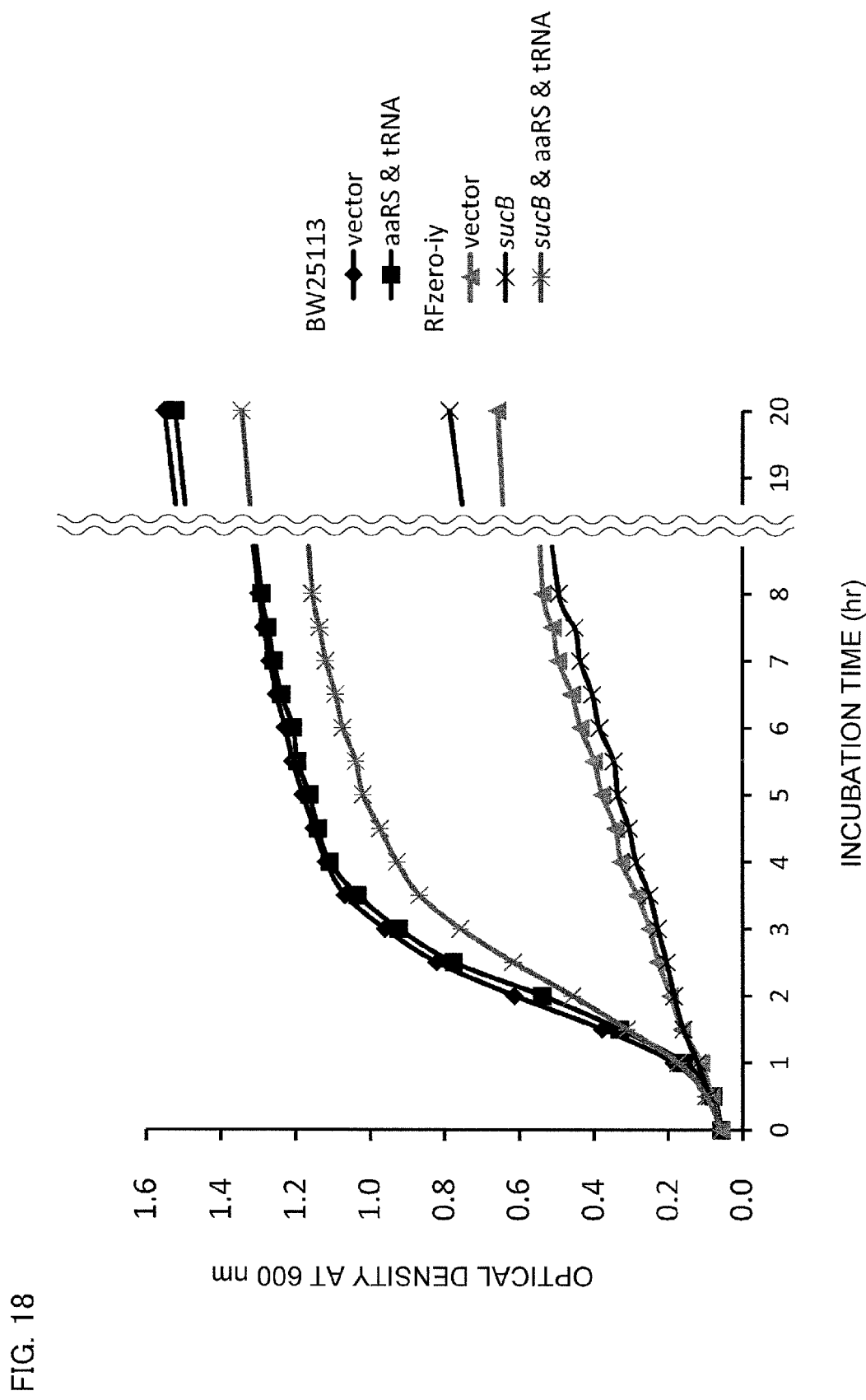
FIG. 18

As shown in FIG. 18, in a case where sucB was expressed in the RFzero-iy strain derived from BW25113, the growth rate did not increase but was kept constant. On the other hand, in a case where an iodoTyrRS-mj/Nap3 expression system was introduced in addition to the sucB expression system ("sucB & aaRS & tRNA" in FIG. 18), the growth rate dramatically recovered unlike the HST08 strain, and the growth curve observed was similar to those of wild-type strains although the RFzero-iy strain was a ΔprfA strain. Furthermore, the shape of a transformant colony was also very similar to those of the wild-type strains.

A comparison between the RFzero-iy strain produced from HST08 and the RFzero-iy strain produced from BW25113 showed that (i) the growth of a HST08RFzero-iy strain was inhibited not due to the insufficient efficiency of UAG translation but due to the low activity of sucB but (ii) the growth of a BW25113RFzero-iy strain was inhibited due to not only the low activity of sucB but also the insufficient efficiency of UAG translation. The comparison further showed the following. Regarding the BL21(DE3) strain, it is possible to produce a BL21(DE3)RFzero-iy strain with use of BAC7. Although the BL21(DE3)RFzero-iy strain can be cultured on a plate, in order for the BL21(DE3)RFzero-iy strain to be suited for usual gene operations including liquid culture, it is more desirable to recruit a sucB expression system by for example using BAC8 or introducing the sucB expression system in trans.

Example 12

In the present example, expression of a gst mutant, which contains a UAG codon in its ORF, was checked.

First, in a gst(73Am) mutant in pTacGST(73Am)-iodoTyrRS-mj-Nap3, a tyrosine codon in any of the 22nd, 57th, 141st, 155th and 163rd residues was further replaced with UAG. In this way, series in each of which UAG codons were introduced into two positions were produced. For comparison, a wild-type gst was cloned in the same manner, thereby producing pTacGST-iodoTyrRS-mj-Nap3. Either of the above series or pTacGST(73Am)-iodoTyrRS-mj-Nap3 or pTacGST-iodoTyrRS-mj-Nap3 was introduced into a BW25113RFzero-iy strain, and the expression of the full-length GST was detected by western blotting using anti-GST antibodies. The results are shown in FIG. 19.

Figure 19:
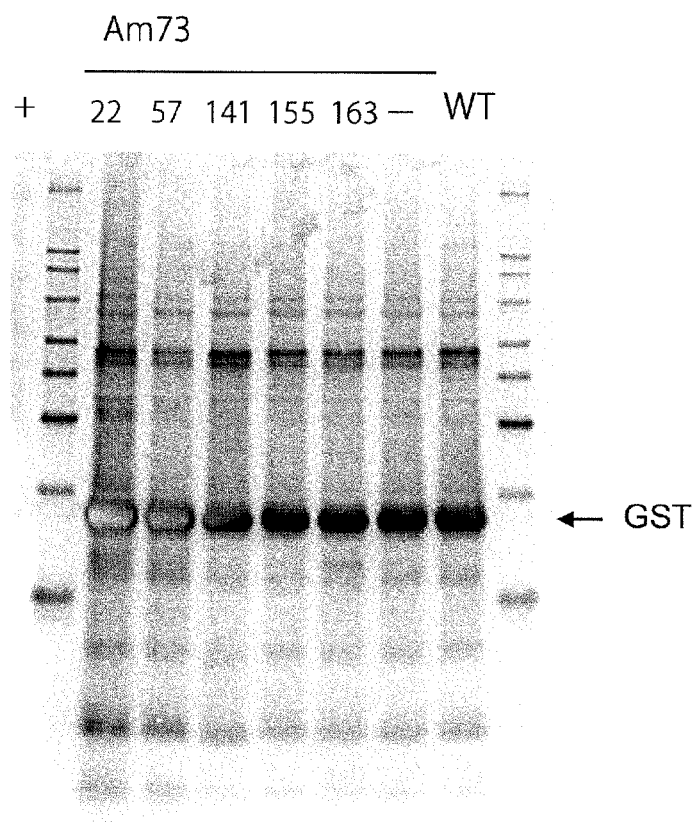
FIG. 19

As shown in FIG. 19, as compared to the wild-type gst, the full-length GST of the gst(73Am) mutant and the full-length GST of each of the gst(73Am) mutants into each of which a further UAG codon had been introduced were expressed to the same extent as the wild-type gst. That is, the results showed that the UAG codon was translated efficiently to 3-iodotyrosine. Furthermore, no fragment resulting from translation terminated at a position of UAG was detected. This showed that the UAG was totally changed to a sense codon.

Next, pTacGST(7Am)-iodoTyrRS-mj-Nap3 was produced, in which each of all codons specifying 1st (corresponding to gst(25Am)), 22nd, 57th, 73rd, 141st, 155th and 163rd amino acids of a gst gene was replaced with a UAG codon. This construct was introduced into a BW25113RFzero-iy strain, and expression of gst was checked. The result is shown in FIG. 20.

Figure 20:
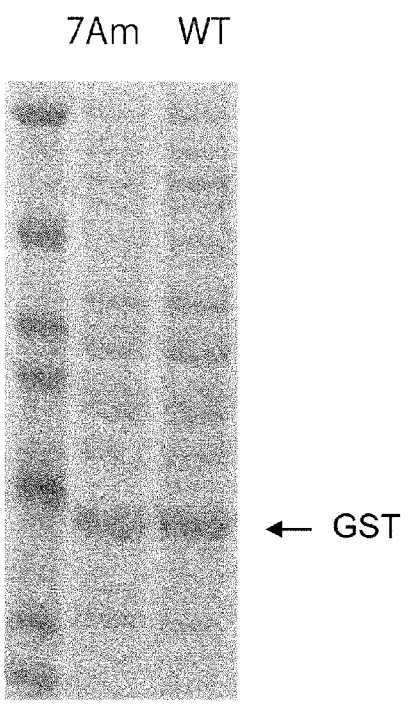
FIG. 20

As shown in FIG. 20, the expression levels of a wild-type gst and of gst(7Am) were compared by SDS-PAGE. The same degree of overexpression was observed. This clearly showed that the BW25113RFzero-iy strain was a biological species (i) which was equivalent to a wild-type strain in growth rate, (ii) whose efficiency of UAG translation was equivalent to that of tyrosine codon and (iii) in which a UAG codon was completely reassigned to 3-iodotyrosine.

Example 13

In the present example, non-natural amino acids were introduced by assigning UAG codons of a BW25113 strain to various tyrosine derivatives and lysine derivatives. Specifically, a non-natural amino acid was introduced by reassigning the UAG codons of the BW25113RFzero-iy strain produced in Example 6 to various tyrosine derivatives and lysine derivatives.

Figure 26:
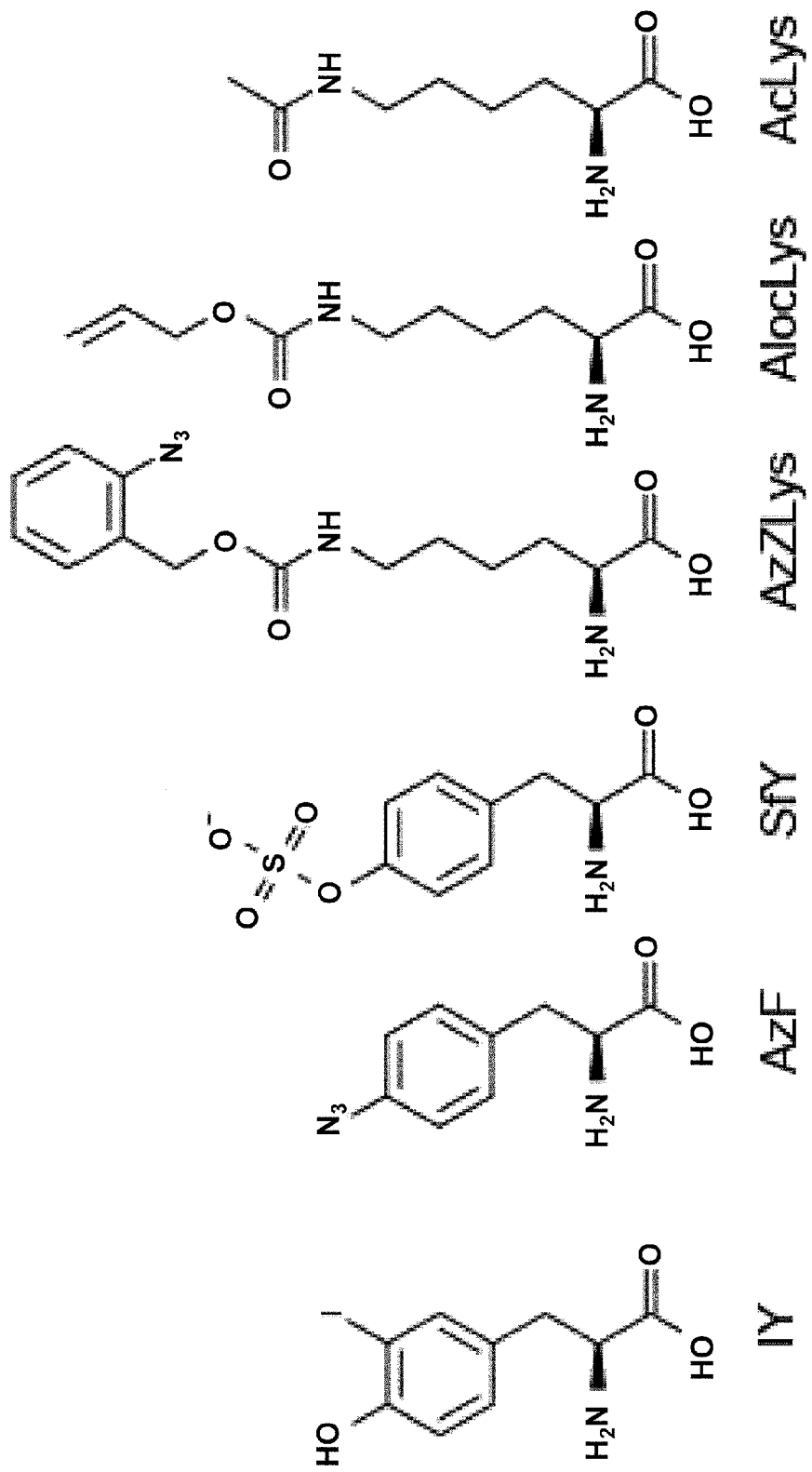
FIG. 26

Archaebacterial TyrRS and PylRS used in the present example were altered such that, in *Escherichia coli*, a desired non-natural amino acid is to be attached to tRNA that recognizes UAG codon. Specifically, those used in the present example were (i) a PylRS derivative (aforementioned AcKRS-3) which attaches AzFRS-mj of Example 8, SfYRS-mj of Example 8, and Nε-acetyl-L-lysine (AcLys) to their corresponding amber suppressor tRNA (*Methanosarcina mazei* tRNA$^{Pyl}$) molecules and (ii) a PylRS derivative (Yanagisawa T. et al, Chem, Biol, 15, pp 1187-1197 (2008)) which attaches Nε-allyloxycarbonyl-L-lysine (AlocLys) or Nε-(o-azidobenzyloxycarbonyl)-L-lysine (AzZLys) to its corresponding amber suppressor tRNA (*Methanosarcina mazei* tRNA$^{Pyl}$) molecule. FIG. 26 shows the structures of non-natural amino acids used in the present example.

Each RS derivative and its corresponding amber suppressor tRNA were expressed in BW25113RFzero-iy. Note that an endogenous system of RFzero-iy which translates UAG codon to 3-iodotyrosine does not function in the absence of 3-iodotyrosine. Therefore, by (i) introducing a construct which codes for another pair of RS derivative and tRNA, (ii) expressing the pair and (iii) adding a corresponding non-natural amino acid, it is possible to change the amino acid assigned to the UAG codon of the RFzero-iy from 3-iodotyrosine to a desired non-natural amino acid.

Figure 27:
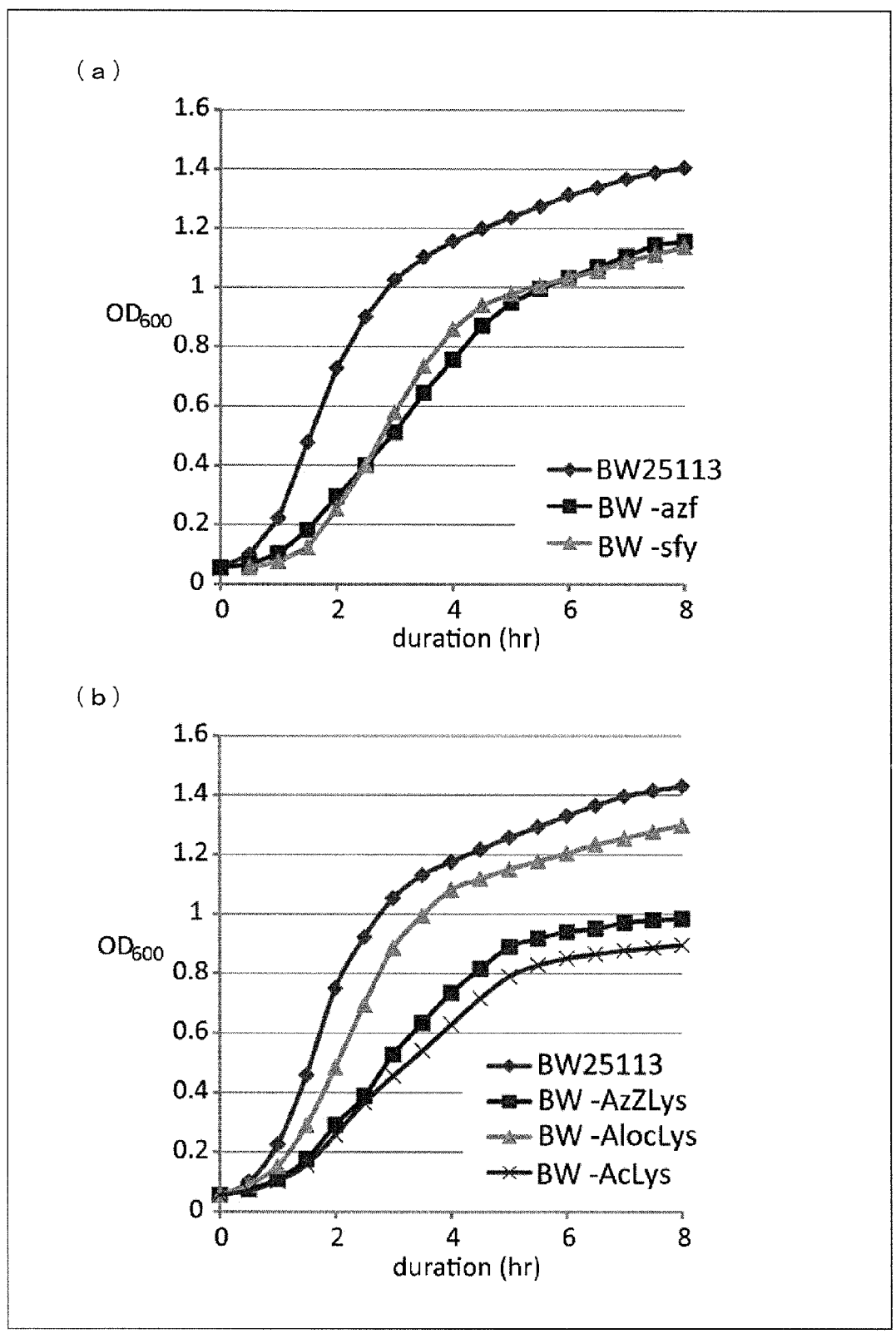
FIG. 27

Strains in which RS derivative-tRNA pairs had been expressed were grown in culture media containing their corresponding non-natural amino acids, and their growth rates were measured. The results are shown in FIG. 27. In the results, BW25113RFzero-iy strains (BW-azf, BW-sfy and BW-AlocLys in FIG. 27) which had RS derivative-tRNA pairs for introducing 4-azidophenylalanine, o-sulfotyrosine and Nε-allyloxycarbonyl-L-lysine, respectively, grew at substantially the same rate as their parent strain BW25113 in culture media containing their corresponding non-natural amino acids. On the other hand, BW25113RFzero-iy strains (BW-AzZLys and BW-AcLys in FIG. 27) which had RS derivative-tRNA pairs for introducing Nε-(o-azidobenzyloxycarbonyl)-L-lysine and acetyllysine, respectively, grew at a moderate rate as compared to their parent strain BW25113 in culture media containing their corresponding non-natural amino acids.

Figure 28:
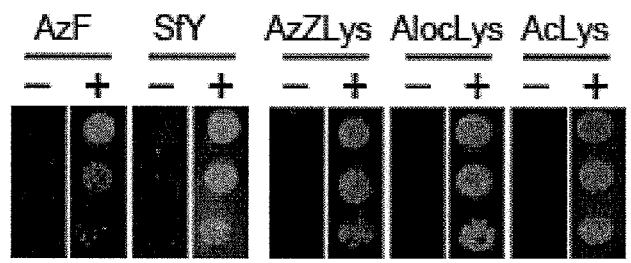
FIG. 28

Furthermore, how much the growth of each of the RFzero-iy strains depends on non-natural amino acids was checked. A cell culture incubated overnight was diluted, the diluted culture was spotted on (i) a non-selective LB culture medium containing a corresponding non-natural amino acid and (ii) a non-selective LB culture medium containing no corresponding non-natural amino acid, and the diluted culture thus spotted was further incubated. The results are shown in FIG. 28. As is clear from FIG. 28, the growth of all the RFzero-iy strains totally depended on the presence of a corresponding non-natural amino acid. This showed that the amino acid assigned to the UAG codon had been changed from 3-iodotyrosine to 4-azido-L-phenylalanine, O-sulfo-L-tyrosine, Nϵ-acetyl-L-lysine, Nϵ-allyloxycarbonyl-L-lysine, or Nϵ-(o-azidobenzyloxycarbonyl)-L-lysine.

The results have shown that it is possible to quickly reassign a codon in various genetic backgrounds by using various non-natural amino acids. The results have also shown that a produced RFzero strain grows quickly enough for large-scale protein production.

Example 14

In the present example, it was checked whether proteins, into which non-natural amino acids were introduced, were actually synthesized in RFzero strains obtained from BW25113. In the RFzero strains, amino acids assigned to the UAG codons have been changed to 3-iodotyrosine, 4-azidophenylalanine and o-sulfotyrosine, respectively (such RFzero strains are hereinafter referred to as BW25113RFzero-iy, BW25113RFzero-azf, and BW25113RFzero-sfy).

First, expression plasmids for expressing altered GST genes (gst(3×amb) and gst(7×amb)), each of which is the same as the GST gene except that three or seven of fifteen tyrosine codons have been changed to UAG codons, were produced. Each of the altered GST genes has 25 extra N-terminal amino acids. In the gst(3×amb) gene, tyrosine codons at positions 25, 47 and 98 (the numbering includes the 25 extra N-terminal amino acids) have been changed to UAG codons. In the gst(7×amb) gene, tyrosine codons at positions 82, 166, 180 and 188, in addition to the tyrosine codons at the positions of the gst(3×amb) gene, have been changed to UAG codons. The altered GST genes are under the control of tac promoter. Moreover, in each of the expression plasmids, an expression unit (RS derivative-tRNA pair) for changing an amino acid assigned to UAG codon to 3-iodotyrosine, 4-azidophenylalanine or o-sulfotyrosine has been incorporated.

Figure 29:
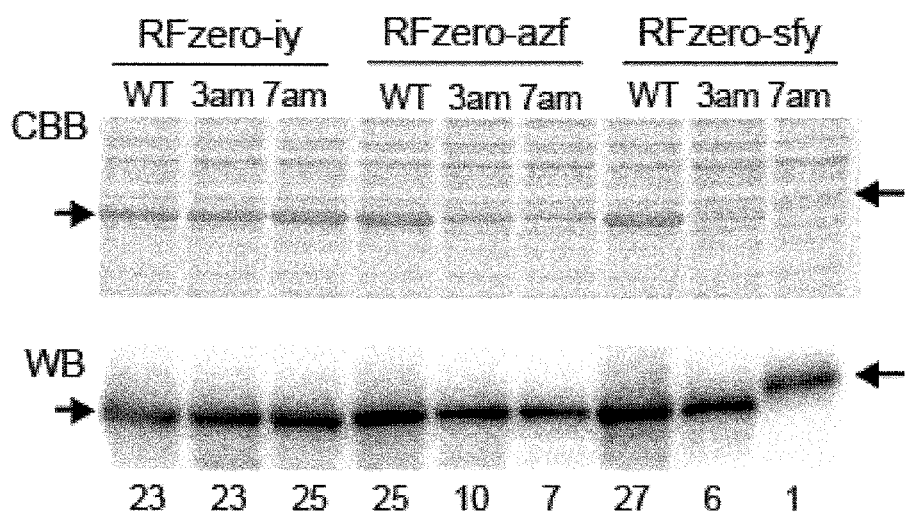
FIG. 29

Each of the expression plasmids was introduced into BW25113RFzero-iy produced in Example 6. A protein was obtained from each strain, subjected to SGS-PAGE, subjected to CBB staining, and was subjected to western blotting using an anti-GST antibody. The results are shown in FIG. 29. In FIG. 29, RFzero-azf and RFzero-sfy are strains obtained by introducing, into BW25113RFzero-iy strains, expression units for changing the amino acids assigned to the UAG codons to 4-azidophenylalanine and o-sulfotyrosine, respectively. Upper-row pictures in FIG. 29 show the results of CBB staining, and lower-row pictures in FIG. 29 show the results of western blotting. As shown in FIG. 29, it was confirmed that the full length of altered GST gene (arrow in FIG. 29) was expressed in each strain. Note that the "wild-type GST (WT)" in the present example refers to GST that has 25 extra N-terminal amino acids. The number below each lane indicates estimated yield (mg/l culture). The levels of expression of the gst(3×amb) and the gst(7×amb) in BW25113RFzero-iy were substantially the same as that of a wild-type GST. The levels of expression of the gst(3×amb) and the gst(7×amb) in BW25113RFzero-azf and BW25113RFzero-sfy were lower than that of the wild-type GST. However, even the gst(7× amb) of BW25113RFzero-sfy, which showed the lowest level of expression, produced a desired protein in a milligram-order amount per litter of cell culture.

Figure 30:
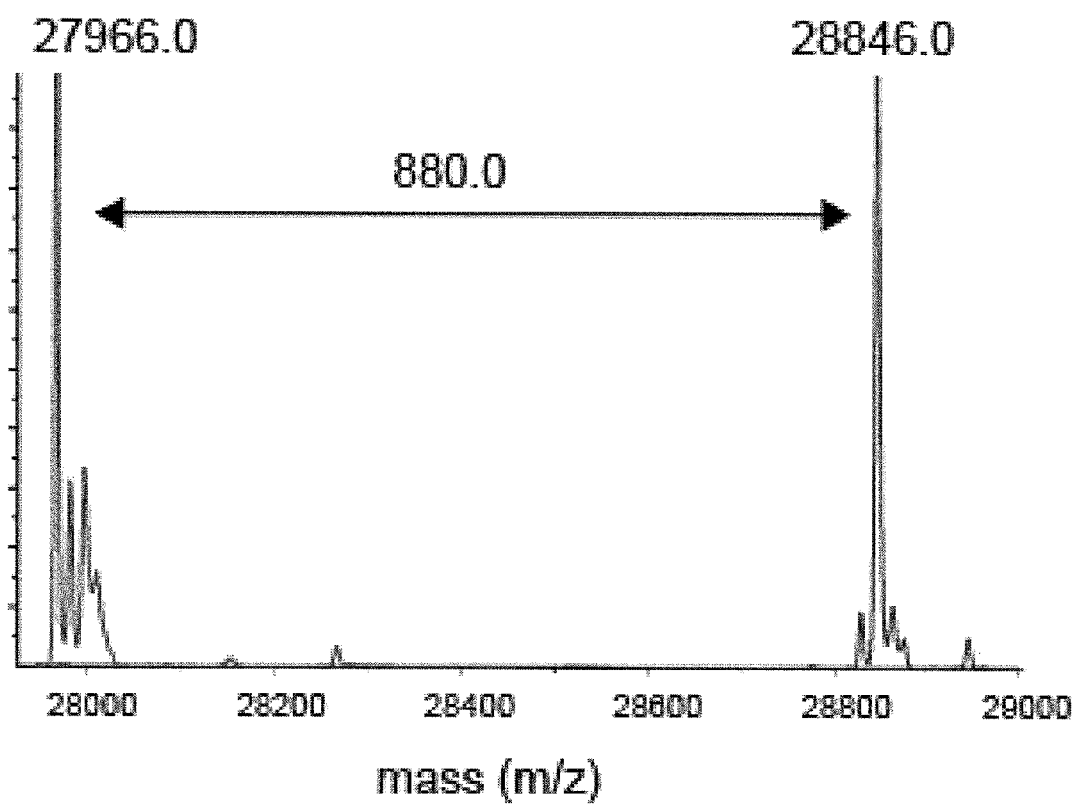
FIG. 30

Furthermore, the introduction of seven iodotyrosines in a protein was checked by mass spectrometry (ESI-MS) using a gst(7×amb) product in BW25113RFzero-iy. The result is shown in FIG. 30. As a result, the estimated mass (28846.0 Da) of GST protein derived from BW25113RFzero-iy was found to be greater by 880 Da than the estimated mass (27966.0 Da) of a wild-type GST protein. This difference is equivalent to the value obtained when seven hydrogen atoms are replaced with iodine atoms. That is, it was confirmed that each of the seven tyrosines had been replaced with 3-iodotyrosine.

It has been known that translation machinery or assimilation mechanism works on various non-natural amino acids with different efficiencies (Liu, C. C. and Schultz, P. G., Annu. Rev. Biochem., 79, 413-444 (2010)). In view of this, the reason why the yields of proteins decreased seems that the speed of protein synthesis using 4-azidophenylalanine and o-sulfotyrosine was lower than that using 3-iodotyrosine. This was also confirmed by the following experiment using a prfA+ strain.

Figure 31:
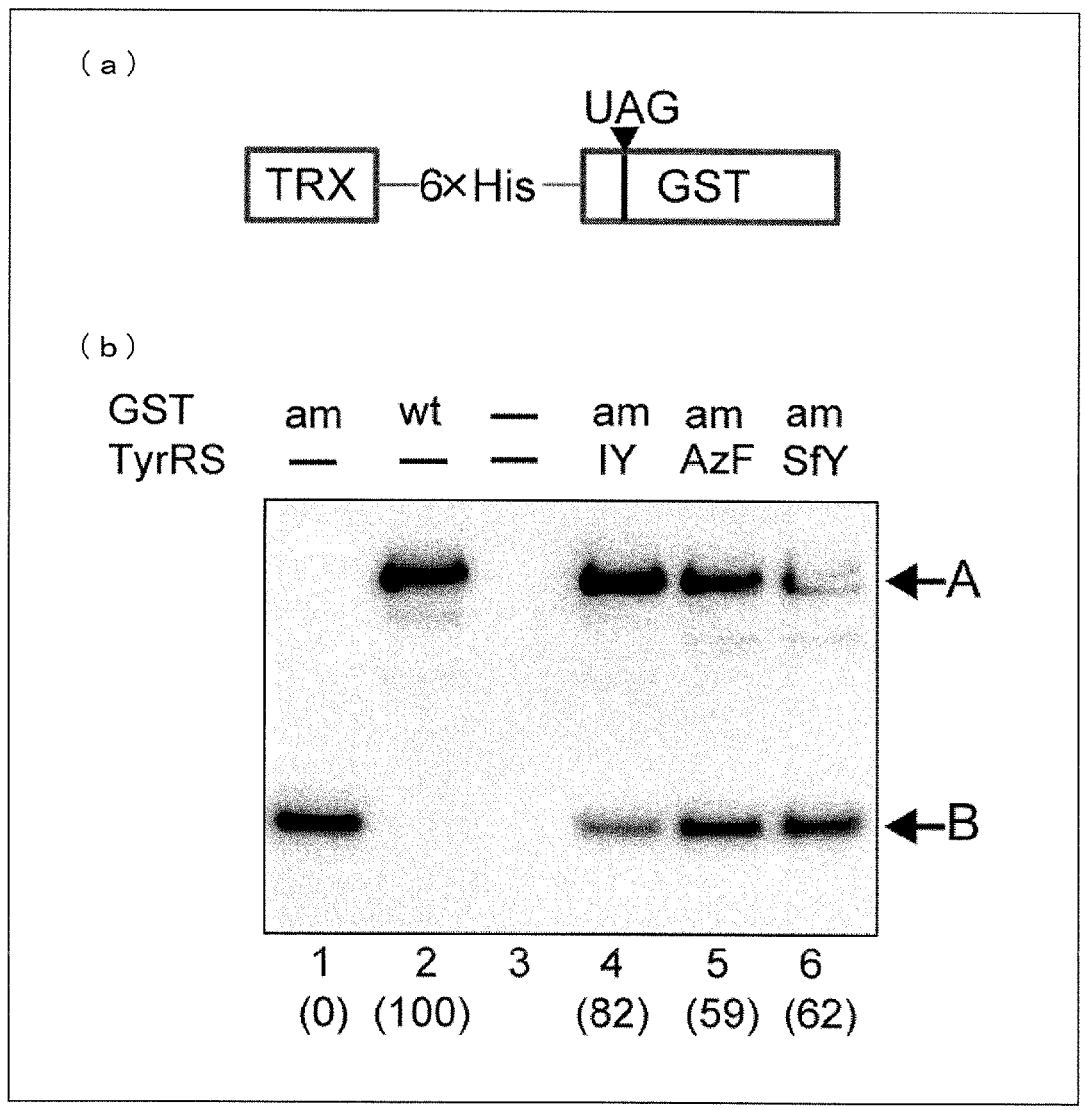
FIG. 31

In this experiment, a GST gene containing a UAG codon near the N terminal was introduced, together with an expression unit for introducing a non-natural amino acid, into BW25113 which was a prfA+ strain. Then, the efficiency of translation was checked. The GST gene containing a UAG codon near the N terminal is incorporated in a plasmid so that a fusion protein of the GST and thioredoxin (TRX) is produced (refer to (a) of FIG. 31). The result is shown in (b) of FIG. 31. (b) of FIG. 31 shows the result of western blotting using an anti-His tag antibody. In (b) of FIG. 31, Lane 2 shows a strain in which a GST gene containing no in-frame UAG codon has been introduced, and Lanes 1 and 4 to 6 each show a strain in which a fused GST gene containing a UAG codon near the N terminal has been introduced. The strain shown in Lane 1 contains no construct that introduces a non-natural amino acid. As is clear from Lanes 4 to 6, strains into each of which a construct for assigning a UAG codon to 3-iodotyrosine, 4-azidophenylalanine or o-sulfotyrosine has been introduced generate total-length fusion proteins in the presence of corresponding non-natural amino acids (see arrow A in (b) of FIG. 31). Further, in these strains, proteins resulting from termination of translation at the UAG codon were also produced (see arrow B in (b) of FIG. 31). The number in parentheses below each lane indicates the percentage (%) of total-length fusion protein with respect to the sum of the proteins resulting from termination of translation and the full-length fusion protein thus produced. That is, the number indicates the efficiency of non-natural amino acid introduction at the UAG codon. It has been found that two tyrosine derivatives (4-azidophenylalanine and o-sulfotyrosine) are introduced with a lower efficiency than 3-iodotyrosine even under the prfA+ condition. Note that, also in a case where a protein becomes unstable due to introduction of non-natural amino acids into the larger number of positions, the yield of the protein will probably decrease.

Example 15

In the present example, a histone containing acetyllysines in a plurality of particular positions was produced by using a BL21(DE3)RFzero-iy strain. In histone H4, up to four specific lysines of ten lysine residues are acetylated after translation. A method for synthesizing a homogeneous histone modified at specific positions is useful for studies on epigenetics and development of medicine which acts on chromosome reconstruction.

Specifically, a cell extract was prepared from the BL21 (DE3)RFzero-iy strain produced in Example 6, and a desired protein was produced by using a cell-free protein-synthesizing system using the cell extract. It is possible to directly add a high concentration of nicotinamide to the cell-free protein-synthesizing system. Therefore, in the cell-free protein-synthesizing system, it is possible to prevent deacetylation, thereby obtaining a histone homogeneous as to acetylation. Furthermore, a cell extract prepared from a BL21 strain is known to show high protein productivity (Kigawa, T. et al, J. Struct. Funct. Genomics, Vol. 5, pp 63-68 (2004)).

First, a cell extract was prepared from BL21(DE3)RFzero-iy, and thereafter was dialyzed to remove 3-iodotyrosine. Next, (i) a PylRS derivative derived from Methanosarcina mazei, which PylRS derivative attaches acetyllysine to tRNA and (ii) amber suppressor tRNA which corresponds to the PylRS derivative were added to the cell extract. Further, nicotinamide was added at a final concentration of 10 mM.

An expression plasmid was constructed with use of an altered gene that codes for human histone H4, which gene was the same as a gene that codes for human histone H4 except that codons corresponding to four positions (positions 5, 8, 12 and 16) to be acetylated had been all replaced with UAG. Note that a peptide tag (MKDHLIHNHHKHEHA-HALVPRGSH: SEQ ID NO: 31) is added to the N terminal of a protein produced by the altered gene. The expression plasmid was added to the cell extract.

Synthesized H4 histone protein was obtained as an insoluble fraction. The H4 histone protein was dissolved with urea, and the H4 histone thus dissolved was subjected to chromatography for purification.

Figure 32:
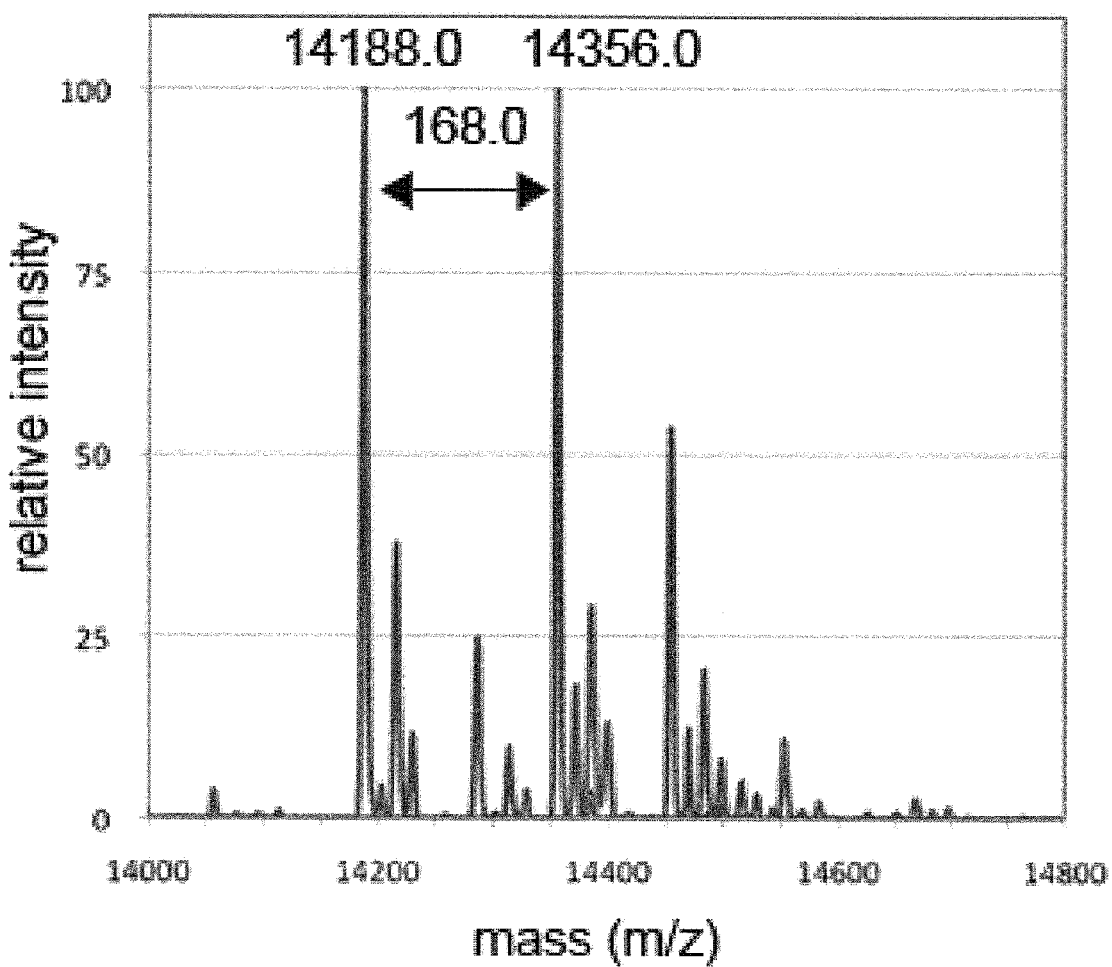
FIG. 32

As a result, it was confirmed that total-length H4 histone was produced. The yield of the total-length H4 histone was 0.3 mg per 1 ml of reaction solution. Furthermore, introduction of acetyllysine in H4 histone was checked by mass spectrometry (ESI-MS). The result is shown in FIG. 32. As a result, the estimated mass (14356.0 Da) of obtained H4 histone was greater by 168.0 Da than the estimated mass (14188.0 Da) of unmodified H4 histone. This difference corresponds to the addition of four acetyl groups (168.1 Da in total). That is, the result showed that four acetyl groups had been introduced into histone H4.

Reference Example

In this reference example, a method for improving a growth potential of a RFzero-q strain by altering a tRNA molecule for translating a UAG codon is introduced.

(Creation of supE tRNA Molecule with Higher UAG Translation Efficiency)

As described in Example 1, a Cm resistance level of a RFzero-q strain transformed with a cat(10Am) was lower than that of a RFzero-q strain transformed with a wild-type cat. This is probably because that translation efficiency of the UAG codon by the amber suppressor mutant tRNA of glutamine was lower than translation efficiency of a glutamine codon (CAA, CAG) by a normal glutamine tRNA. It is known that when a mutation is introduced into the third nucleotide of anticodon of tRNA$^{Gln}$, which position of the third nucleotide of anticodon corresponds to the supE44 mutation, the aminoacylation activity decreases. The RFzero-q strain derived from the HST08 strain has the supE44 gene coding for an amber suppressor tRNA$^{Gln}$ (supE tRNA), and the third nucleotide (position 36) of anticodon (CUG) of the tRNA$^{Gln}$ is mutated (G to A). Considering these facts, improvement of growth potential of the RFzero-q strain by improving UAG translation efficiency of the supE tRNA molecule instead of altering an aminoacylation tRNA synthetase was attempted.

Figure 21:
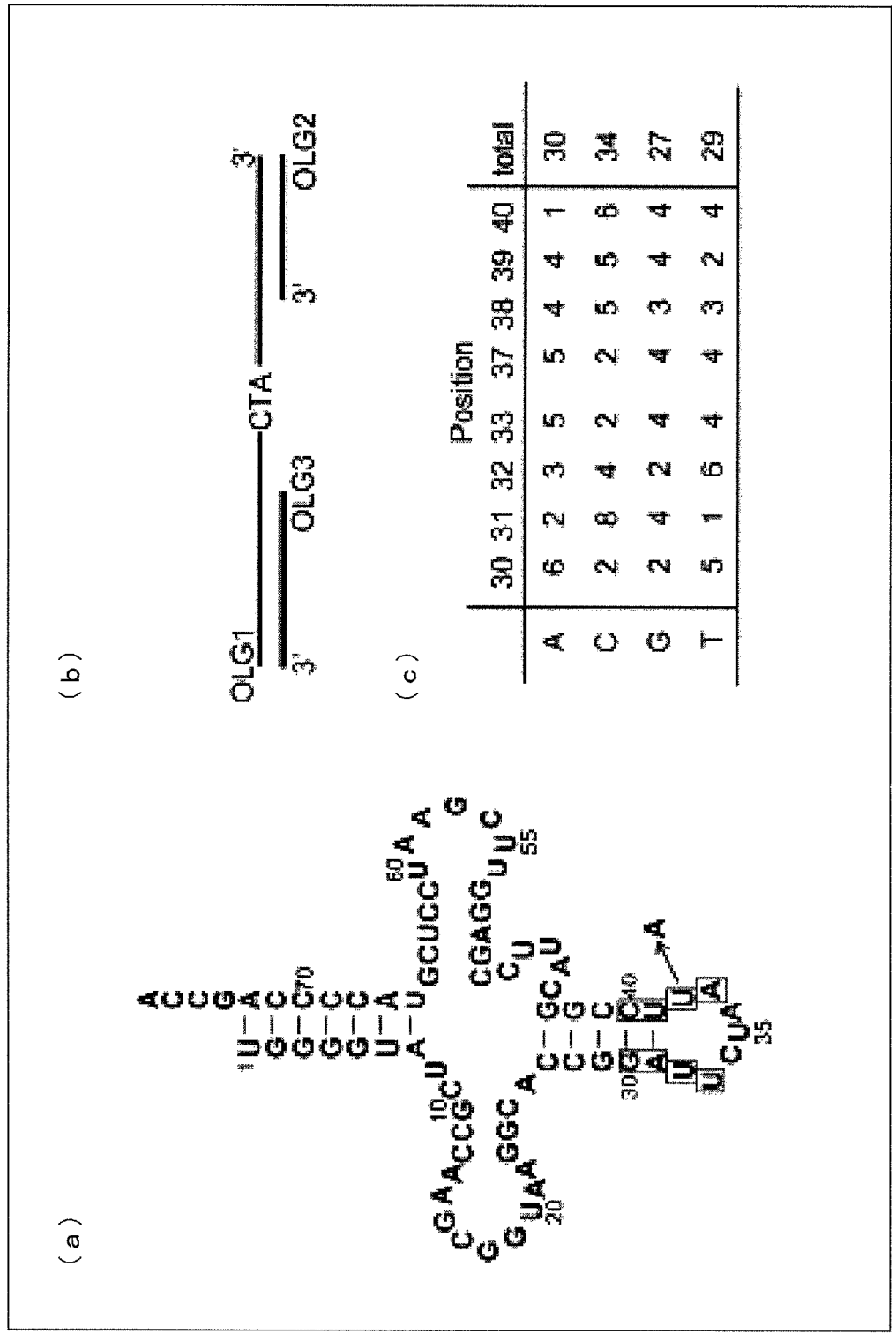
FIG. 21

As shown in (a) of FIG. 21, a library of supE tRNA mutants was constructed by randomizing positions 30-40 of a supE tRNA gene except the anticodon moiety (positions 34, 35, and 36). The following process was carried out with three DNA oligomers, OLG1 (position 28), OLG2 (position 29), and OLG3 (position 30) so as to form a double-stranded DNA.

The OLG1 and OLG2 oligomers (200 pmol each) were separately phosphorylated at the 5' end by adding the oligomer in a reaction mixture (20 ml) containing 50 mM Tris-HCl (pH8.0), 10 mM MgCl$_2$, 10 mM 2-mercaptoethanol, 4.7 mM ATP, and T4 polynucleotide kinase (10 units), and subjecting the oligomer to a temperature of 37° C. for 30 minutes. These oligomers were mixed together, and the OLG3 (200 pmol) was added to the mixture of them. The resultant mixture was then subjected to annealing. The annealing was performed by heating at 94° C. for 0.5 minutes, 80° C. for 1 minute, 74° C. for 1 minute, 65° C. for 0.5 minutes, and 55° C. for 1 minute. The annealed oligomers were purified by simple gel filtration to remove the ATP.

An antisense strand had a gap corresponding to the anticodon moiety (CTA) and eight randomized sequences (see (b) of FIG. 21). This gap was filled by intracellular DNA polymerase after the transformation.

After these mutant genes were incorporated in the downstream of a tyrT promoter, the gene was then cloned to a pKS3cat(3amb)-kan carrying a mutant cat gene (cat(3Am)) and three in-frame UAG codons. Transformation was carried out with the resulting plasmid, thereby obtaining a DH10B strain lacking a suppressor tRNA. The DH10B was then subjected to selection of colonies on an LB plate containing kanamycin (30 µg/ml). As a result, 2×10$^7$ colonies (the library of supE tRNA mutants) were obtained. Then, sequencing was performed for twenty three of the clones, thereby finding that 15 of them (65%) contained complete tRNA sequences, whereas the others either lacked the entire tRNA sequence or had nucleotides missing in the randomized region (see (c) of FIG. 21).

Next, the library of supE tRNA mutants was screened on the LB plate containing Cm at 150 µg/ml, whereby 18 clones were generated. These clones were then tested for Cm resistance capacity with LB plates containing Cm at 150-500 µg/ml. Sequencing of the 18 clones found 13 different tRNA base sequences. All of the supE-tRNA mutants showed higher levels of Cm resistance than the parent supE tRNA. This result suggests that these mutants have greater UAG translation efficiency than the parent supE tRNA. All of these mutants had U33, A37, and a base pair between positions 30 and 40. These three features are probably necessary for efficient UAG translation.

Among the 13 different clones, clones 2, 3, 4, 5, 7, 9, and 11 showed highest levels of Cm resistance. Clone 3 was identical to the parent supE tRNA, except for a U-to-A substitution at position 38. This substitution was present in six of the highest-ranking clones showing higher Cm resistance, except for clone 2, suggesting that the substitution can further improve the UAG translation efficiency.

Among these clones, clones 4 and 7 are most greatly different from the parent tRNA, with six base substitutions at the eight randomized positions. In order to achieve more efficient UAG translation in the RFzero strain by using clones 3 and 7, with the smallest and largest numbers of mutations, respectively (hereinafter, clones 3 and 7 are referred to as "supE3 tRNA" and "supE7 tRNA", respectively). These two supE tRNA mutants had a U-to-A substitution at position 38 in common. However, U at this position was invariant between the two Escherichia coli tRNA$^{Gln}$, and was involved in the recognition of tRNA$^{Gln}$ by glutaminyl-tRNA synthetase. In fact, the U-to-G substitution at this position in the Escherichia coli tRNA$^{Gln}$ reportedly decreased the aminoacylation activity. Therefore, the efficient UAG translation by the supE3 and supE7 tRNAs is probably because an ability to recognize UAG was enhanced enough to compensate for a possible decrease in the aminoacylation activity.

(Creation of Efzero Strains with supE3 and supE7 tRNAs)

In the HST08 strain, the parent strain of the RFzerp-q strain, the supE-tRNA coding sequence was replaced with the supE3 or supE7 so as to create the HST08-3 and HSTC$_{8-7}$ strains. Homologous recombination was carried out using a RT/ET kit (Gene Bridges GmbH) The prfA gene was knocked out after introducing a BAC7gent having gentamicin resistance into the HST08-3 and HST08-7 strains, thereby to create RFzero-q3 and RFzero-q7. Note that, in this Example, a major part of prfA gene sequence was replaced with a Zeocin-resistant gene. Finally, by sequencing the prfA moiety on genomes of the HST08-3 and HST08-7 strains, it was confirmed that there were no prfA genes remaining in the genomes.

(Comparison of Translation Efficiency for Translating a UAG Codon)

In order to examine if the UAG translation efficiency was improved, a cat(13Am) in which all 13 of the glutamine codons on the cat gene were replaced with UAG was introduced into the RFzero-q3 and RFzero-q7 strains, respectively. It was confirmed that the RFzero-q3 and RFzero-q7 strains exhibited Cm resistance at 200 μg/ml. This was lower than Cm resistance (400 μg/ml) in the HST08 and RFzero-q strains transformed with pACYC184 carrying the wild-type cat gene. Meanwhile, the RFzero-q3 strain exhibited a Cm resistance of 400 μg/ml approximately. These results suggested that the UAG translation efficiency was dramatically improved in the RFzero-q3 strain.

Figure 22:
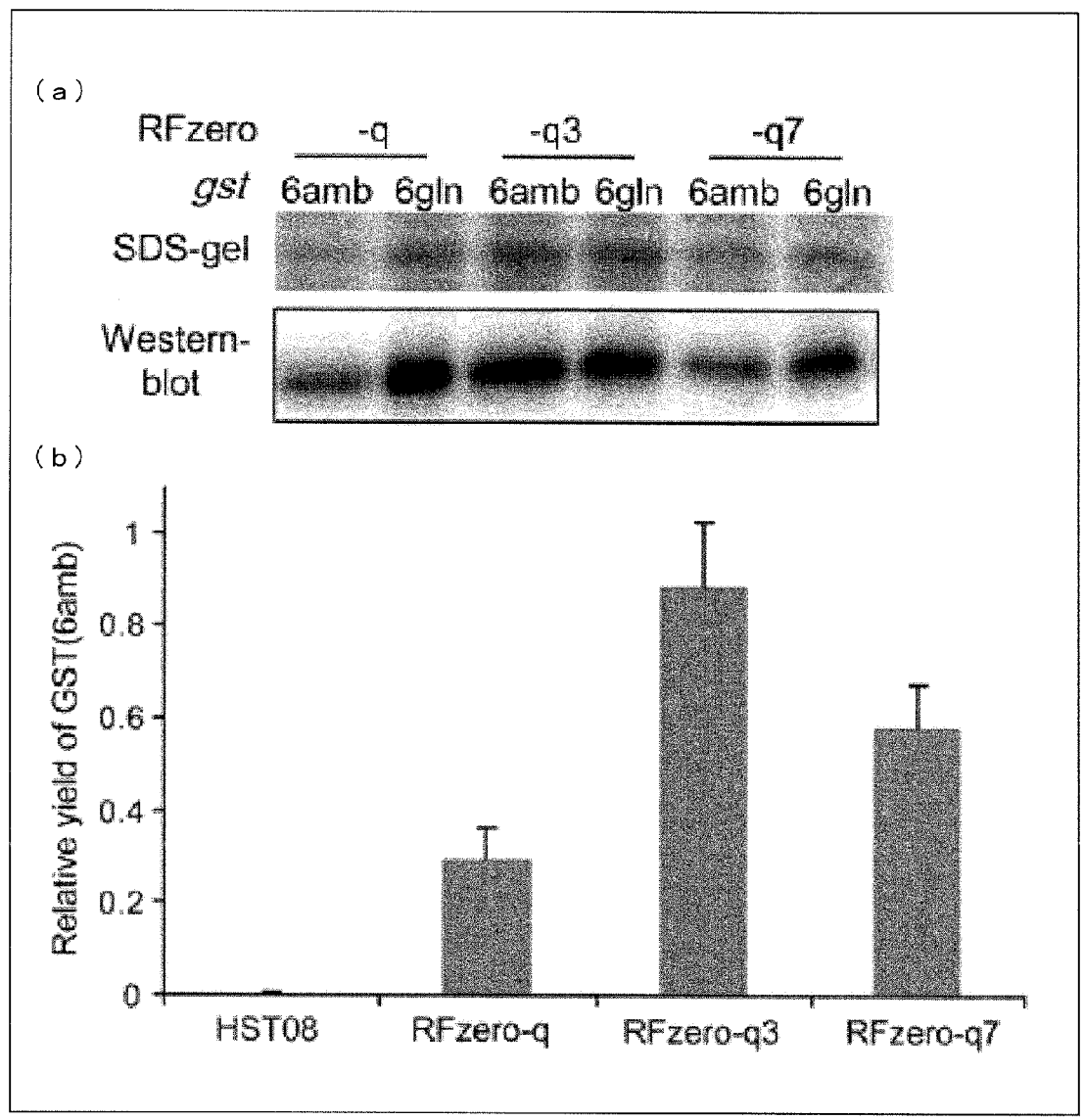
FIG. 22

Next, comparison between translation efficiency of UAG redefined as a glutamine codon and a glutamine codon (CAG) was carried out. The RFzero-q, RFzero-q3, and RFzero-q7 strains were transformed with a pTacGST(6Am) created by introducing six UAG codons (gst(6amb)) at the N-terminal of glutathione S-transferase (GST) gene and connecting the UAG codons to the downstream of a tac promoter. As controls, RFzero-q, RFzero-q3, and RFzero-q7 strains transformed with a pTacGST(6gln) incorporated with CAG in place of the six UAG codons were prepared. The expression of gst(6amb) and gst(gln) were analyzed by SDS-PAGE and Western-Blot. (A) of FIG. 22 shows the result. The yield of the RFzero-q strain in which gst(6amb) was expressed was lower than the yield of the RFzero-q strain in which gst(6gln) was expressed. This finding confirmed the previous observation that the translation efficiency for translating UAG was lower than the translation efficiency for translating glutamine codons (CAA and CAG) by normal glutamine tRNA. On the other hand, the expression yields of gst(6amb) and gst(6gln) were similar to each other in the RFzero-q3 strain, whereas the expression yields of gst(6amb) was slightly lower than that of gst(6gln) in the RFzero-q7 strain. The expression yields of the gst(6gln) in the RFzero-q strain and the RFzero-q7 strain were smaller than that of the RFzero-q3. This is probably because the growth rate of the RFzero-q3 strain is faster than the RFzero-q strain and the RFzero-q7, as described below.

Then, the relative yield of the gst(6amb) to the gst(6gln) was quantified by measuring the GST activity in the cellular extract. (b) of FIG. 22 shows the result.

As shown in (b) of FIG. 22, the gst(6amb) gene was hardly expressed in the parent HST08 strain with the intact prfA gene, although the supE tRNA gene was expressed therein. The yield of the gst(6amb) was drastically increased with the prfA knockout in the RFzero-q strain, the RFzero-q3 strain, and the RFzero-q7 strains. The relative yield was 29% (RFzero-q strain), 59% (RFzero-q7 strain) and 89% (RFzero-q3 strain), respectively. The yields of the gst(6amb) and gst (6gln) were almost identical to each other in RFzero-q3. These results indicated that the efficiency of UAG translation was significantly improved in both of RFzero-q3 and RFzero-q7 strains, and that the RFzero-q3 strain was improved to be able to translate UAG almost as efficiently as the glutamine codons (CAA and CAG).

(Comparison of Growth Rates Between HST08 Strain and RFzero-q Strains)

Figure 23:
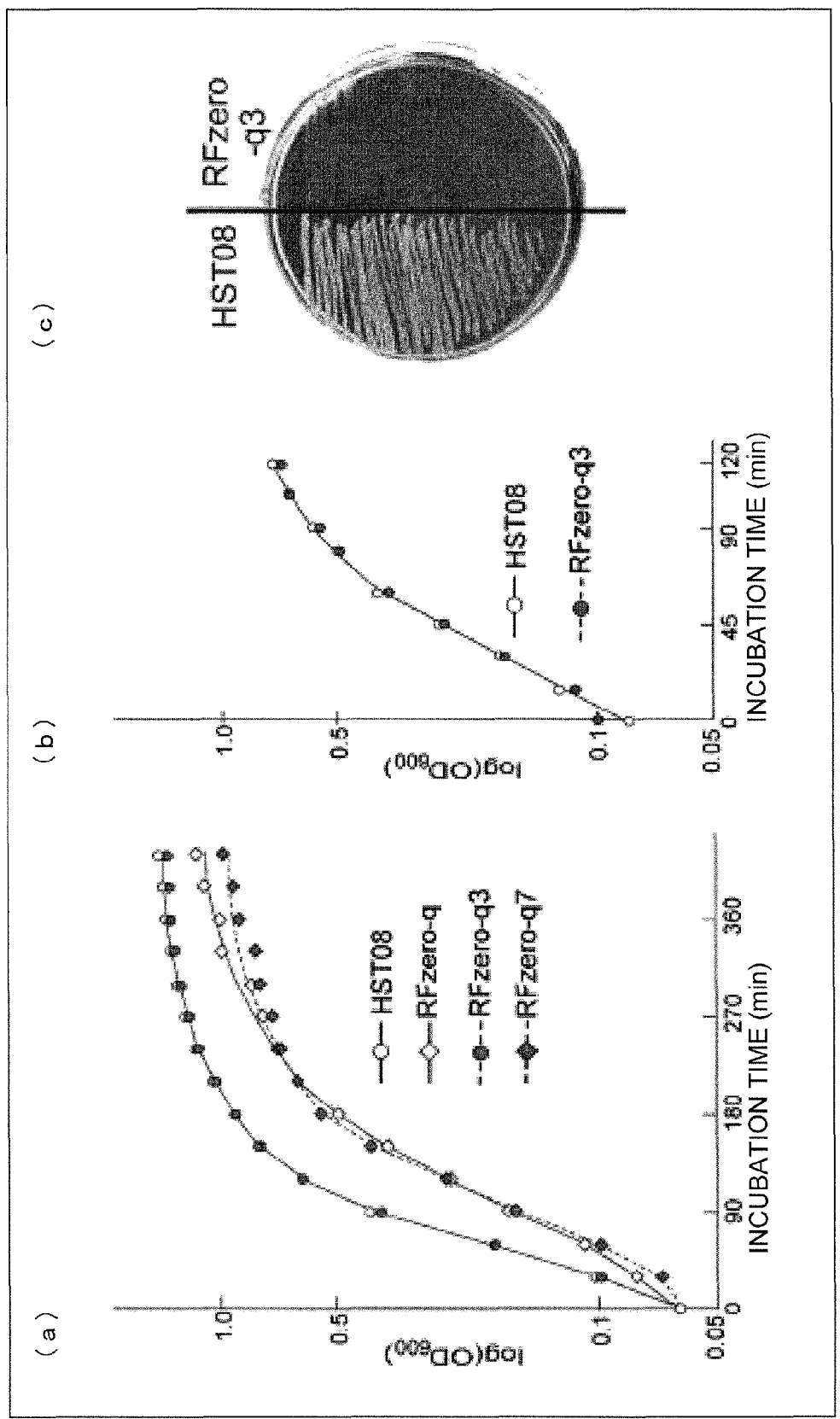
FIG. 23

The growth rates of the HST08 and RFzero-q strains were compared by culturing the HST08 and the RFzero-q strains in LB medium (without antibiotics) at 37° C., respectively. (a) of FIG. 23 shows the result. The RFzero-q strain grew slower than the parent HST08 strain, and the RFzero-q7 strain exhibited no improvement in the growth rate, as compared with the RFzero-q strain. On the other hand, the growth rate of the RFzero-q3 strain was indistinguishable from that of the HST08 strain, thereby indicating that the supE3 mutation has a favorable effect on the growth of Escherichia coli.

In the RFzero strains, RF-2, encoded by a prfB gene, is the only release factor, and recognizes UAA and UGA codons. A mutation in RF-2 reportedly allows the RF-2 to translate UAG, in addition to UAA and UGA. If this RF-2 mutation were present in the RF-2 of the RFzero-q strain, the activity of missing RF-1 would be restored by the RF-2. Thus, in order to confirm that the improvement of the growth rates was not due to the RF-2 mutation, the prfB locus in on the genome of the RFzero-q3 strain was sequenced. As a result, it was confirmed that no mutation had occurred in the prfB locus.

Furthermore, the comparison of the growth rates of the HST08 and RFzero-q3 strains under more unfavorable conditions was carried out. (b) and (c) of FIG. 23 show the result. First, these strains, which showed logarithmic growth in LB medium at 37° C., were transferred to a higher temperature, 42° C. to compare the growth rates. They maintained the logarithmic growth after the temperature shift for 1 hour, with minimal changes in the growth rate, however their growth rates were almost identical to each other for 2 hours after the temperature shift (see (b) of FIG. 23). On the other hand, the HST08 strain grew slowly on a poor nutrient medium containing only M9 salts, glycerol, and magnesium salt, whereas the RFzero-q3 strain could hardly grow on the poor nutrient medium (see (c) of FIG. 23), it was probably because the readthrough of the UAG codon reduced the activities of some genes important for growth under poor nutrient conditions.

INDUSTRIAL APPLICABILITY

According to the present invention, it is possible to apply a non-natural protein synthesis to a daily basic technology. The present invention is expected to contribute to improvements in production of drugs, analysis of protein functions, and alteration of enzymes and Escherichia coli, and the like.

The invention claimed is:

1. A method of producing a recombinant bacterium for production of a non-natural protein, comprising the steps of:
   (1) expressing tRNA in a bacterium, which tRNA recognizes UAG codon;
   (2) expressing an aminoacyl-tRNA synthetase in a bacterium, which aminoacyl-tRNA synthetase acylates the tRNA with a non-natural amino acid or an α-hydroxy acid;
   (3) subjecting a bacterium to a process for expressing, in the absence of a release factor for terminating translation at UAG codon, a function of at least one gene selected from the group consisting of genes each of which loses its function when a gene that codes for the release factor is defective; and
   (4) causing the gene that codes for the release factor in a bacterium to be defective,
   the bacteria in the steps (1) through (4) being identical, and
   the process being (i) a process of introducing, into the bacterium, a DNA construct for expressing the function of said at least one gene in the absence of the release factor and/or (ii) a process of introducing, into said at least one gene in a chromosome of the bacterium, an alteration for expressing the function of said at least one gene in the absence of the release factor,
   the DNA construct including an altered gene of said at least one gene in which altered gene a stop codon of said at least one gene has been changed from an amber codon (UAG) to an ochre codon (UAA) or to an opal codon (UGA),
   the alteration changing the stop codon of said at least one gene in the chromosome of the bacterium from the amber codon (UAG) to the ochre codon (UAA) or to the opal codon (UGA).

2. A method of producing a recombinant bacterium for production of a non-natural protein, comprising the steps of:
   (5) expressing, in a bacterium which expresses tRNA that recognizes UAG codon, an aminoacyl-tRNA synthetase that acylates the tRNA with a non-natural amino acid or an α-hydroxy acid;
   (6) subjecting the bacterium to a process for expressing, in the absence of a release factor for terminating translation at UAG codon, a function of at least one gene selected from the group consisting of genes each of which loses its function when a gene that codes for the release factor is defective; and
   (7) causing the gene that codes for the release factor in the bacterium to be defective,
   the process being (i) a process of introducing, into the bacterium, a DNA construct for expressing the function of said at least one gene in the absence of the release factor and/or (ii) a process of introducing, into said at least one gene in a chromosome of the bacterium, an alteration for expressing the function of said at least one gene in the absence of the release factor,
   the DNA construct including an altered gene of said at least one gene in which altered gene a stop codon of said at least one gene has been changed from an amber codon (UAG) to an ochre codon (UAA) or to an opal codon (UGA),
   the alteration changing the stop codon of said at least one gene in the chromosome of the bacterium from the amber codon (UAG) to the ochre codon (UAA) or to the opal codon (UGA).

3. The method according to claim 1, wherein, in the bacterium, another tRNA which recognizes UAG codon but is not acylated by the aminoacyl-tRNA synthetase is expressed, said method further comprising the step of causing a gene that codes for said another tRNA to be defective.

4. The method according to claim 1, wherein the non-natural protein is a non-natural protein that includes the non-natural amino acid or the α-hydroxy acid.

5. The method according to claim 1, wherein the bacterium is *Escherichia coli*.

6. The method according to claim 1, wherein said at least one gene is at least one, defect of which alone is lethal, among all genes whose translation is terminated at UAG codon.

7. The method according to claim 6, wherein:
the bacterium is *Escherichia coli*; and
said at least one gene is at least one gene selected from the group consisting of coaD, murF, hda, mreC, hemA, lpxK and lolA of *Escherichia coli*.

8. The method according to claim 7, wherein said at least one gene is any six genes selected from the group consisting of coaD, murF, hda, mreC, hemA, lpxK and lolA of *Escherichia coli*.

9. The method according to claim 7, wherein said at least one gene is coaD, hda, mreC and hemA genes of *Escherichia coli*.

10. The method according to claim 6, wherein said at least one gene further includes another gene, defect of which causes a reduction in growth rate of the bacterium.

11. The method according to claim 10, wherein said another gene defect of which causes a reduction in growth rate of the bacterium is a sucB gene of *Escherichia coli*.

12. The method according to claim 1, wherein:
the bacterium is *Escherichia coli*; and
the DNA construct is a DNA construct which expresses a function of at least one gene selected from the group consisting of coaD, murF, hda, mreC, hemA, lpxK and lolA of *Escherichia coli*.

13. The method according to claim 12, wherein the DNA construct further expresses a function of a sucB gene of *Escherichia coli*.

14. The method according to claim 1, wherein the DNA construct is selected from a bacterial artificial chromosome, a plasmid, and linear DNA, each of which is recruited in trans and/or in cis to the chromosome of the bacterium.

15. A DNA construct for producing a recombinant bacterium for production of a non-natural protein, which DNA construct expresses, in the presence of (i) tRNA that recognizes UAG codon and (ii) an aminoacyl-tRNA synthetase which acylates the tRNA with a non-natural amino acid or an α-hydroxy acid but in the absence of a release factor for terminating translation at UAG codon, a function of at least one gene selected from the group consisting of genes each of which loses its function when a gene that codes for the release factor is defective,
the DNA construct including an altered gene of said at least one gene in which altered gene a stop codon of said at least one gene has been changed from an amber codon (UAG) to an ochre codon (UAA) or to an opal codon (UGA).

16. A recombinant bacterium for production of a non-natural protein,
which recombinant bacterium expresses tRNA that recognizes UAG codon;
which recombinant bacterium expresses an aminoacyl-tRNA synthetase which acylates the tRNA with a non-natural amino acid or an a-hydroxy acid;
(i) into which recombinant bacterium a DNA construct has been introduced, which DNA construct is for expressing, in the absence of a release factor for terminating translation at UAG codon, a function of at least one gene selected from the group consisting of genes each of which loses its function when a gene that codes for the release factor is defective and/or (ii) in which recombinant bacterium, an alteration has been introduced into said at least one gene in a chromosome of the recombinant bacterium, which alteration is for expressing the function of said at least one gene in the absence of the release factor,
the DNA construct including an altered gene of said at least one gene in which altered gene a stop codon of said at least one gene has been changed from an amber codon (UAG) to an ochre codon (UAA) or to an opal codon (UGA),
the alteration changing the stop codon of said at least one gene in the chromosome of the bacterium from the amber codon (UAG) to the ochre codon (UAA) or to the opal codon (UGA); and
in which recombinant bacterium the gene that codes for the release factor is defective.

17. The recombinant bacterium according to claim 16, which is derived from *Escherichia coli*.

18. A method of producing a non-natural protein with use of a recombinant bacterium, comprising expressing, in a recombinant bacterium set forth in claim 16 or in an extract of the recombinant bacterium,
(a) an aminoacyl-tRNA synthetase capable of activating a non-natural amino acid or an α-hydroxy acid,
(b) tRNA which recognizes UAG codon and is capable of being attached to the non-natural amino acid or the α-hydroxy acid in the presence of the aminoacyl-tRNA synthetase, and
(c) a gene that codes for a desired protein, which gene has at least one nonsense mutation occurred randomly or in a desired position.

19. The method according to claim 18, wherein the recombinant bacterium is derived from *Escherichia coli*.

20. An extract of a recombinant bacterium for use in production of a non-natural protein,
which recombinant bacterium expresses tRNA that recognizes UAG codon;
which recombinant bacterium expresses an aminoacyl-tRNA synthetase which acylates the tRNA with a non-natural amino acid or an α-hydroxy acid;
(i) into which recombinant bacterium a DNA construct has been introduced, which DNA construct is for expressing, in the absence of a release factor for terminating translation at UAG codon, a function of at least one gene selected from the group consisting of genes each of which loses its function when a gene that codes for the release factor is defective and/or (ii) in which recombinant bacterium, an alteration has been introduced into said at least one gene in a chromosome of the recombinant bacterium, which alteration is for expressing the function of said at least one gene in the absence of the release factor;
the DNA construct including an altered gene of said at least one gene in which altered gene a stop codon of said at least one gene has been changed from an amber codon (UAG) to an ochre codon (UAA) or to an opal codon (UGA),
the alteration changing the stop codon of said at least one gene in the chromosome of the bacterium from the amber codon (UAG) to the ochre codon (UAA) or to the opal codon (UGA); and
in which recombinant bacterium the gene that codes for the release factor is defective.

21. The extract according to claim 20, wherein the recombinant bacterium is derived from *Escherichia coli*.

22. The method according to claim 2, wherein, in the bacterium, another tRNA which recognizes UAG codon but is not acylated by the aminoacyl-tRNA synthetase is expressed, said method further comprising the step of causing a gene that codes for said another tRNA to be defective.

23. The method according to claim 2, wherein the non-natural protein is a non-natural protein that includes the non-natural amino acid or the α-hydroxy acid.

24. The method according to claim 2, wherein the bacterium is *Escherichia coli*.

25. The method according to claim 2, wherein said at least one gene is at least one, defect of which alone is lethal, among all genes whose translation is terminated at UAG codon.

26. The method according to claim 25, wherein:
the bacterium is *Escherichia coli*; and
said at least one gene is at least one gene selected from the group consisting of coaD, murF, hda, mreC, hemA, lpxK and lolA of *Escherichia coli*.

27. The method according to claim 26, wherein said at least one gene is any six genes selected from the group consisting of coaD, murF, hda, mreC, hemA, lpxK and lolA of *Escherichia coli*.

28. The method according to claim 26, wherein said at least one gene is coaD, hda, mreC and hemA genes of *Escherichia coli*.

29. The method according to claim 25, wherein said at least one gene further includes another gene, defect of which causes a reduction in growth rate of the bacterium.

30. The method according to claim 29, wherein said another gene defect of which causes a reduction in growth rate of the bacterium is a sucB gene of *Escherichia coli*.

31. The method according to claim 2, wherein:
the bacterium is *Escherichia coli*; and
the DNA construct is a DNA construct which expresses a function of at least one gene selected from the group consisting of coaD, murF, hda, mreC, hemA, lpxK and lolA of *Escherichia coli*.

32. The method according to claim 31, wherein the DNA construct further expresses a function of a sucB gene of *Escherichia coli*.

33. The method according to claim 2, wherein the DNA construct is selected from a bacterial artificial chromosome, a plasmid, and linear DNA, each of which is recruited in trans and/or in cis to the chromosome of the bacterium.

* * * * *

SEQUENCE LISTING

<160> NUMBER OF SEQ ID NOS: 31

<210> SEQ ID NO 1
<211> LENGTH: 1083
<212> TYPE: DNA
<213> ORGANISM: Escherichia coli

<400> SEQUENCE: 1

```
atgaagcctt ctatcgttgc caaactggaa gccctgcatg aacgccatga agaagttcag      60
gcgttgctgg gtgacgcgca aactatcgcc gaccaggaac gttttcgcgc attatcacgc     120
gaatatgcgc agttaagtga tgtttcgcgc tgttttaccg actggcaaca ggttcaggaa     180
gatatcgaaa ccgcacagat gatgctcgat gatcctgaaa tgcgtgagat ggcgcaggat     240
gaactgcgcg aagctaaaga aaaaagcgag caactggaac agcaattaca ggttctgtta     300
ctgccaaaag atcctgatga cgaacgtaac gccttcctcg aagtccgagc cggaaccggc     360
ggcgacgaag cggcgctgtt cgcgggcgat ctgttccgta tgtacagccg ttatgccgaa     420
gcccgccgct ggcgggtaga atcatgagc gccagcgagg gtgaacatgg tggttataaa     480
gagatcatcg ccaaaattag cggtgatggt gtgtatggtc gtctgaaatt tgaatccggc     540
ggtcatcgcg tgcaacgtgt tcctgctacg gaatcgcagg gtcgtattca tacttctgct     600
tgtaccgttg cggtaatgcc agaactgcct gacgcagaac tgccggacat caacccagca     660
gatttacgca ttgatacttt ccgctcgtca ggggcgggtg gtcagcacgt taacaccacc     720
gattcggcaa ttcgtattac tcacttgccg accgggattg ttgttgaatg tcaggacgaa     780
cgttcacaac ataaaaacaa agctaaagca ctttctgttc tcggtgctcg catccacgct     840
gctgaaatgg caaaacgcca acaggccgaa gcgtctaccc gtcgtaacct gctggggagt     900
ggcgatcgca gcgaccgtaa ccgtacttac aacttcccgc aggggcgcgt taccgatcac     960
cgcatcaacc tgacgctcta ccgcctggat gaagtgatgg aagtaagct ggatatgctg    1020 attgaaccga ttatccagga acatcaggcc gaccaactgg cggcgttgtc cgagcaggaa    1080
taa                                                                  1083
```

<210> SEQ ID NO 2
<211> LENGTH: 480
<212> TYPE: DNA
<213> ORGANISM: Escherichia coli

<400> SEQUENCE: 2

```
atgcaaaaac gggcgattta tccgggtact ttcgatccca ttaccaatgg tcatatcgat      60
atcgtgacgc gcgccacgca gatgttcgat cacgttattc tggcgattgc cgccagcccc     120
agtaaaaaac cgatgtttac cctggaagag cgtgtggcac tggcacagca ggcaaccgcg     180
catctgggga acgtggaagt ggtcgggttt agtgatttaa tggcgaactt cgcccgtaat     240
caacacgcta cggtgctgat tcgtggcctg cgtgcggtgg cagattttga atatgaaatg     300
cagctggcgc atatgaatcg ccacttaatg ccggaactgg aaagtgtgtt tctgatgccg     360
tcgaaagagt ggtcgtttat ctcttcatcg ttggtgaaag aggtggcgcg ccatcagggc     420
gatgtcaccc atttcctgcc ggagaatgtc catcaggcgc tgatggcgaa gttagcgtag     480
```

<210> SEQ ID NO 3
<211> LENGTH: 1359
<212> TYPE: DNA
<213> ORGANISM: Escherichia coli

<400> SEQUENCE: 3

```
atgattagcg taacccttag ccaacttacc gacattctca acggtgaact gcaaggtgca    60
gatatcaccc ttgatgctgt aaccactgat acccgaaaac tgacgccggg ctgcctgttt   120
gttgccctga aggcgaacg ttttgatgcc cacgattttg ccgaccaggc gaaagctggc    180
ggcgcaggcg cactactggt tagccgtccg ctggacatcg acctgccgca gttaatcgtc   240
aaggatacgc gtctggcgtt tggtgaactg ctgcatggg ttcgccagca agttccggcg    300
cgcgtggttg ctctgacggg gtcctccggc aaaacctccg ttaaagagat gacgcgggcg   360
attttaagcc agtgcggcaa cacgctttat acggcaggca atctcaacaa cgacatcggt   420
gtaccgatga cgctgttgcg cttaacgccg aatacgatt acgcagttat tgaacttggc    480
gcgaaccatc agggcgaaat agcctggact gtgagtctga ctcgcccgga agctgcgctg   540
gtcaacaacc tggcagcggc gcatctggaa ggttttggct cgcttgcggg tgtcgcgaaa   600
gcgaaaggtg aaatctttag cggcctgccg aaaacggta tcgccattat gaacgccgac   660
aacaacgact ggctgaactg gcagagcgta attggctcac gcaaagtgtg gcgtttctca   720
cccaatgccg ccaacagcga tttcaccgcc accaatatcc atgtgacctc gcacggtacg   780
gaatttaccc tacaaacccc aaccggtagc gtcgatgttc tcgctgccgtt gccggggcgt   840
cacaatattg cgaatgcgct ggcagccgct gcgctctcca tgtccgtggg cgcaacgctt   900
gatgctatca agcggggct ggcaaatctg aaagctgttc caggccgtct gttccccatc    960
caactggcag aaaaccagtt gctgctcgac gactcctaca cgccaatgt cggttcaatg    1020
actgcagcag tccaggtact ggctgaaatg ccgggctacc gcgtgctggt ggtgggcgat   1080
atggcggaac tgggcgctga agcgaagcc tgccatgtac aggtgggcga ggcggcaaaa    1140
gctgctggta ttgaccgcgt gttaagcgtg ggtaaacaaa gccatgctat cagcaccgcc   1200
agcggcgttg gcgaacattt tgctgataaa actgcgttaa ttacgcgtct taaattactg   1260
attgctgagc aacaggtaat tacgattta gttaagggtt cacgtagtgc cgccatggaa    1320
gaggtagtac gcgctttaca ggagaatggg acatgttag                          1359

<210> SEQ ID NO 4
<211> LENGTH: 747
<212> TYPE: DNA
<213> ORGANISM: Escherichia coli

<400> SEQUENCE: 4
gtggtaaact tctcgcgatt ttgtgaaatc ctggttgagg tatctctgaa cacaccggca    60
cagctctctt tgccacttta tcttcctgac gacgaaacct ttgcaagttt ctggccgggg   120
gataactcct ctttactggc cgcgctgcaa acgtgctgc gtcaggaaca tagcggttac    180
atctatctct gggcacgcga aggcgcgggg cgcagccatc tgctgcacgc ggcttgcgcg   240
gaattgtcgc agcgtggcga tgcggtgggc tatgtcccgc tggataaacg cacctggttt   300
gttccggaag tgctcgacgg tatggagcat tgtcgctgg tctgtatcga caacattgag    360
tgtattgcag gcgatgagtt gtgggagatg gcgattttcg atctctacaa tcgaattctg   420
gaatcgggca aaacacggtt gttgatcacc ggcgatcgtc accgcggca gttgaatctg   480
ggattaccgg atctcgcgtc gcgactcgac tgggggcaga tctacaaatt gcagccactt   540
tctgatgaag ataagttgca ggcgctacag ttacgcgcgc gtttgcgtgg ttttgaactg   600
ccggaagatg tggggcgttt cttgctgaag cggctcgaca gagaaatgcg cacgctattt   660
atgacgttgg atcagttgga tcgtgcgtcg attaccgcgc aacgtaagct gaccattccg   720
```

```
tttgtgaaag aaattctgaa gttgtag                                        747
```

<210> SEQ ID NO 5
<211> LENGTH: 1104
<212> TYPE: DNA
<213> ORGANISM: Escherichia coli

<400> SEQUENCE: 5

```
atgaagccaa tttttagccg tggcccgtcg ctacagattc gccttattct ggcggtgctg    60
gtggcgctcg gcattattat tgccgacagc cgcctgggga cgttcagtca atccgtact   120
tatatggata ccgccgtcag tcctttctac tttgtttcca atgctcctcg tgaattgctg   180
gatggcgtat cgcagacgct ggcctcgcgt gaccaattag aacttgaaaa ccgggcgtta   240
cgtcaggaac tgttgctgaa aaacagtgaa ctgctgatgc ttggacaata caaacaggag   300
aacgcgcgtc tgcgcgagct gctgggttcc ccgctgcgtc aggatgagca gaaaatggtg   360
actcaggtta tctccacggt taacgatcct tatagcgatc aagttgttat cgataaaggt   420
agcgttaatg gcgtttatga aggccagccg gtcatcagcg acaaaggtgt tgttggtcag   480
gtggtggccg tcgctaaaact gaccagtcgc gtgctgctga tttgtgatgc gacccacgcg   540
ctgccaatcc aggtgctgcg caacgatatc cgcgtaattg cagccggtaa cggttgtacg   600
gatgatttgc agcttgagca tctgccggcg aatacggata ttcgtgttgg tgatgtgctg   660
gtgacttccg gtctgggcgg tcgtttcccg gaaggctatc cggtcgcggt tgtctcttcc   720
gtaaaactcg atacccagcg cgcttatact gtgattcagg gcgtccgac tgcagggctg   780
caacgtttgc gttatctgct gctgctgtgg ggggcagatc gtaacggcgc taacccgatg   840
acgccggaag aggtgcatcg tgttgctaat gaacgtctga tgcagatgat gccgcaggta   900
ttgccttcgc cagacgcgat ggggccaaag ttacctgaac cggcaacggg gatcgctcag   960
ccgactccgc agcaaccggc gacaggaaat gcagctactg cgcctgctgc gccgacacag  1020
cctgctgcta atcgctctcc acaaagggct acgccgccgc aaagtggtgc tcaaccgcct  1080
gcgcgtgcgc cgggagggca atag                                        1104
```

<210> SEQ ID NO 6
<211> LENGTH: 987
<212> TYPE: DNA
<213> ORGANISM: Escherichia coli

<400> SEQUENCE: 6

```
atgatcgaaa aaatctggtc tggtgaatcc cctttgtggc ggctattgct gccactctcc    60
tggttgtatg gcctggtgag tggcgcgatc cgtctttgct ataaactaaa actgaagcgc   120
gcctggcgtg ccccgtacc ggttgtcgtg gttggtaatc tcaccgcagg cggcaacgga   180
aaaaccccgg tcgttgtctg gctggtggaa cagttgcaac agcgcggtat tcgcgtgggg   240
gtcgtatcgc ggggatatgg tggtaaggct gaatcttatc cgctgttatt gtcggcagat   300
accacaacag cacaggcggg tgatgaacct gtgttgattt atcaacgcac tgatgcgcct   360
gttgcggttt ctcccgttcg ttctgatgcg gtaaaagcca ttctggcgca cacccctgat   420
gtgcagatca tcgtaaccga cgacggttta cagcattacc gtctggcgcg tgatgtggaa   480
attgtcgtta ttgatggtgt gcgtcgcttt ggcaatggct ggtggttgcc ggcggggcca   540
atgcgtgagc gagcggggcg cttaaagtcg gttgatgcgg taatcgtcaa cggcggtgtc   600
cctcgcagcg gtgaaatccc catgcatctg ctgccgggtc aggcggtgaa tttacgtacc   660
ggtacgcgtt gtgacgttgc tcagcttgaa catgtagtgg cgatggcggg gattgggcat   720
```

```
ccgccgcgct tttttgccac gctgaagatg tgtggcgtac aaccggaaaa atgtgtaccg    780
ctggccgatc atcagtcttt gaaccatgcg gatgtcagtg cgttggtaag cgccgggcaa    840
acgctggtaa tgactgaaaa agatgcggtg aaatgccggg cctttgcaga agaaaattgg    900
tggtatttgc ctgtagacgc acagctttca ggtgatgaac cagcgaaact gcttacgcaa    960
ctaaccttgc tggcttctgg caactag                                        987

<210> SEQ ID NO 7
<211> LENGTH: 1257
<212> TYPE: DNA
<213> ORGANISM: Escherichia coli

<400> SEQUENCE: 7
atgacccttt tagcactcgg tatcaaccat aaaacggcac ctgtatcgct gcgagaacgt     60
gtatcgtttt cgccggataa gctcgatcag gcgcttgaca gcctgcttgc gcagccgatg    120
gtgcagggcg gcgtggtgct gtcgacgtgc aaccgcacgg aactttatct tagcgttgaa    180
gagcaggaca acctgcaaga ggcgttaatc cgctggcttt gcgattatca caatcttaat    240
gaagaagatc tgcgtaaaag cctctactgg catcaggata cgacgcggt tagccattta    300 atgcgtgttg ccagcggcct ggattcactg gttctggggg agccgcagat cctcggtcag    360
gttaaaaaag cgtttgccga ttcgcaaaaa ggtcatatga aggccagcga actggaacgc    420
atgttccaga atctttctc tgtcgcgaaa cgcgttcgca ctgaaacaga tatcggtgcc    480
agcgctgtgt ctgtcgcttt tgcggcttgt acgctggcgc ggcagatctt tgaatcgctc    540
tctacggtca cagtgttgct ggtaggcgcg ggcgaaacta tcgagctggt ggcgcgtcat    600
ctgcgcgaac acaaagtaca gaagatgatt atcgccaacc gcactcgcga acgtgcccaa    660
attctggcag atgaagtcgg cgcggaagtg attgccctga gtgatatcga cgaacgtctg    720
cgcgaagccg atatcatcat cagttccacc gccagcccgt taccgattat cgggaaaggc    780
atggtggagc gcgcattaaa aagccgtcgc aaccaaccaa tgctgttggt ggatattgcc    840
gttccgcgcg atgttgagcc ggaagttggc aaactggcga atgcttatct ttatagcgtt    900
gatgatctgc aaagcatcat ttcgcacaac ctggcgcagc gtaaagccgc agcggttgag    960
gcggaaacta ttgtcgctca ggaaaccagc gaatttatgg cgtggctgcg agcacaaagc   1020
gccagcgaaa ccattcgcga gtatcgcagc aggcagagc aagttcgcga tgagttaacc   1080
gccaaagcgt tagcggccct tgagcagggc ggcgacgcgc aagccattat gcaggatctg   1140
gcatggaaac tgactaaccg cttgatccat gcgccaacga atcacttca acaggccgcc   1200 cgtgacgggg ataacgaacg cctgaatatt ctgcgcgaca gcctcgggct ggagtag     1257

<210> SEQ ID NO 8
<211> LENGTH: 612
<212> TYPE: DNA
<213> ORGANISM: Escherichia coli

<400> SEQUENCE: 8
atgaaaaaaa ttgccatcac ctgtgcatta ctctcaagct tagtagcaag cagcgtttgg     60
gctgatgccg caagcgatct gaaaagccgc ctggataaag tcagcagctt ccacgccagc    120
ttcacacaaa aagtgactga cggtagcggc gcggcggtgc aggaaggtca gggcgatctg    180
tgggtgaaac gtccaaactt attcaactgg catatgacaa aacctgatga agcattctg    240 gtttctgacg gtaaaacact gtggttctat aacccgttcg ttgagcaagc tacggcaacc    300
```

```
tggctgaaag atgccaccgg taatacgccg tttatgctga ttgcccgcaa ccagtccagc      360
gactggcagc agtacaatat caaacagaat ggcgatgact ttgtcctgac gccgaaagcc      420
agcaatggca atctgaagca gttcaccatt aacgtgggac gtgatggcac aatccatcag      480
tttagcgcgg tggagcagga cgatcagcgc agcagttatc aactgaaatc ccagcaaaat      540
ggggctgtgg atgcagcgaa atttaccttc accccgccgc aaggcgtcac ggtagatgat      600
caacgtaagt ag                                                          612

<210> SEQ ID NO 9
<211> LENGTH: 414
<212> TYPE: DNA
<213> ORGANISM: Escherichia coli

<400> SEQUENCE: 9
atgagtgaca tgaataatcc ggccgatgac aacaacggcg caatggacga tctgtgggct       60
gaagcgttga gcgaacaaaa atcaaccagc agcaaaagcg ctgccgagac ggtgttccag      120
caatttggcg gtggtgatgt cagcggaacg ttgcaggata tcgacctgat tatggatatt      180
ccggtcaagc tgaccgtcga gctgggccgt acgcggatga ccatcaaaga gctgttgcgt      240
ctgacgcaag gtccgtcgt ggcgctggac ggtctggcgg cgaaccact ggatattctg        300 atcaacggtt atttaatcgc ccagggcgaa gtggtggtcg ttgccgataa atatggcgtg      360
cggatcaccg atatcattac tccgtctgag cgaatgcgcc gcctgagccg ttag            414

<210> SEQ ID NO 10
<211> LENGTH: 738
<212> TYPE: DNA
<213> ORGANISM: Escherichia coli

<400> SEQUENCE: 10
atgcgtcgtt tattgtctgt cgcacctgtc cttctctggc tgattacgcc cctcgccttc       60
gcgcaactgc cgggtatcac cagccagccg ctgcctggcg gtggacaaag ctggtcgctc      120
ccggtgcaga cgctggtgtt catcaccctc gttgacgttta ttccggcaat tttactgatg     180
atgaccagtt tcacccgcat catcattgtt tttggtttat tgcgtaacgc gctgggaaca      240
ccctccgcgc cacctaacca ggtattgctg gggctggcac tgtttttgac cttttttatt      300
atgtcaccgg tgatcgacaa aatttatgta atgcgtacc agccattcag cgaagagaaa      360
atatcaatgc aggaggcgct ggaaaaaggg gcgcagccgc tgcgtgagtt tatgctgcgt      420
cagacccgtg aggcagattt aggggttgtt gccagactgg cgaataccgg cccgttgcag      480
ggacctgaag ccgtgccgat gcgcattttg ctcccggcct acgtgaccag cgagttgaaa      540
accgcatttc agataggctt cacgattttc atccctttttt tgattatcga cctggtgata    600
gccagcgtgt tgatggcatt ggggatgatg atggttcccc cagccaccat tgctctgccc      660 tttaaaactga tgctgtttgt actggtggat ggctggcaat tgctggtcgg ttcgctggcg    720
cagagctttt acagctag                                                    738

<210> SEQ ID NO 11
<211> LENGTH: 270
<212> TYPE: DNA
<213> ORGANISM: Escherichia coli

<400> SEQUENCE: 11
atgacacctg aatcggtcat gatgatgggg actgaagcga tgaaagtcgc gctggcactg       60
gctgccccgc tattgttggt agcgttggtc acgggcctta tcatcagtat tttgcaggcc      120
```

```
gccacgcaga ttaacgaaat gacgctgtcg tttattccga aaatcatcgc cgtatttatc    180
gccattatta ttgccggacc gtggatgctc aatctgttgc tggattacgt ccgcaccttg    240
ttcactaacc tgccgtatat catcgggtag                                     270

<210> SEQ ID NO 12
<211> LENGTH: 1218
<212> TYPE: DNA
<213> ORGANISM: Escherichia coli

<400> SEQUENCE: 12
atgagtagcg tagatattct ggtccctgac ctgcctgaat ccgtagccga tgccaccgtc     60
gcaacctggc ataaaaaacc cggcgacgca gtcgtacgtg atgaagtgct ggtagaaatc    120
gaaactgaca aagtggtact ggaagtaccg catcagcag acggcattct ggatgcggtt     180
ctggaagatg aaggtacaac ggtaacgtct cgtcagatcc ttggtcgcct gcgtgaaggc    240
aacagcgccg gtaaagaaac cagcgccaaa tctgaagaga aagcgtccac tccggcgcaa    300
cgccagcagg cgtctctgga gagcaaaac aacgatgcgt taagcccggc gatccgtcgc    360
ctgctggctt aacacaatct cgacgccagc gccattaaag caccggtgt gggtggtcgt    420 ctgactcgtg aagatgtgga aaaacatctg gcgaaagccc cggcgaaaga gtctgctccg    480
gcagcggctg ctccggcggc gcaaccggct ctggctgcac gtagtgaaaa acgtgtcccg    540
atgactcgcc tgcgtaagcg tgtggcagag cgtctgctgg aagcgaaaaa ctccaccgcc    600
atgctgacca cgttcaacga agtcaacatg aagccgatta tggatctgcg taagcagtac    660
ggtgaagcgt ttgaaaaacg ccacggcatc cgtctgggct tatgtccctt ctacgtgaaa    720
gcggtggttg aagcccctgaa acgttacccg gaagtgaacg cttctatcga cggcgatgac    780
gtggtttacc acaactattt cgacgtcagc atggcggttt ctacgccgcg cggcctggtg    840
acgccggttc tgcgtgatgt cgataccctc ggcatggcag acatcgagaa gaaaatcaaa    900
gagctggcag tcaaaggccg tgacggcaag ctgaccgttg aagatctgac cggtggtaac    960
ttcaccatca ccaacggtgg tgtgttcggt tccctgatgt ctacgccgat catcaacccg   1020
ccgcagagcg caattctggg tatgcacgct atcaaagatc gtccgatggc ggtgaatggt   1080
caggttgaga tcctgccgat gatgtacctg gcgctgtcct acgatcaccg tctgatcgat   1140
ggtcgcgaat ccgtgggctt cctggtaacg atcaaagagt tgctggaaga tccgacgcgt   1200
ctgctgctgg acgtgtag                                                1218

<210> SEQ ID NO 13
<211> LENGTH: 1176
<212> TYPE: DNA
<213> ORGANISM: Escherichia coli

<400> SEQUENCE: 13
atgacaaatc aaccaacgga aattgccatt gtcggcggag gaatggtcgg cggcgcactg     60
gcgctggggc tggcacagca cggatttgcg gtaacggtga tcgagcacgc agaaccagcg    120
ccgtttgtcg ctgatagcca accggacgtg cggatctcgg cgatcagcgc ggcttcggta    180
tcattgctta aagggttagg ggtctgggat gcagtacagg ctatgcgttg ccatccttac    240
cgcagactgg aaacgtggga gtgggaaacg gcgcatgtgg tgtttgacgc cgctgaactt    300
aagctaccgc tgcttggcta tatggtggaa acactgtcc tgcaacaggc gttgtggcag    360
gcgctggaag cgcatccgaa agtaacgtta cgtgtgccag gctcgctgat tgcgctgcat    420
```

```
cgccatgatg atcttcagga gctggagctg aaaggcggtg aagtgattcg cgcgaagctg      480
gtgattggtg ccgacggcgc aaattcgcag gtgcggcaga tggcgggaat tggcgttcat      540
gcatggcagt atgcgcagtc gtgcatgttg attagcgtcc agtgcgagaa cgatcccggc      600
gacagcacct ggcagcaatt tactccggac ggaccgcgtg cgtttctgcc gttgtttgat      660
aactgggcat cgctggtgtg gtatgactct ccggcgcgta ttcgccagtt gcagaatatg      720
aatatggcac agctccaggc ggaaatcgcg aagcatttcc cgtcgcgtct gggttacgtt      780
acaccgcttg ccgctggtgc gtttccgctg acgcgtcgcc atgcgttgca gtacgtgcag      840
ccagggcttg cgctggtggg cgatgccgcg cataccatcc atccgctggc ggggcaggga      900
gtgaatcttg gttatcgtga tgtcgatgcc ctgattgatg ttctggtcaa cgcccgcagc      960
tacggcgaag cgtgggccag ttatcctgtc ctcaagcgtt accagatgcg cgcatggcg      1020 gataacttca ttatgcaaag cggtatggat ctgttttatg ccggattcag caataatctg      1080
ccaccactgc gttttatgcg taatctcggg ttaatggcgg cggagcgtgc tggcgtgttg      1140
aaacgtcagg cgctgaaata tgcgttaggg ttgtag                                1176

<210> SEQ ID NO 14
<211> LENGTH: 687
<212> TYPE: DNA
<213> ORGANISM: Escherichia coli

<400> SEQUENCE: 14
atgcaaaagc taaaacagca ggtatttgaa gccaacatgg agctgccgcg ctacgggctg       60 gtgacctta cctggggcaa cgtcagcgct atcgaccgcg aacgcgggct ggtggtgatc      120
aagcccagcg gcgttgccta cgaaaccatg aaagcggccg atatggtggt ggttgatatg      180
agcggcaagg tggtggaagg ggagtatcgc ccatcttccg acactgcgac gcatctcgaa      240
ctctaccgtc gttacccgtc gcttggtggc attgtccata cccactccac tcatgccacc      300
gcatgggcgc aggcggggct ggcgatcccg gcgttaggca ccacgcacgc cgactacttc      360
tttggcgaca ttccgtgtac gcgcgggtta agcgaagaag aggtgcaggg cgagtatgaa      420
ctgaacaccg gcaaagtgat tatcgaaacg ctgggcaacg ccgagccgct gcatacgccg      480
ggaattgtgg tgtatcagca cgggccgttc gcctggggga agatgctca cgatgcggtg      540 cataacgcgg tggtgatgga agaagtggcg aaaatggcgt ggattgcccg cggcattaac      600
ccacaactca atcacatcga cagcttcctg atgaataaac acttcatgcg taaacacggt      660
cctaacgctt attacgggca gaagtag                                          687

<210> SEQ ID NO 15
<211> LENGTH: 240
<212> TYPE: DNA
<213> ORGANISM: Escherichia coli

<400> SEQUENCE: 15
atggaaaacc tgaatatgga tctgctgtac atggctgccg ctgtgatgat gggtctggcg       60
gcaatcggtg ctgcgatcgg tatcggcatc ctcggggta aattcctgga aggcgcagcg      120
cgtcaacctg atctgattcc tctgctgcgt actcagttct ttatcgttat gggtctggtg      180
gatgctatcc cgatgatcgc tgtaggtctg ggtctgtacg tgatgttcgc tgtcgcgtag      240

<210> SEQ ID NO 16
<211> LENGTH: 954
<212> TYPE: DNA
<213> ORGANISM: Escherichia coli
```

<400> SEQUENCE: 16

```
atgtatacga agattattgg tactggcagc tatctgcccg aacaagtgcg acaaacgcc      60
gatttggaaa aaatggtgga cacctctgac gagtggattg tcactcgtac cggtatccgc    120
gaacgccaca ttgccgcgcc aaacgaaacc gtttcaacca tgggctttga agcggcgaca    180
cgcgcaattg agatggcggg cattgagaaa gaccagattg cctgatcgt tgtggcaacg     240
acttctgcta cgcacgcttt cccgagcgca gcttgtcaga ttcaaagcat gttgggcatt    300
aaaggttgcc cggcatttga cgttgcagca gcctgcgcag gtttcaccta tgcattaagc    360
gtagccgatc aatacgtgaa atctgggcg gtgaagtatg ctctggtcgt cggttccgat     420
gtactggcgc gcacctgcga tccaaccgat cgtgggacta ttattatttt tggcgatggc    480
gcgggcgctg cggtgctggc tgcctctgaa gagccgggaa tcatttccac ccatctgcat    540
gccgacggta gttatggtga attgctgacg ctgccaaacg ccgaccgcgt gaatccagag    600
aattcaattc atctgacgat ggcgggcaac gaagtcttca aggttgcggt aacggaactg    660
gcgcacatcg ttgatgagac gctggcggcg aataatcttg accgttctca actggactgg    720
ctggttccgc atcaggctaa cctgcgtatt atcagtgcaa cggcgaaaaa actcggtatg    780
tctatggata atgtcgtggt gacgctggat cgccacggta ataactctgc ggcctctgtc    840
ccgtgcgcgc tggatgaagc tgtacgcgac gggcgcatta agccggggca gttggttctg    900
cttgaagcct ttggcggtgg attcacctgg ggctccgcgc tggttcgttt ctag          954
```

<210> SEQ ID NO 17
<211> LENGTH: 219
<212> TYPE: PRT
<213> ORGANISM: Artificial Sequence
<220> FEATURE:
<223> OTHER INFORMATION: Synthetic

<400> SEQUENCE: 17

```
Met Glu Lys Lys Ile Thr Gly Tyr Thr Gln Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
            85                  90                  95

Glu Gln Thr Glu Thr Phe Ser Ser Leu Trp Ser Glu Tyr His Asp Asp
        100                 105                 110

Phe Arg Gln Phe Leu His Ile Tyr Ser Gln Asp Val Ala Cys Tyr Gly
    115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
            165                 170                 175

Tyr Thr Gln Gly Asp Lys Val Leu Met Pro Leu Ala Ile Gln Val His
```

```
                    180                 185                 190
His Ala Val Cys Asp Gly Phe His Val Gly Arg Met Leu Asn Glu Leu
            195                 200                 205

Gln Gln Tyr Cys Asp Glu Trp Gln Gly Gly Ala
        210                 215

<210> SEQ ID NO 18
<211> LENGTH: 219
<212> TYPE: PRT
<213> ORGANISM: Artificial Sequence
<220> FEATURE:
<223> OTHER INFORMATION: Synthetic

<400> SEQUENCE: 18

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215

<210> SEQ ID NO 19
<211> LENGTH: 252
<212> TYPE: PRT
<213> ORGANISM: Artificial Sequence
<220> FEATURE:
<223> OTHER INFORMATION: Synthetic

<400> SEQUENCE: 19

Met Ala Ser Met Thr Gly Gly Gln Gln Met Gly Arg Asp Pro Gln Ser
1               5                   10                  15

Gln Ser Gln Ser Gln Ser Gln Ser Asn Ser Gly Val Thr Lys Asn Ser
            20                  25                  30

Gln Ser Pro Ile Leu Gly Tyr Trp Lys Ile Lys Gly Leu Val Gln Pro
        35                  40                  45
```

Thr Arg Leu Leu Leu Glu Tyr Leu Glu Glu Lys Tyr Glu Glu His Leu
 50                  55                  60

Tyr Glu Arg Asp Glu Gly Asp Lys Trp Arg Asn Lys Lys Phe Glu Leu
 65                  70                  75                  80

Gly Leu Glu Phe Pro Asn Leu Pro Tyr Tyr Ile Asp Gly Asp Val Lys
                 85                  90                  95

Leu Thr Gln Ser Met Ala Ile Ile Arg Tyr Ile Ala Asp Lys His Asn
             100                 105                 110

Met Leu Gly Gly Cys Pro Lys Glu Arg Ala Glu Ile Ser Met Leu Glu
         115                 120                 125

Gly Ala Val Leu Asp Ile Arg Tyr Gly Val Ser Arg Ile Ala Tyr Ser
130                 135                 140

Lys Asp Phe Glu Thr Leu Lys Val Asp Phe Leu Ser Lys Leu Pro Glu
145                 150                 155                 160

Met Leu Lys Met Phe Glu Asp Arg Leu Cys His Lys Thr Tyr Leu Asn
                165                 170                 175

Gly Asp His Val Thr His Pro Asp Phe Met Leu Tyr Asp Ala Leu Asp
            180                 185                 190

Val Val Leu Tyr Met Asp Pro Met Cys Leu Asp Ala Phe Pro Lys Leu
        195                 200                 205

Val Cys Phe Lys Lys Arg Ile Glu Ala Ile Pro Gln Ile Asp Lys Tyr
210                 215                 220

Leu Lys Ser Ser Lys Tyr Ile Ala Trp Pro Leu Gln Gly Trp Gln Ala
225                 230                 235                 240

Thr Phe Gly Gly Gly Asp His Pro Pro Lys Ser Asp
                245                 250

<210> SEQ ID NO 20
<211> LENGTH: 252
<212> TYPE: PRT
<213> ORGANISM: Artificial Sequence
<220> FEATURE:
<223> OTHER INFORMATION: Synthetic

<400> SEQUENCE: 20

Met Ala Ser Met Thr Gly Gly Gln Gln Met Gly Arg Asp Pro Tyr Ser
1                5                  10                  15

Tyr Ser Tyr Ser Tyr Ser Tyr Ser Asn Ser Gly Val Thr Lys Asn Ser
                 20                  25                  30

Tyr Ser Pro Ile Leu Gly Tyr Trp Lys Ile Lys Gly Leu Val Gln Pro
             35                  40                  45

Thr Arg Leu Leu Leu Glu Tyr Leu Glu Glu Lys Tyr Glu Glu His Leu
 50                  55                  60

Tyr Glu Arg Asp Glu Gly Asp Lys Trp Arg Asn Lys Lys Phe Glu Leu
 65                  70                  75                  80

Gly Leu Glu Phe Pro Asn Leu Pro Tyr Tyr Ile Asp Gly Asp Val Lys
                 85                  90                  95

Leu Thr Gln Ser Met Ala Ile Ile Arg Tyr Ile Ala Asp Lys His Asn
             100                 105                 110

Met Leu Gly Gly Cys Pro Lys Glu Arg Ala Glu Ile Ser Met Leu Glu
         115                 120                 125

Gly Ala Val Leu Asp Ile Arg Tyr Gly Val Ser Arg Ile Ala Tyr Ser
    130                 135                 140

Lys Asp Phe Glu Thr Leu Lys Val Asp Phe Leu Ser Lys Leu Pro Glu
145                 150                 155                 160

Met Leu Lys Met Phe Glu Asp Arg Leu Cys His Lys Thr Tyr Leu Asn
                165                 170                 175
Gly Asp His Val Thr His Pro Asp Phe Met Leu Tyr Asp Ala Leu Asp
            180                 185                 190
Val Val Leu Tyr Met Asp Pro Met Cys Leu Asp Ala Phe Pro Lys Leu
        195                 200                 205
Val Cys Phe Lys Lys Arg Ile Glu Ala Ile Pro Gln Ile Asp Lys Tyr
    210                 215                 220
Leu Lys Ser Ser Lys Tyr Ile Ala Trp Pro Leu Gln Gly Trp Gln Ala
225                 230                 235                 240
Thr Phe Gly Gly Gly Asp His Pro Pro Lys Ser Asp
                245                 250

<210> SEQ ID NO 21
<211> LENGTH: 252
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (15)..(15)
<223> OTHER INFORMATION: 3-iodo-L-tyrosine
<220> FEATURE:
<221> NAME/KEY: MUTAGEN
<222> LOCATION: (17)..(17)
<223> OTHER INFORMATION: 3-iodo-L-tyrosine
<220> FEATURE:
<221> NAME/KEY: MUTAGEN
<222> LOCATION: (19)..(19)
<223> OTHER INFORMATION: 3-iodo-L-tyrosine
<220> FEATURE:
<221> NAME/KEY: MUTAGEN
<222> LOCATION: (21)..(21)
<223> OTHER INFORMATION: 3-iodo-L-tyrosine
<220> FEATURE:
<221> NAME/KEY: MUTAGEN
<222> LOCATION: (23)..(23)
<223> OTHER INFORMATION: 3-iodo-L-tyrosine
<220> FEATURE:
<221> NAME/KEY: MUTAGEN
<222> LOCATION: (33)..(33)
<223> OTHER INFORMATION: 3-iodo-L-tyrosine

<400> SEQUENCE: 21

Met Ala Ser Met Thr Gly Gly Gln Gln Met Gly Arg Asp Pro Xaa Ser
1               5                   10                  15
Xaa Ser Xaa Ser Xaa Ser Xaa Ser Asn Ser Gly Val Thr Lys Asn Ser
            20                  25                  30
Xaa Ser Pro Ile Leu Gly Tyr Trp Lys Ile Lys Gly Leu Val Gln Pro
        35                  40                  45
Thr Arg Leu Leu Leu Glu Tyr Leu Glu Glu Lys Tyr Glu Glu His Leu
    50                  55                  60
Tyr Glu Arg Asp Glu Gly Asp Lys Trp Arg Asn Lys Lys Phe Glu Leu
65                  70                  75                  80
Gly Leu Glu Phe Pro Asn Leu Pro Tyr Tyr Ile Asp Gly Asp Val Lys
                85                  90                  95
Leu Thr Gln Ser Met Ala Ile Ile Arg Tyr Ile Ala Asp Lys His Asn
            100                 105                 110
Met Leu Gly Gly Cys Pro Lys Glu Arg Ala Glu Ile Ser Met Leu Glu
        115                 120                 125
Gly Ala Val Leu Asp Ile Arg Tyr Gly Val Ser Arg Ile Ala Tyr Ser
    130                 135                 140

```
Lys Asp Phe Glu Thr Leu Lys Val Asp Phe Leu Ser Lys Leu Pro Glu
145                 150                 155                 160

Met Leu Lys Met Phe Glu Asp Arg Leu Cys His Lys Thr Tyr Leu Asn
            165                 170                 175

Gly Asp His Val Thr His Pro Asp Phe Met Leu Tyr Asp Ala Leu Asp
        180                 185                 190

Val Val Leu Tyr Met Asp Pro Met Cys Leu Asp Ala Phe Pro Lys Leu
        195                 200                 205

Val Cys Phe Lys Lys Arg Ile Glu Ala Ile Pro Gln Ile Asp Lys Tyr
    210                 215                 220

Leu Lys Ser Ser Lys Tyr Ile Ala Trp Pro Leu Gln Gly Trp Gln Ala
225                 230                 235                 240

Thr Phe Gly Gly Gly Asp His Pro Pro Lys Ser Asp
                245                 250

<210> SEQ ID NO 22
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (3)..(3)
<223> OTHER INFORMATION: 3-iodo-L-tyrosine
<220> FEATURE:
<221> NAME/KEY: MUTAGEN
<222> LOCATION: (5)..(5)
<223> OTHER INFORMATION: 3-iodo-L-tyrosine
<220> FEATURE:
<221> NAME/KEY: MUTAGEN
<222> LOCATION: (7)..(7)
<223> OTHER INFORMATION: 3-iodo-L-tyrosine
<220> FEATURE:
<221> NAME/KEY: MUTAGEN
<222> LOCATION: (9)..(9)
<223> OTHER INFORMATION: 3-iodo-L-tyrosine
<220> FEATURE:
<221> NAME/KEY: MUTAGEN
<222> LOCATION: (11)..(11)
<223> OTHER INFORMATION: 3-iodo-L-tyrosine

<400> SEQUENCE: 22

Asp Pro Xaa Ser Xaa Ser Xaa Ser Xaa Ser Xaa Ser Asn Ser Gly Val
1               5                   10                  15

Thr Lys

<210> SEQ ID NO 23
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (3)..(3)
<223> OTHER INFORMATION: 3-iodo-L-tyrosine

<400> SEQUENCE: 23

Asn Pro Xaa Ser Ser Pro Ile Leu Gly Tyr Trp Lys
1               5                   10

<210> SEQ ID NO 24
<211> LENGTH: 18
<212> TYPE: PRT
<213> ORGANISM: Artificial Sequence
<220> FEATURE:
```

<223> OTHER INFORMATION: Synthetic

<400> SEQUENCE: 24

Asp Pro Gln Ser Gln Ser Gln Ser Gln Ser Asn Ser Gly Val
1               5                   10                  15

Thr Lys

<210> SEQ ID NO 25
<211> LENGTH: 12
<212> TYPE: PRT
<213> ORGANISM: Artificial Sequence
<220> FEATURE:
<223> OTHER INFORMATION: Synthetic

<400> SEQUENCE: 25

Asn Pro Gln Ser Ser Pro Ile Leu Gly Tyr Trp Lys
1               5                   10

<210> SEQ ID NO 26
<211> LENGTH: 18
<212> TYPE: PRT
<213> ORGANISM: Artificial Sequence
<220> FEATURE:
<223> OTHER INFORMATION: Synthetic

<400> SEQUENCE: 26

Asp Pro Tyr Ser Tyr Ser Tyr Ser Tyr Ser Asn Ser Gly Val
1               5                   10                  15

Thr Lys

<210> SEQ ID NO 27
<211> LENGTH: 12
<212> TYPE: PRT
<213> ORGANISM: Artificial Sequence
<220> FEATURE:
<223> OTHER INFORMATION: Synthetic

<400> SEQUENCE: 27

Asn Pro Tyr Ser Ser Pro Ile Leu Gly Tyr Trp Lys
1               5                   10

<210> SEQ ID NO 28
<211> LENGTH: 92
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (35)..(38)
<223> OTHER INFORMATION: n is a, c, g, or t
<220> FEATURE:
<221> NAME/KEY: misc_feature
<222> LOCATION: (42)..(45)
<223> OTHER INFORMATION: n is a, c, g, or t

<400> SEQUENCE: 28
cgcatttggg gtatcgccaa gcggtaaggc accgnnnnct annnncggca ttccgaggtt      60
cgaatcctcg tacccagcc atttatcaca ga                                    92

<210> SEQ ID NO 29
<211> LENGTH: 43
<212> TYPE: DNA
<213> ORGANISM: Artificial Sequence
<220> FEATURE:
<223> OTHER INFORMATION: Synthetic

```
<400> SEQUENCE: 29
tgataaatgg ctggggtacg aggattcgaa cctcggaatg ccg          43

<210> SEQ ID NO 30
<211> LENGTH: 38
<212> TYPE: DNA
<213> ORGANISM: Artificial Sequence
<220> FEATURE:
<223> OTHER INFORMATION: Synthetic

<400> SEQUENCE: 30
cggtgcctta ccgcttggcg ataccccaaa tgcgtctg                38

<210> SEQ ID NO 31
<211> LENGTH: 24
<212> TYPE: PRT
<213> ORGANISM: Artificial Sequence
<220> FEATURE:
<223> OTHER INFORMATION: Synthetic

<400> SEQUENCE: 31

Met Lys Asp His Leu Ile His Asn His His Lys His Glu His Ala His
1               5                   10                  15

Ala Leu Val Pro Arg Gly Ser His
            20
```